(12) United States Patent
Doudna et al.

(10) Patent No.: US 8,440,430 B2
(45) Date of Patent: May 14, 2013

(54) MODIFIED DICER POLYPEPTIDE AND METHODS OF USE THEREOF

(75) Inventors: Jennifer Doudna, Berkeley, CA (US); Enbo Ma, Berkeley, CA (US); Ian J. MacRae, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 18 days.

(21) Appl. No.: 12/922,428

(22) PCT Filed: Mar. 18, 2009

(86) PCT No.: PCT/US2009/037556
§ 371 (c)(1),
(2), (4) Date: Dec. 20, 2010

(87) PCT Pub. No.: WO2009/117513
PCT Pub. Date: Sep. 24, 2009

(65) Prior Publication Data
US 2011/0117610 A1    May 19, 2011

Related U.S. Application Data

(60) Provisional application No. 61/070,286, filed on Mar. 21, 2008.

(51) Int. Cl.
*C12P 19/34* (2006.01)
*C07H 21/04* (2006.01)

(52) U.S. Cl.
USPC ....... 435/91.3; 435/199; 435/243; 435/320.1; 536/23.2

(58) Field of Classification Search .................. None
See application file for complete search history.

(56) References Cited

U.S. PATENT DOCUMENTS

2003/0224432 A1    12/2003  Myers et al.
2004/0018999 A1*    1/2004  Beach et al. .................... 514/44
2007/0031417 A2     2/2007  Mello

FOREIGN PATENT DOCUMENTS

WO    WO 03/091433    11/2003
WO    WO 03/093430    11/2003
WO    WO 2005/017144   2/2005

OTHER PUBLICATIONS

Billy et al. (PNAS 2001, Vo. 98: 14428-14433).*
Barthel et al. (J. Bacteriology 2001, vol. 183(19): 5482-5490).*
Zhang et al. (EMBO 2002, vol. 21: 5875-5885).*
GenBank Accession ID NP_803187 (WT dicer I sequence) Feb. 23, 2008 http://www.ncbi.nlm.nih.gov/sviewer/viewer.fcgi?29294651: NCB1:20825731.
Gross et al., "Mutational Analysis of Vaccinia Virus Nucleoside Triphosphate Phosphohydrolase II, a DExH box RNA Helicase", J. Virol., 69(8):4727-4736 (1995).
Gross et al., "The QRxGRxGRxxxG Motif of the Vaccinia Virus DExH Box RNA Helicase NPH-II is Required for ATP Hydrolysis and RNA Unwinding but Not for RNA Binding", J. Virol. 70(3):1706-1713 (1996).
Lim et al., "Functional analysis of dicer-2 missense mutations in the siRNA pathway of Drosophila", Biochem. Biophys. Res. Commun., 371(3):525-530 (2008).
Ma et al., "Autoinhibition of Human Dicer by its Internal Helicase Domain", J Mol. Biol., 380:237-243 (2008).
MacRae and Doudna, "Ribonuclease revisited: structural insights into ribonuclease III family enzymes", *Curr. Opin. Struct. Biol.* 17:138-145 (2007).
Soifer et al., "A role for the Dicer helicase domain in the processing of thermodynamically unstable hairpin RNAs", Nucleic Acids Research, 36(20):6511-6522 (2008).
Zhang et al., "Single Processing Center Models for Human Dicer and Bacterial RNase III", Cell, 118:57-68 (2004).

* cited by examiner

*Primary Examiner* — Kimberly Chong
(74) *Attorney, Agent, or Firm* — Paula A. Borden; Bozicevic, Field & Francis LLP.

(57) ABSTRACT

A modified Dicer polypeptide is provided, which modified Dicer polypeptide exhibits enhanced catalytic activity. Also provided is a method for producing small regulatory RNAs from a dsRNA, involving contacting a dsRNA with a subject modified Dicer. Small regulatory RNAs produced by a subject method find use in a variety of applications, including research and therapeutic applications.

18 Claims, 21 Drawing Sheets

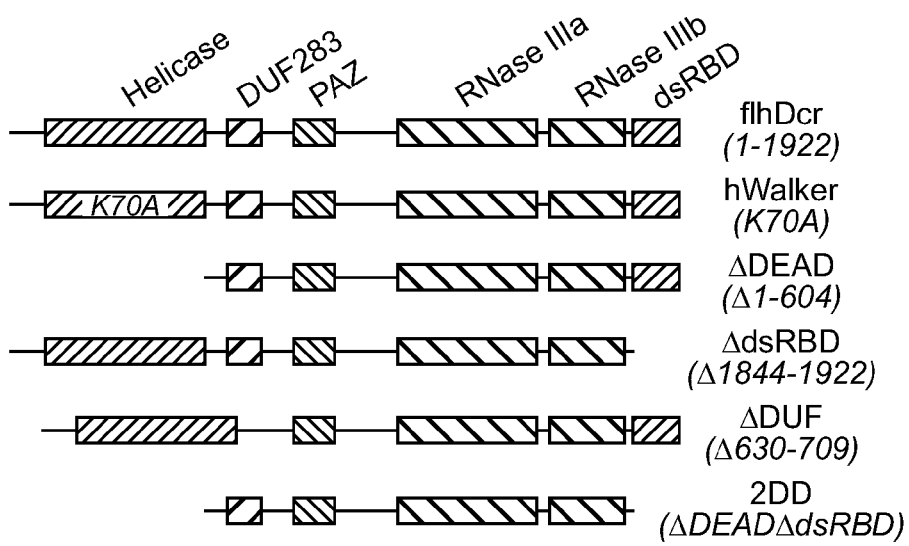
FIG. 1A
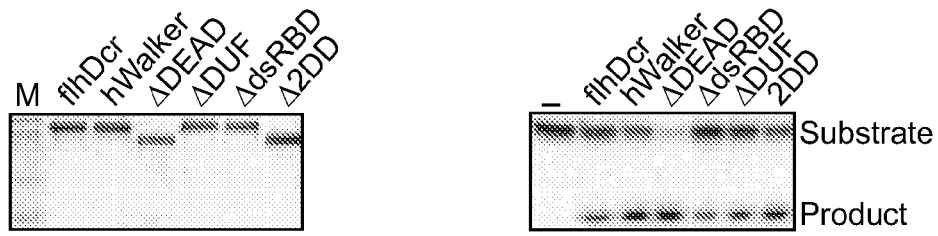
FIG. 1B                    FIG. 1C

1st order rate of hDcr proteins (fmols per min)

| RNA | flhDcr | hwalker | ΔDEAD | ΔDUF | ΔRBD | 2DD |
|---|---|---|---|---|---|---|
| dsRNA | 0.18 | 0.52 | 1.6 | 0.064 | 0.052 | 0.268 |
| Pre-het7 | 1.08 | 1.12 | 1.24 | 1.10 | 0.4 | 0.28 |

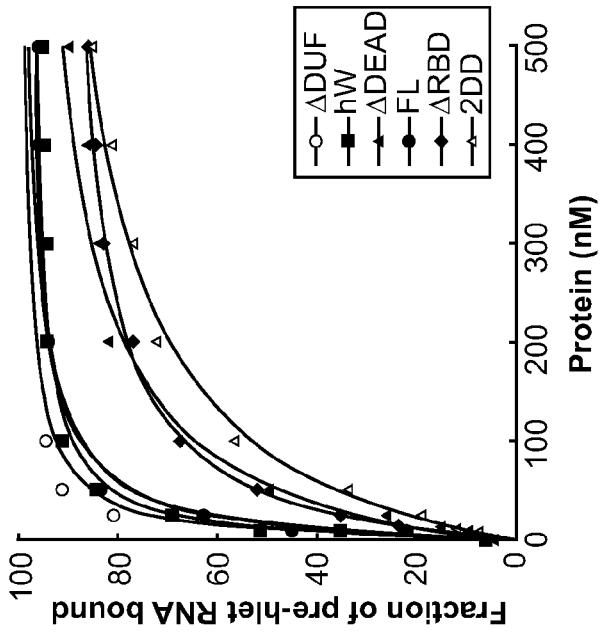
FIG. 3A
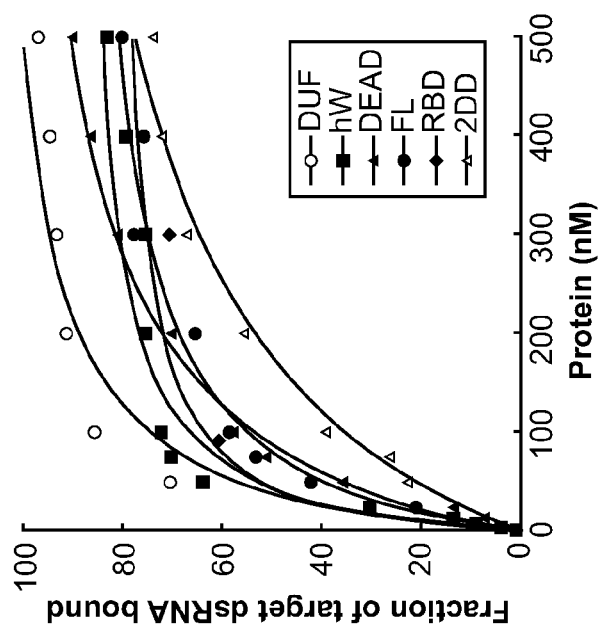
FIG. 3B
Binding affinity ($K_d$, nM) of hDcr proteins to duplex RNAs
| RNA | flhDcr | hWalker | ΔDEAD | ΔDUF | ΔRBD | 2DD |
|---|---|---|---|---|---|---|
| dsRNA | 75 | 36.5 | 119.2 | 42.3 | 31.5 | 257.8 |
| Pre-hlet7 | 30.3 | 27.0 | 80.2 | 33.1 | 32.25 | 140.2 |
FIG. 3C Kinetic analysis of wild-type hDcr and ΔDEAD hDcr

| Protein | $K_m$ (nM) | $V_{max}$ (nM s$^{-1}$) | [Protein] (nM) | $k_{cat}$ (s$^{-1}$) | $k_{cat} K_m^{-1}$ |
|---|---|---|---|---|---|
| fl-hDcr | 18.8 | 0.00035 | 5 | $7.0 \times 10^{-5}$ | $3.7 \times 10^{-6}$ |
| ΔDEAD | 11.6 | 0.01396 | 5 | $2.8 \times 10^{-3}$ | $2.4 \times 10^{-4}$ |

FIG. 7

Human Dicer 1
GenBank NP_803187
*Homo sapiens*

```
   1 mkspalqpls maglqlmtpa sspmgpffgl pwqqeaihdn iytprkyqve lleaaldhnt
  61 ivclntgsgk tfiavlltke lsyqirgdfs rngkrtvflv nsanqvaqqv savrthsdlk
 121 vgeysnlevn aswtkerwnq eftkhqvlim tcyvalnvlk ngylslsdin llvfdechla
 181 ildhpyreim klcencpscp rilgltasil ngkcdpeele ekiqklekil ksnaetatdl
 241 vvldrytsqp ceivvdcgpf tdrsglyerl lmeleealnf indcnisvhs kerdstlisk
 301 qilsdcravl vvlgpwcadk vagmmvrelq kyikheqeel hrkflllftdt flrkihalce
 361 ehfspasldl kfvtpkvikl leilrkykpy erqqfesvew ynnrnqdnyv swsdseddde
 421 deeieekekp etnfpspftn ilcgiiifver rytavvlnrl ikeagkqdpe layissnfit
 481 ghgigknqpr nkqmeaefrk qeevlrkfra hetnlliats iveegvdipk cnlvvrfdlp
 541 teyrsyvqsk grarapisny imladtdkik sfeedlktyk aiekilrnkc sksvdtgetd
 601 idpvmdddv fppyvlrpdd ggprvtinta ighinrycar lpsdpfthla pkcrtrelpd
 661 gtfystlylp insplrasiv gppmscvrla ervvalicce klhkigeldd hlmpvgketv
 721 kyeeeldlhd eeetsvpgrp gstkrrqcyp kaipeclrds yprpdqpcyl yvigmvlttp
 781 lpdelnfrrr klyppedttr cfgiltakpi pqiphfpvyt rsgevtisie lkksgfmlsl
 841 qmlelitrlh qyifshilrl ekpalefkpt dadsaycvlp lnvvndsstl didfkfmedi
 901 eksearigip stkytketpf vfkledyqda viipryrnfd qphrfyvadv ytdltplskf
 961 pspeyetfae yyktkynldl tnlnqplldv dhtssrlnll avclpsilyr lhcltaeel raqtasdagv
1021 kakweslqnk qilvpelcai hpipaslwrk avclpsilyr lhcltaeel raqtasdagv
1081 gvrslpadfr ypnldfgwkk sidsksfisi snsssaendn yckhstivpe naahgganrt
1141 sslenhdqms vncrtllses pgklhvevsa dltainglsy nqnlangsyd lanrdfcqgn
1201 qlnykqeip vqpttsysiq nlysyenqpq psdectllsn kyldgnanks tsdgspvmav
1261 mpgttdtiqv lkgrmdseqs psigyssrtl gpnpglilqa ltlsnasdgf nlerlemlgd
1321 sflkhaitty lfctypdahe grlsymrskk vsncnlryrlg kkkglpsrmv vsifdppvnw
1381 lppgyvvnqd ksntdkwekd emtkdcmlan gkldedyeee deeeeslmwr apkeeadyed
1441 dfleydqehi rfidnmlmgs gafvkkisls pfsttdsaye wkmpkksslg smpfssdfed
1501 fdysswdamc yldpskavee ddfvvgfwnp seencgvdtg kqsisydlht eqciadksia
1561 dcveallgcy ltscgeraaq lflcslglkv lpvikrtdre kalcptrenf nsqqknlsvs
1621 caaasvassr ssvlkdseyg clkipprcmf dhpdadktln hlisgfenfe kkinyrfknk
1681 ayllqaftha syhyntitdc yqrleflgda ildylitkhl yedprqhspg vltdlrsalv
1741 nntifaslav kydyhkyfka vspelfhvid dfvqfqlekn emggmdselr rseedeekee
1801 dievpkamgd ifeslagaiy mdsgmsletv wqvyypmmrp liekfsanvp rspvrellem
1861 epetakfspa ertydgkvrv tvevvgkkf kgvgrsyria ksaaarralr slkanqpqvp
1921 ns
```

(SEQ ID NO: 1)

DexD/H-box

```
  1 mkspalqpls maglqlmtpa sspmgpffgl pwqqeaihdn iytprkyqve lleaaldhnt
 61 ivclntgsgk tfiavlltke lsyqirgdfs rngkrtvflv nsanqvaqqv savrthsdlk
121 vgeysnlevn aswtkerwnq eftkhqvlim tcyvalnvlk ngylslsdin llvfdechla
181 ildhpyreim klcencpscp rilgltasil ngkcdpeele ekiqklekil ksnaetatdl
241 vvldrytsqp ceivvdcgpf tdrsglyerl lmeleealnf indcnisvhs kerdstlisk
301 qilsdcravl vvlgpwcadk vagmmvrelq kyikheqeel hrkflliftdt flrkihalce
361 ehfspasldl kfvtpkvikl leilrkykpy erqqfesvew ynnrnqdnyv swsdsedde
421 deeieekekp etnfpspftn ilcgiiifver rytavvlnrl ikeagkqdpe layissnfit
481 ghgigknqpr nkqmeaefrk qeevlrkfra hetnlliats iveegvdipk cnlvvrfdlp
541 teyrsyvqsk grarapisny imladtdkik sfeedlktyk aiekilrnkc sksvdtgetd
601 idpv
```

FIG. 8

SEQ ID NO:2

Modified Dicer (ΔDEAD)

```
      mddddv fppyvlrpdd ggprvtinta ighinrycar lpsdpfthla pkcrtrelpd
gtfystlylp insplrasiv gppmscvrla ervvalicce klhkigeldd hlmpvgketv
kyeeeldlhd eeetsvpgrp gstkrrqcyp kaipeclrds yprpdqpcyl yvigmvlttp
lpdelnfrrr klyppedttr cfgiltakpi pqiphfpvyt rsgevtisie lkksgfmlsl
qmlelitrlh qyifshilrl ekpalefkpt dadsaycvlp lnvvndsstl didfkfmedi
eksearigip stkytketpf vfkledyqda viipryrnfd qphrfyvadv ytdltplskf
pspeyetfae yyktkynldl tnlnqplldv dhtssrlnll tprhlnqkgk alplssaekr
kakweslqnk qilvpelcai hpipaslwrk avclpsilyr lhclltaeel raqtasdagv
gvrslpadfr ypnldfgwkk sidsksfisi snsssaendn yckhstivpe naahqganrt
sslenhdqms vncrtllses pgklhvevsa dltainglsy nqnlangsyd lanrdfcqgn
qlnyykqeip vqpttsysiq nlysyenqpq psdectllsn kyldgnanks tsdgspvmav
mpgttdtiqv lkgrmdseqs psigyssrtl gpnpglilqa ltlsnasdgf nlerlemlgd
sflkhaitty lfctypdahe grlsymrskk vsncnlyrlg kkkglpsrmv vsifdppvnw
lppgyvvnqd ksntdkwekd emtkdcmlan gkldedyeee deeeeslmwr apkeeadyed
dfleydqehi rfidnmlmgs gafvkkisls pfsttdsaye wkmpkksslg smpfssdfed
fdysswdamc yldpskavee ddfvvgfwnp seencgvdtg kqsisydlht eqciadksia
dcveallgcy ltscgeraaq lflcslglkv lpvikrtdre kalcptrenf nsqqknlsvs
caaasvassr ssvlkdseyg clkipprcmf dhpdadktln hlisgfenfe kkinyrfknk
ayllqaftha syhyntitdc yqrleflgda ildylitkhl yedprqhspg vltdlrsalv
nntifaslav kydyhkyfka vspelfhvid dfvqfqlekn emqgmdselr rseedeekee
dievpkamgd ifeslagaiy mdsgmsletv wqvyypmmrp liekfsanvp rspvrellem
epetakfspa ertydgkvrv tvevvgkf kgvgrsyria ksaaarralr slkanqpqvp
ns
```

FIG. 9

(SEQ ID NO:3)

Modified Dicer (K70A)

```
   1 mkspalqpls maglqlmtpa sspmgpffgl pwqqeaihdn iytprkyqve lleaaldhnt
  61 ivclntgsga tfiavlltke lsyqirgdfs rngkrtvflv nsanqvaqqv savrthsdlk
 121 vgeysnlevn aswtkerwnq eftkhqvlim tcyvalnvlk ngylslsdin llvfdechla
 181 ildhpyreim klcencpscp riigltasil ngkcdpeele ekiqklekil ksnaetatdl
 241 vvldrytsqp ceivvdcgpf tdrsglyerl lmeleealnf indcnisvhs kerdstlisk
 301 qilsdcravl vvlgpwcadk vagmmvrelq kyikheqeel hrkflftdt flrkihalce
 361 ehfspasldl kfvtpkvikl leilrkykpy erqfesvew ynnrnqdnyv swsdseddde
 421 deeieekekp etnfpspftn ilcgiiifver rytavvlnrl ikeagkqdpe layissnfit
 481 ghgikngpr nkqmeaefrk qeevlrkfra hetnlliats iveegvdipk cnlvvrfdlp
 541 teyrsyvqsk grarapisny imladtdkik sfeedlktyk aiekilrnkc sksvdtgetd
 601 idpvmddddv fppyvlrpdd ggprvtinta ighinrycar lpsdpfthla pkcrtrelpd
 661 gtfystlylp insplrasiv gppmscvrla ervvalicce klhkigeldd hlmpvgketv
 721 kyeeeldlhd eeetsvpgrp gstkrrqcyp kaipeclrds yprpdqpcyl yvigmvlttp
 781 lpdelnfrrr klyppedttr cfgiltakpi pqiphfpvyt rsgevtisie lkksgfmlsl
 841 qmlelitrlh qyifshilrl ekpalefkpt dadsaycvlp lnvvndsstl didfkfmedi
 901 eksearigip stkytketpf vfkledyqda viipyrynfd qphrfyvadv ytdltplskf
 961 pspeyetfae yyktkynldl tnlnqplldv dhtssrlnli tprhlnqkgk alplssaekr
1021 kakweslqnk qilvpelcai hpipaslwrk avclpsilyr lhclltaeel raqtasdagv
1081 gvrslpadfr ypnldfgwkk sidsksfisi snsssaendn yckhstivpe naahgganrt
1141 sslenhdqms vncrtlises pgklhvevsa dltainglsy nqnlangsyd lanrdfcqgn
1201 qlnyykqeip vqpttsysiq nlysyenqpq psdectllsn kyldgnanks tsdgspvmav
1261 mpgttdtiqv lkgrmdseqs psigyssrtl gpnpglilqa ltlsnasdgf nlerlemlgd
1321 sflkhaitty lfctypdahe grlsymrskk vsncnlyrlg kkkglpsrmv vsifdppvnw
1381 lppgyvvnqd ksntdkwekd emtkdcmlan gkldedyeee deeeeslmwr apkeeadyed
1441 dfleydqehi rfidnmlmgs gafvkkisls pfsttdsaye wkmpkksslg smpfssdfed
1501 fdysswdamc yldpskavee ddfvvgfwnp seencgvdtg kqsisydlht eqciadksia
1561 dcveallgcy ltscgeraaq lflcslglkv lpvikrtdre kalcptrenf nsqqknlsvs
1621 caaasvassr ssvlkdseyg clkipprcmf dhpdadktln hlisgfenfe kkinyrfknk
1681 ayllqaftha syhyntitdc yqrleflgda ildylitkhl yedprqhspg vltdlrsalv
1741 nntifaslav kydyhkyfka vspelfhvid dfvqfqlekn emqgmdselr rseedeekee
1801 dievpkamgd ifeslagaiy mdsgmsletv wqvyypmmrp liekfsanvp rspvrellem
1861 epetakfspa ertydgkvrv tvevvgkkf kgvgrsyria ksaaarralr slkanqpqvp
1921 ns
```

(SEQ ID NO:4)

FIG. 10

Dicer amino acid sequence alignment

Sequence 1 – Homo sapiens -- GenBank NP_803187
Sequence 2 – Pan troglodytes -- GenBank XP_001154010
Sequence 3 – Canis familiaris -- GenBank XP_537547
Sequence 4 – Rattus norvegicus -- GenBank XP_001068155
Sequence 5 – Mus musculus -- GenBank EDL18787

```
sequence1    MKSPALQPLSMAGLQLMTPASSPMGPFFGLPWQQEAIHDNIYTPRKYQVELLEAALDHNT    60
sequence2    MKNPALQPLSMAGLQLMTPASSPMGPFFGLPWQQEAIHDNIYTPRKYQVELLEAALDHNT    60
sequence3    MKSPALQPLSMAGLQLMTPASSPMGPFFGLPWQQEAIHDNIYTPRKYQVELLEAALDHNT    60
sequence4    MKSPALQPLSMAGLQLMTPASSPMGPFFGLPWQQEAIHDNIYTPRKYQVELLEAALDHNT    60
sequence5    LKSPALQPLSMAGLQLMTPASSPMGPFFGLPWQQEAIHDNIYTPRKYQVELLEAALDHNT    60
              :*.********************************************************** sequence1    IVCLNTGSGKTFIAVLLTKELSYQIRGDFSRNGKRTVFLVNSANQVAQQVSAVRTHSDLK   120
sequence2    IVCLNTGSGKTFIAVLLTKELSYQIRGDFSRNGKRTVFLVNSANQVAQQVSAVRTHSDLK   120
sequence3    IVCLNTGSGKTFIAVLLTKELSYQIRGDFNRNGKRTVFLVNSANQVAQQVSAVRTHSDLK   120
sequence4    IVCLNTGSGKTFIAVLLTKELAHQIRGDLSPHAKRTVFLVNSANQVAQQVSAVRTHSDLK   120
sequence5    IVCLNTGSGKTFIAVLLTKELAHQIRGDLNPHAKRTVFLVNSANQVAQQVSAVRTHSDLK   120
             *******************::.:  .:: .:.******************** sequence1    VGEYSNLEVNASWTKERWNQEFTKHQVLIMTCYVALNVLKNGYLSLSDINLLVFDECHLA   180
sequence2    VGEYSNLEVNASWTKERWNQEFTKHQVLIMTCYVALNVLKNGYLSLSDINLLVFDECHLA   180
sequence3    VGEYSNLEVNASWTKEKWNQEFTKHQVLVMTCYVALNVLKNGYLSLSDINLLVFDECHLA   180
sequence4    VGEYSNLEVNASWTKERWSQEFTKHQVLIMTCYVALNVLKNGYLSLSDINLLVFDECHLA   180
sequence5    VGEYSDLEVNASWTKERWSQEFTKHQVLIMTCYVALTVLKNGYLSLSDINLLVFDECHLA   180
             *****.:********* *.:********:*******.***********************
```

FIG. 11A

```
sequence1      ILDHPYREIMKLCENCPSCPRILGLTASILNGKCDPEELEEKIQKLEKILKSNAETATDL  240
sequence2      ILDHPYREIMKLCENCPSCPRILGLTASILNGKCDPEELEEKIQKLEKILKSNAETATDL  240
sequence3      ILDHPYREIMKLCENCPSCPRILGLTASILNGKCDPEELEEKIQKLEKILKSNAETATDL  240
sequence4      ILDHPYREIMKLCDSCPSCPRILGLTASILNGKCDPDELEEKIQKLEKILKSGAETATDL  240
sequence5      ILDHPYREIMKLCESCPSCPRILGLTASILNGKCDPEELEEKIQKLERILRSDAETATDL  240
               ***********:.*************************:*:.:*:.******** sequence1      VVLDRYTSQPCEIVVDCGPFTDRSGLYERLLMELEEAALNFINDCNISVHSKERDSTLISK  300
sequence2      VVLDRYTSQPCEIVVDCGPFTDRSGLYERLLMELEEALNFINDCNISVHSKERDSTLISK  300
sequence3      VVLDRYTSQPCEIVVDCGPFTDRSGLYERLLMELEEALNFINDCNISVHSKERDSTLISK  300
sequence4      VVLDRYTSQPCEIVVDCGPFTDRSGLYGRLLVELEEALNFINDCNVSVHSKERDSTLISK  300
sequence5      VVLDRYTSQPCEIVVDCGPFTDRSGLYERLLMELEEALDFINDCNVAVHSKERDSTLISK  300
               ************************* * *:****:::********** sequence1      QILSDCRAVLVVLGPWCADKVAGMMVRELQKYIKHEQEELHRKFLLFTDTFLRKIHALCE  360
sequence2      QILSDCRAVLVVLGPWCADKVAGMMVRELQKYIKHEQEELHRKFLLFTDTFLRKIHALCE  360
sequence3      QILSDCRAVLVVLGPWCADKVAGMMVRELQKYIKHEQEELHRKFLLFTDTFLRKIHALCE  360
sequence4      QILSDCRAVLVVLGPWCADKVAGMMVRELQKYIKHEQEELHRKFLLFTDTLLRKIHALCE  360
sequence5      QILSDCRAVLVVLGPWCADKVAGMMVRELQKYIKHEQEELHRKFLLFTDTFLRKIHALCE  360
               ***********************************************:******* sequence1      EHFSPASLDLKFVTPKVIKLLEILRKYKPYERQQFESVEWYNNRNQDNYVSWSDSEDDDE  420
sequence2      EHFSPASLDLKFVTPKVIKLLEILRKYKPYERQQFESVEWYNNRNQDNYVSWSDSEDDDE  420
sequence3      EHFSPASLDLKFVTPKVIKLLEILRKYKPYERQQFESVEWYNNRNQDNYVSWSDSEDDDE  420
sequence4      EYFSPASLDLKYVTPKVMKLLEILRKYKPYERQQFESVEWYNNRNQDNYVSWSDSEDDDD  420
sequence5      EYFSPASLDLKYVTPKVMKLLEILRKYKPYERQQFESVEWYNNRNQDNYVSWSDSEDDDD  420
               *:*********:*****:******************************************:
```

FIG. 11B

```
sequence1      DEEIEEKEKPETNFPSPFTNILCGIIFVERRYTAVVLNRLIKEAGKQDPELAYISSNFIT   480
sequence2      DEEIEEKEKPETNFPSPFTNILCGIIFVERRYTAVVLNRLIKEAGKQDPELAYISSNFIT   480
sequence3      DEEIEEKEKPETNFPSPFTNILCGIIFVERRYTAVVLNRLIKEAGKQDPELAYISSNFIT   480
sequence4      DEEIEEKEKPETNFPSPFTNILCGIIFVERRYTAVVLNRLIKEAGKQDPELAYISSNFIT   480
sequence5      DEEIEEKEKPETNFPSPFTNILCGIIFVERRYTAVVLNRLIKEAGKQDPELAYISSNFIT   480
               ************************************************************ sequence1      GHGIGKNQPRNKQMEAEFRKQEEVLRKFRAHETNLLIATSIVEEGVDIPKCNLVRFDLP   540
sequence2      GHGIGKNQPRNKQMEAEFRKQEEVLRKFRAHETNLLIATSIVEEGVDIPKCNLVRFDLP   540
sequence3      GHGIGKNQPRNKQMEAEFRKQEEVLRKFRAHETNLLIATSIVEEGVDIPKCNLVRFDLP   540
sequence4      GHGIGKNQPRSKQMEAEFRKQEEVLRKFRAHETNLLIATSVVEEGVDIPKCNLVRFDLP   540
sequence5      GHGIGKNQPRSKQMEAEFRKQEEVLRKFRAHETNLLIATSVVEEGVDIPKCNLVRFDLP   540
               ********.*********************** .**************** sequence1      TEYRSYVQSKGRARAPISNYIMLADTDKIKSFEEDLKTYKAIEKILRNKCSKSVDTGETD   600
sequence2      TEYRSYVQSKGRARAPISNYIMLADTDKIKSFEEDLKTYKAIEKILRNKCSKSVDTGEID   600
sequence3      TEYRSYVQSKGRARAPISNYIMLADTDKIKSFEEDLKTYKAIEKILRNKCSKSVDTGETD   600
sequence4      TEYRSYVQSKGRARAPISNYVMLADTDKIKSFEEDLKTYKAIEKILRNKCSKSVDGAEAD   600
sequence5      TEYRSYVQSKGRARAPISNYVMLADTDKIKSFEEDLKTYKAIEKILRNKCSKSADGAEAD   600
               ******************:**********************************.  .* sequence1      IDPVMDDDDVFPPYVLRPDDGGPRVTINTAIGHINRYCARLPSDPFTHLAPKCRTRELPD   660
sequence2      IDPVMDDDDVFPPYVLRPDDGGPRVTINTAIGHINRYCARLPSDPFTHLAPKCRTRELPD   660
sequence3      IEPVVDDDDVFPPYVLRPDDGGPRVTINTAIGHINRYCARLPSDPFTHLAPKCRTRELPD   660
sequence4      VHAVVDDDAFPPYVLRPDDGGPRVTINTAIGHINRYCARLPSDPFTHLAPKCRTRELPD   660
sequence5      VHAGVDDEDAFPPYVLRPDDGGPRVTINTAIGHINRYCARLPSDPFTHLAPKCRTRELPD   660
               : .  :** :.*************************************************
```

FIG. 11C

```
sequence1   GTFYSTLYLPINSPLRASIVGPPMSCVRLAERVVALICCEKLHKIGELDDHLMPVGKETV  720
sequence2   GTFYSTLYLPINSPLRASIVGPPMSCVRLAERVVALICCEKLHKIGELDDHLMPVGKETV  720
sequence3   GTFYSTLYLPINSPLRASIVGPPMSCVRLAERVVALICCEKLHKIGELDDHLMPVGKETV  720
sequence4   GTFYSTLYLPINSPLRASIVGPPMGCVRLAERVVALICCEKLHKIGELDEHLMPVGKETV  720
sequence5   GTFYSTLYLPINSPLRASIVGPPMDSVRLAERVVALICCEKLHKIGELDEHLMPVGKETV  720
            ********************** .****************** :******* sequence1   KYEEELDLHDEEETSVPGRPGSTKRRQCYPKAIPECLRDSYPRPDQPCYLYVIGMVLTTP  780
sequence2   KYEEELDLHDEEETSVPGRPGSTKRRQCYPKAIPECLRDSYPRPDQPCYLYVIGMVLTTP  780
sequence3   KYEEELDLHDEEETSVPGRPGSTKRRQCYPKAIPECLRDSYPKPDQPCYLYVIGMVLTTP  780
sequence4   KYEEELDLHDEEETSVPGRPGSTKRRQCYPKAIPECLRESYPKPDQPCYLYVIGMVLTTP  780
sequence5   KYEEELDLHDEEETSVPGRPGSTKRRQCYPKAIPECLRESYPKPDQPCYLYVIGMVLTTP  780
            **************************************:*:************** sequence1   LPDELNFRRRKLYPPEDTTRCFGILTAKPIPQIPHFPVYTRSGEVTISIELKKSGFMLSL  840
sequence2   LPDELNFRRRKLYPPEDTTRCFGILTAKPIPQIPHFPVYTRSGEVTISIELKKSGFMLSL  840
sequence3   LPDELNFRRRKLYPPEDTTRCFGILTAKPIPQIPHFPVYTRSGEVTISIELKKSGFTLSL  840
sequence4   LPDELNFRRRKLYPPEDTTRCFGILTAKPIPQIPHFPVYTRSGEVTISIELKKSGFTLSQ  840
sequence5   LPDELNFRRRKLYPPEDTTRCFGILTAKPIPQIPHFPVYTRSGEVTISIELKKSGFTLSQ  840
            ******************************************************** * sequence1   QMLELITRLHQYIFSHILRLEKPALEFKPTDADSAYCVLPLNVVNDSSTLDIDFKFMEDI  900
sequence2   QMLELITRLHQYIFSHILRLEKPALEFKPTDADSAYCVLPLNVVNDSSTLDIDFKFMEDI  900
sequence3   QMLELITRLHQYIFSHILRLEKPALEFKPTDADSAYCVLPLNVVNDSSTLDIDFKFMEDI  900
sequence4   QMLELITRLHQYIFSHILRLEKPALEFQPAGAESAYCVLPLNVVNDSSTLDIDFKFMEDI  900
sequence5   QMLELIVTRLHQYIFSHILRLEKPALEFKPTGAESAYCVLPLNVVNDSGTLDIDFKFMEDI  900
            ****** .*******************:*:.*:**************.***********
```

FIG. 11D

```
sequence1      EKSEARIGIPSTKYTKETPFVFKLEDYQDAVIIPRYRNFDQPHRFYVADVYTDLTPLSKF  960
sequence2      EKSEARIGIPSTKYTKETPFVFKLEDYQDAVIIPRYRNFDQPHRFYVADVYTDLTPLSKF  960
sequence3      EKSEARIGIPSTKYSKETPFVFKLEDYQDAVIIPRYRNFDQPHRFYVADVYTDLTPLSKF  960
sequence4      EKSEARIGIPSTKYSKETPFVFKLEDYQDAVIIPRYRNFDQPHRFYVADVYTDLTPLSKF  960
sequence5      EKSEARIGIPSTKYSKETPFVFKLEDYQDAVIIPRYRNFDQPHRFYVADVYTDLTPLSKF  960
               ************:******************************************** sequence1      PSPEYETFAEYYKTKYNLDLTNLNQPLLDVDHTSSRLNLLTPRHLNQKGKALPLSSAEKR  1020
sequence2      PSPEYETFAEYYKTKYNLDLTNLNQPLLDVDHTSSRLNLLTPRHLNQKGKALPLSSAEKR  1020
sequence3      PSPEYETFAEYYKTKYNLDLTNLNQPLLDVDHTSSRLNLLTPRHLNQKGKALPLSSAEKR  1020
sequence4      PSPEYETFAEYYKTKYNLDLTNLNQPLLDVDHTSSRLNLLTPRHLNQKGKALPLSSAEKR  1020
sequence5      PSPEYETFAEYYKTKYNLDLTNLNQPLLDVDHTSSRLNLLTPRHLNQKGKALPLSSAEKR  1020
               ************************************************************ sequence1      KAKWESLQNKQILVPELCAIHPIPASLWRKAVCLPSILYRLHCLLTAEELRAQTASDAGV  1080
sequence2      KAKWESLQNKQILVPELCAIHPIPASLWRKAVCLPSILYRLHCLLTAEELRAQTASDAGV  1080
sequence3      KAKWESLQNKQILVPELCAIHPIPASLWRKAVCLPSILYRLHCLLTAEELRAQTASDAGV  1080
sequence4      KAKWESLQNKQILVPELCAIHPIPASLWRKAVCLPSILYRLHCLLTAEELRAQTASDAGV  1080
sequence5      KAKWESLQNKQILVPELCAIHPIPASLWRKAVCLPSILYRLHCLLTAEELRAQTASDAGV  1080
               ************************************************************ sequence1      GVRSLPADFRYPNLDFGWKKSIDSKSFISISNSSSAENDNYCKHSTIVP-ENAAHQGANR  1139
sequence2      GVRSLPADFRYPNLDFGWKKSIDSKSFISISNSSSAENDNYCKHSTIVP-ENAAHQGANR  1139
sequence3      GVRSLPVDFRYPNLDFGWKKSIDSKSFISISNSSSAENENYCKHSTIVVPENAARQGANR  1140
sequence4      GVRSLPADFRYPNLDFGWKKSIDSKSFISVANSSSAENENYCKHSTIVVPENAARQGANR  1140
sequence5      GVRSLPVDFRYPNLDFGWKKSIDSKSFISSCNSSLAESDNYCKHSTTVVPENAAHQGATR  1140
               ******.**********************   .***:**:******* .*.::***:.*
```

FIG. 11E

| | | |
|---|---|---|
| sequence1 | TSSLENHDQMSVNCRTLLSESPGKLHVEVSADLTAINGLSYNQNLANGSYDLANRDFCQG | 1199 |
| sequence2 | TSSLENHDQMSVNCRTLLSESPGKLHVEVSADLTAINGLSYNQNLANGSYDLANRDFCQG | 1199 |
| sequence3 | TSSLENHDQMSVNCRTLFSESPGKLHVEVSADLTAINGLSYNKNLANGSYDLANRDFCQG | 1200 |
| sequence4 | P-SLENHDQMSVNCKRLPAESPAKLQSEVSVDLTAINGLSYNKSLANGSYDLVNRDFCQG | 1199 |
| sequence5 | P-SLENHDQMSVNCKRLPAESPAKLQSEVSTDLTAINGLSYNKNLANGSYDLVNRDFCQG | 1199 |
| | . *******: *:****** *******:*:***:**** | |
| sequence1 | NQLNYYKQEIPVQPTTSYIQNLYSYENQPQPSDECTLLSNKYLDGNANKSTSDGSPVMA | 1259 |
| sequence2 | NQLNYYKQEIPVQPTTSYIQNLYSYENQPQPSDECTLLSNKYLDGNANKSTSDGSPVMA | 1259 |
| sequence3 | NQLNYYKQEIPVQPTTSYPIQNLYNYENQPKPSDECTLLSNKYLDGNANKSTSDGSPTTA | 1260 |
| sequence4 | NQLTYFKQEIPVQPTTSYPIQNLYNYENQPTPSNECPLLSNKYLDGNANTSTSDGSPAGS | 1259 |
| sequence5 | NQLNYFKQEIPVQPTTSYPIQNLYNYENQPKPSNECPLLSNTYLDGNANTSTSDGSPAVS | 1259 |
| | * :******** **.*.. .*..****. . | |
| sequence1 | VMPGTTDTIQVLKGRMDSEQSPSIGYSSRTLGPNPGLILQALTLSNASDGFNLERLEMLG | 1319 |
| sequence2 | VMPGTTDTIQVLKGRMDSEQSPSIGYSSRTLGPNPGLILQALTLSNASDGFNLERLEMLG | 1319 |
| sequence3 | AMPGTTEAVRALKDKMGSEQSPCPGYSSRTLGPNPGLILQALTLSNASDGFNLERLEMLG | 1320 |
| sequence4 | PRPAMMTAVEALEGRTDSEQSPSVGHSSRTLGPNPGLILQALTLSNASDGFNLERLEMLG | 1319 |
| sequence5 | TMPAMMNAVKALKDRMDSEQSPSVGYSSRTLGPNPGLILQALTLSNASDGFNLERLEMLG | 1319 |
| | *. ::.:*:. .: .***** *:*********************************** | |
| sequence1 | DSFLKHAITTYLFCTYPDAHEGRLSYMRSKKVSNCNLYRLGKKKGLPSRMVVSIFDPPVN | 1379 |
| sequence2 | DSFLKHAITTYLFCTYPDAHEGRLSYMRSKKVSNCNLYRLGKKKGLPSRMVVSIFDPPVN | 1379 |
| sequence3 | DSFLKHAITTYLFCTYPDAHEGRLSYMRSKKVSNCNLYRLGKKKGLPSRMVVSIFDPPVN | 1380 |
| sequence4 | DSFLKHAITTYLFCTYPDAHEGRLSYMRSKKVSNCNLYRLGKKQGLPSRMVVSIFDPPVN | 1379 |
| sequence5 | DSFLKHAITTYLFCTYPDAHEGRLSYMRSKKVSNCNLYRLGKKKGLPSRMVVSIFDPPVN | 1379 |
| | **********************************************:******* | |

FIG. 11F

```
sequence1    WLPPGYVVVNQDKSNTDKWEKDEMTKDCMLANGKLDEDYEEEDEEEESLMWRAPKEEADYE   1439
sequence2    WLPPGYVVVNQDKSNTDKWEKDEMTKDCMLANGKLDEDYEEEDEEEESLMWRAPKEEADYE   1439
sequence3    WLPPGYVVVNQDKSNADKWEKDEMTKDCMLANGKLDEDFEEDDEEEDLMWRAPKEDADYE    1440
sequence4    WLPPGYVVVNQDKSNSEKWEKDEMTKDCLLANGKLGEDCE--EEEEELAWRAPKEEAEYE    1437
sequence5    WLPPGYVVVNQDKSNSEKWEKDEMTKDCLLANGKLGEACE--EEE--DLTWRAPKEEAEDE   1435
             *********:*:*******:*.:******** :* *  :**  * ******:* * sequence1    DDFLEYDQEHIRFIDNMLMGSGAFVKKISLSPFSTTDSAYEWKMPKKSSLGSMPFSSDFE    1499
sequence2    DDFLEYDQEHIRFIDNMLMGSGAFVKKISLSPFSTTDSAYEWKMPKKSSLGSMPFSSDFE    1499
sequence3    DDFLEYDQEHIKFIDNMLMGSGAFVKKISLSPFSTTDSAYEWKMPKKSSLGSMPFSSDFE    1500
sequence4    DDLLEYDQEHIQFIDSMLMGSGAFVKKIPLSPFSTSDSAYEWKMPKKASLGSVPFSSDLE    1497
sequence5    DDFLEYDQEHIQFIDSMLMGSGAFVRKISLSPFSASDSAYEWKMPKKASLGSMPFASGLE    1495
             ** :*******::***.********:**.*****::.*********::***:**:*..**

sequence1    DFDYSSWDAMCYLDPSKAVEEDDFVVGFWNPSEENCGVDTGKQSISYDLHTEQCIADKSI    1559
sequence2    DFDYSSWDAMCYLDPSKAVEEDDFVVGFWNPSEENCGVDTGKQSISYDLHTEQCIADKSI    1559
sequence3    DFDYSSWDAMCYLDPSKAVEEDDFVVGFWNPSEENCGVDTGKQSISYDLHTEQCIADKSI    1560
sequence4    DFDYSSWDAMCYLDPSKAVEEDDFVVGFWNPSEENCGVDTGKQSISYDLHTEQCIADKSI    1557
sequence5    DFDYSSWDAMCYLDPSKAVEEDDFVVGFWNPSEENCGVDTGKQSISYDLHTEQCIADKSI    1555
             ************************************************************ sequence1    ADCVEALLGCYLTSCGERAAQLFLCSLGLKVLPVIKRTDREKALCPTRENFNSQQKNLSV    1619
sequence2    ADCVEALLGCYLTSCGERAAQLFLCSLGLKVLPVIKRTDREKALCPTRENFNSQQKNLSV    1619
sequence3    ADCVEALLGCYLTSCGERAAQLFLCSLGLKVLPVMKRTDREKTMCPPRENFSSQQKNLSG    1620
sequence4    ADCVEALLGCYLTSCGERAAQLFLCSLGLKVLPVIKRTSRDKASYPAQENSSSQQKSPSG    1617
sequence5    ADCVEALLGCYLTSCGERAAQLFLCSLGLKVLPVIKRTSREKALDPAQENGSSQQKSLSG    1615
             **********************************:***.*:**  .*:**:.***. *.
```

FIG. 11G

| | | |
|---|---|---|
| sequence1 | SCAAASVASSRSSVLKDSEYGCLKIPPRCMFDHPDADKTLNHLISGFENFEKKINYRFKN | 1679 |
| sequence2 | SCAAASVASSRSSVLKDSEYGCLKIPPRCMFDHPDADKTLNHLISGFENFEKKINYRFKN | 1679 |
| sequence3 | GRAAASVASLRPSVLKDLEYGCLKIPPRCMFDHPDADKTLNHLISGFENFEKKINYRFKN | 1680 |
| sequence4 | SCAAA--VSPRSSAGKDLEYGCLKIPPRCMFDHPDAEKTLNHLISGFENFEKKINYIFKN | 1675 |
| sequence5 | SCASP--VGPRSSAGKDLEYGCLKIPPRCMFDHPDAEKTLNHLISGFETFEKKINYRFKN | 1673 |
| | .*:.. .*  ***********::*.*******.**:* |  |
| sequence1 | KAYLLQAFTHASYHYNTITDCYQRLEFLGDAILDYLITKHLYEDPRQHSPGVLTDLRSAL | 1739 |
| sequence2 | KAYLLQAFTHASYHYNTITDCYQRLEFLGDAILDYLITKHLYEDPRQHSPGVLTDLRSAL | 1739 |
| sequence3 | KAYLLQAFTHASYHYNTITDCYQRLEFLGDAILDYLITKHLYEDPRQHSPGVLTDLRSAL | 1740 |
| sequence4 | KAYLLQAFTHASYHYNTITDCYQRLEFLGDAILDYLITKHLYEDPRQHSPGVLTDLRSAL | 1735 |
| sequence5 | KAYLLQAFTHASYHYNTITDCYQRLEFLGDAILDYLITKHLYEDPRQHSPGVLTDLRSAL | 1733 |
| | ************************************************************ |  |
| sequence1 | VNNTIFASLAVKYDYHKYFKAVSPELFHVIDDFVQFQLEKNEMQGMDSELRRSEEDEEKE | 1799 |
| sequence2 | VNNTIFASLAVKYDYHKYFKAVSPELFHVIDDFVQFQLEKNEMQGMDSELRRSEEDEEKE | 1799 |
| sequence3 | VNNTIFASLAVKYDYHKYFKAVSPELFHVIDDFVQFQLEKNEMQGMDSELRRSEEDEEKE | 1800 |
| sequence4 | VNNTIFASLAVKYDYHKYFKAVSPELFHVIDDFVQFQLEKNEMQGMDSELRRSEEDEEKE | 1795 |
| sequence5 | VNNTIFASLAVKYDYHKYFKAVSPELFHVIDDFVKFQLEKNEMQGMDSELRRSEEDEEKE | 1793 |
| | ******************************:*********************** |  |
| sequence1 | EDIEVPKAMGDIFESLAGAIYMDSGMSLETVWQVYYPMMRPLIEKFSANVPRSPVRELLE | 1859 |
| sequence2 | EDIEVPKAMGDIFESLAGAIYMDSGMSLETVWQVYYPMMRPLIEKFSANVPRSPVRELLE | 1859 |
| sequence3 | EDIEVPKAMGDIFESLAGAIYMDSGMSLEMVWQVYYPMMRPLIEKFSANVPRSPVRELLE | 1860 |
| sequence4 | EDIEVPKAMGDIFESLAGAIYMDSGMSLEVVWQVYYPMMRPLIEKFSANVPRSPVRELLE | 1855 |
| sequence5 | EDIEVPKAMGDIFESLAGAIYMDSGMSLEVVWQVYYPMMQPLIEKFSANVPRSPVRELLE | 1853 |
| | ***************************  ***:***************** |  |

FIG. 11H

```
sequence1  MEPETAKFSPAERTYDGKVRVRTVEVVGKGKFKGVGRSYRIAKSAAARRALRSLKANQPQV  1919
sequence2  MEPETAKFSPAERTYDGKVRVRTVEVVGKGKFKGVGRSYRIAKSAAARRALRSLKANQPQL  1919
sequence3  MEPETAKFSPAERTYDGKVRVRTVEVVGKGKFKGVGRSYRIAKSAAARRALRSLKANQPQV  1920
sequence4  MEPETAKFSPAERTYDGKVRVRTVEVVGKGKFKGVGRSYRIAKSAAARRALRSLKANQPLV  1915
sequence5  MEPETAKFSPAERTYDGKVRVRTVEVVGKGKFKGVGRSYRIAKSAAARRALRSLKANQPQV  1913
           ************************************************************ :

sequence1  PNS-------  1922
sequence2  WVSLALPSTYQ 1930
sequence3  PNS-------  1923
sequence4  PNS-------  1918
sequence5  PNS-------  1916
           *
```

FIG. 11I

MODIFIED DICER POLYPEPTIDE AND METHODS OF USE THEREOF

CROSS-REFERENCE

This application claims the benefit of U.S. Provisional Patent Application No. 61/070,286, filed Mar. 21, 2008, which application is incorporated herein by reference in its entirety.

STATEMENT REGARDING FEDERALLY SPONSORED RESEARCH

This invention was made with government support under Grant No. R01-GM073794 awarded by the National Institutes of Health. The government has certain rights in the invention.

BACKGROUND

Dicer is a large multi-domain enzyme responsible for cytoplasmic production of both microRNAs (miRNAs) and short interfering RNAs (siRNAs) during sequence-directed gene regulation by RNAi. As a member of the Ribonuclease III family of proteins, Dicer recognizes the 5' and 3' helical ends of double-stranded RNA substrates and cleaves a specific distance away to produce 21-27 nucleotide products. Dicer helps these mi- and siRNAs to load onto Argonaute proteins together with other protein components of the RNA-induced silencing complex (RISC). Once bound to target mRNAs, miRNAs typically regulate protein expression by controlling the level of translation, whereas siRNAs direct cleavage and subsequent degradation of complementary mRNAs.

Production of siRNAs is useful in various research and therapeutic applications. There is a need in the art for an enzyme that efficiently generates siRNAs from a double-stranded RNA substrate.

LITERATURE

U.S. Patent Publication No. 2007/0031417; U.S. Patent Publication No. 2003/0224432; WO 03/093430; MacRae and Doudna (2007) *Curr. Opin. Struct. Biol.* 17:138;

SUMMARY OF THE INVENTION

A modified Dicer polypeptide is provided, which modified Dicer polypeptide exhibits enhanced catalytic activity. Also provided is a method for producing a small regulator RNA from a dsRNA, involving contacting a dsRNA with a subject modified Dicer. Small regulatory RNAs produced by a subject method find use in a variety of applications, including research and therapeutic applications.

BRIEF DESCRIPTION OF THE DRAWINGS

FIGS. 1A-C depict domain structures and expression of human Dicer proteins.

FIG. 2A provides nucleotide sequences of 37ab double-stranded RNA substrate (upper sequence: SEQ ID NO:5; lower sequence: SEQ ID NO:6); and a nucleotide sequence of pre-hlet-7 (SEQ ID NO:7).

FIGS. 3A-C depict binding affinity of Dicer proteins to duplex RNAs.

FIG. 7 depicts the amino acid sequence of a wild-type human Dicer polypeptide.

FIG. 8 depicts an amino acid sequence of a DExD/H-box domain.

FIG. 9 depicts the amino acid sequence of an exemplary modified Dicer polypeptide, which lacks a DExD/H-box domain.

FIG. 10 depicts the amino acid sequence of an exemplary modified Dicer polypeptide, which has a single amino acid substitution in the DExD/H-box domain.

FIGS. 11A-I depict an amino acid sequence alignment of Dicer polypeptides from various mammalian species. Sequence 1: SEQ ID NO:1; Sequence 2: SEQ ID NO:21; Sequence 3: SEQ ID NO:22; Sequence 4: SEQ ID NO:23; Sequence 5: SEQ ID NO:24.

DEFINITIONS

Figure 2A:
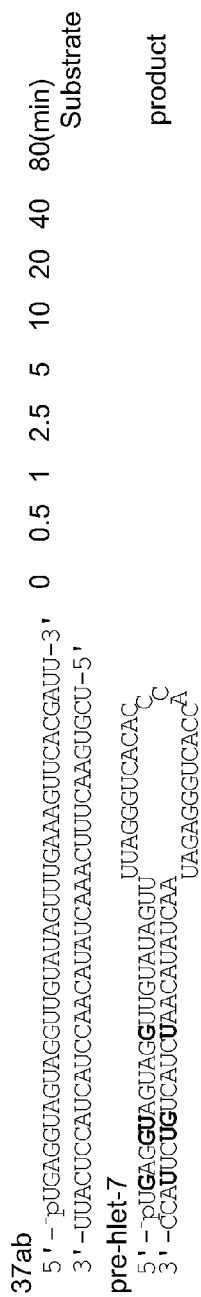
FIGS. 2A-D depict single-turnover activity of Dicer proteins.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' terminus and a translation stop codon at the 3' terminus. A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule or between two separate RNA molecules. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure.

In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

MicroRNAs (miRNAs) are encoded by genes, which encode transcripts containing short double-stranded RNA hairpins. mRNAs are transcribed as longer precursors, termed pre-miRNAs, which can be 50 to 80 nucleotides in length, and which are sometimes found in clusters and frequently found in introns. Upon transcription, miRNAs undergo nuclear cleavage by an RNase III endonuclease, producing the 60-70-nt stem-loop precursor miRNA (pre-miRNA) with a 5' phosphate and a 2-nt 3 overhang. The pre-miRNAs are cleaved by Dicer about two helical turns away from the ends of the pre-miRNA stem loop, producing double-stranded RNA with strands that are approximately the same length (21 to 24 nucleotides), and possess the characteristic 5'-phosphate and 3'-hydroxyl termini. One of the strands of this short-lived intermediate accumulates as the mature miRNA and is subsequently incorporated into a ribonucleoprotein complex, the miRNP. mRNAs interact with target RNAs at specific sites to induce cleavage of the message or inhibit translation.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

The term "heterologous," as used herein in the context of a genetically modified host cell, refers to a polypeptide wherein at least one of the following is true: (a) the polypeptide is foreign ("exogenous") to (i.e., not naturally found in) the host cell; (b) the polypeptide is naturally found in (e.g., is "endogenous to") a given host microorganism or host cell but is either produced in an unnatural (e.g., greater than expected or greater than naturally found) amount in the cell, or differs in nucleotide sequence from the endogenous nucleotide sequence such that the same encoded protein (having the same or substantially the same amino acid sequence) as found endogenously is produced in an unnatural (e.g., greater than expected or greater than naturally found) amount in the cell.

The term "heterologous," as used herein in the context of a chimeric polypeptide, refers to two components that are defined by structures derived from different sources. For example, where "heterologous" is used in the context of a chimeric polypeptide (e.g., a chimeric modified Dicer enzyme), the chimeric polypeptide includes operably linked amino acid sequences that can be derived from different polypeptides (e.g., a first amino acid sequence from modified Dicer enzyme; and a second amino acid sequence other than a modified Dicer enzyme). Similarly, "heterologous" in the context of a polynucleotide encoding a chimeric polypeptide includes operably linked nucleotide sequences that can be derived from different coding regions (e.g., a first nucleotide sequence encoding a modified Dicer enzyme; and a second nucleotide sequence encoding a polypeptide other than a modified Dicer enzyme).

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a modified Dicer polypeptide" includes a plurality of such polypeptide and reference to "the siRNA" includes reference to one or more siRNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

A modified Dicer polypeptide is provided, which modified Dicer polypeptide exhibits enhanced catalytic activity. Also provided is a method for producing small regulator RNAs (e.g., siRNAs and miRNAs) from a dsRNA, involving contacting a dsRNA with a subject modified Dicer. siRNAs and miRNAs produced by a subject method find use in a variety of applications, including research and therapeutic applications.

Modified Dicer Polypeptides

The present invention provides modified Dicer polypeptides. A subject modified Dicer polypeptide exhibits enhanced catalytic activity, i.e., exhibits enhanced double-stranded RNA (dsRNA) endonuclease activity, compared an unmodified Dicer polypeptide, e.g., compared to a naturally-occurring Dicer polypeptide.

In some embodiments, the $k_{cat}$ of a subject modified Dicer polypeptide is higher than the $k_{cat}$ of an unmodified Dicer polypeptide. $k_{cat}$ is the turnover number (i.e., the number of times an enzyme active site converts substrate to product per unit time), and is expressed as an inverse time unit. In some embodiments, the $K_m$ of a subject modified Dicer polypeptide is lower than the $K_m$ of an unmodified Dicer polypeptide. $K_m$ is the Michaelis-Menten constant, i.e., the substrate concentration needed to achieve a half-maximum enzyme velocity. In some embodiments, the efficiency of a subject modified Dicer polypeptide is greater than the efficiency of an unmodified Dicer polypeptide, where efficiency is expressed as $k_{cat}$ divided by $K_m$, or $k_{cat} \times K_m^{-1}$.

In some embodiments, the $k_{cat}$ of a subject modified Dicer polypeptide is higher than the $k_{cat}$ of an unmodified Dicer, e.g., the $k_{cat}$ of a subject modified Dicer polypeptide is at least about 25%, at least about 50%, at least about 100% (or 2-fold), at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 80-fold, at least about 90-fold, or at least about 100-fold, or more than 100-fold, higher than the $k_{cat}$ of an unmodified Dicer.

In some embodiments, the $k_{cat}$ of a subject modified Dicer polypeptide is higher than the $k_{cat}$ of an unmodified Dicer, e.g., the $k_{cat}$ of a subject modified Dicer polypeptide is from about 25% higher to about 50% higher, from about 50% higher to about 2-fold higher to about 5-fold higher, from about 5-fold higher to about 10-fold higher, from about 10-fold higher to about 15-fold higher, from about 15-fold higher to about 20-fold higher, from about 20-fold higher to about 25-fold higher, from about 25-fold higher to about 30-fold higher, from about 30-fold higher to about 40-fold higher, from about 40-fold higher to about 50-fold higher, from about 50-fold higher to about 60-fold higher, from about 60-fold higher to about 70-fold higher, from about 70-fold higher to about 80-fold higher, from about 80-fold higher to about 90-fold higher, from about 90-fold higher to about 100-fold higher, or more than 100-fold higher, than the $k_{cat}$ of an unmodified Dicer.

For example, in some embodiments, the $k_{cat}$ of a subject modified Dicer polypeptide is higher than the $k_{cat}$ of a Dicer polypeptide having the amino acid sequence depicted in FIG. 7 and set forth in SEQ ID NO:1, e.g., the $k_{cat}$ of a subject modified Dicer polypeptide is from about 25% higher to about 50% higher, from about 50% higher to about 2-fold higher to about 5-fold higher, from about 5-fold higher to about 10-fold higher, from about 10-fold higher to about 15-fold higher, from about 15-fold higher to about 20-fold higher, from about 20-fold higher to about 25-fold higher, from about 25-fold higher to about 30-fold higher, from about 30-fold higher to about 40-fold higher, from about 40-fold higher to about 50-fold higher, from about 50-fold higher to about 60-fold higher, from about 60-fold higher to about 70-fold higher, from about 70-fold higher to about 80-fold higher, from about 80-fold higher to about 90-fold higher, from about 90-fold higher to about 100-fold higher, or more than 100-fold higher, than the $k_{cat}$ of a Dicer polypeptide having the amino acid sequence depicted in FIG. 7 and set forth in SEQ ID NO:1.

To measure $k_{cat}$, any suitable double-stranded RNA substrate can be used. As one non-limiting example, a double-stranded RNA of the following sequence can be used:

```
                                              (SEQ ID NO: 5)
5'-UGAGGUAGUAGGUUGUAUAGUUUGAAAGUUCACGAUU-3'

(SEQ ID NO: 6)
3'-UUACUCCAUCAUCCAACAUAUCAAACUUUCAAGUGCU-5'
``` where the two sequences form a double-stranded RNA. This double-stranded RNA (dsRNA) is referred to in the Examples as "37ab."

Thus, for example, in some embodiments, the $k_{cat}$ of a subject modified Dicer polypeptide is higher than the $k_{cat}$ of a Dicer polypeptide having the amino acid sequence depicted in FIG. 7 and set forth in SEQ ID NO:1, e.g., the $k_{cat}$ of a subject modified Dicer polypeptide is from about 25% higher to about 50% higher, from about 50% higher to about 2-fold higher to about 5-fold higher, from about 5-fold higher to about 10-fold higher, from about 10-fold higher to about 15-fold higher, from about 15-fold higher to about 20-fold higher, from about 20-fold higher to about 25-fold higher, from about 25-fold higher to about 30-fold higher, from about 30-fold higher to about 40-fold higher, from about 40-fold higher to about 50-fold higher, from about 50-fold higher to about 60-fold higher, from about 60-fold higher to about 70-fold higher, from about 70-fold higher to about 80-fold higher, from about 80-fold higher to about 90-fold higher, from about 90-fold higher to about 100-fold higher, or more than 100-fold higher, than the $k_{cat}$ of a Dicer polypeptide having the amino acid sequence depicted in FIG. 7 and set forth in SEQ ID NO:1, when the 37ab dsRNA is used as a substrate.

In some embodiments, the $k_{cat}$ of a subject modified Dicer is from about $0.5 \times 10^{-1}$ s$^{-1}$ to about $1 \times 10^{-5}$ s$^{-1}$, e.g., from about $0.5 \times 10^{-1}$ s$^{-1}$ to about $1 \times 10^{-1}$ s$^{-1}$, from about $1 \times 10^{-1}$ s$^{-1}$ to about $5 \times 10^{-1}$ s$^{-1}$, from about $5 \times 10^{-1}$ s$^{-1}$ to about $1 \times 10^{-2}$ s$^{-1}$, from about $1 \times 10^{-2}$ s$^{-1}$ to about $5 \times 10^{-2}$ s$^{-1}$, from about $5 \times 10^{-2}$ s$^{-1}$ to about $1 \times 10^{-3}$ s$^{-1}$, from about $1 \times 10^{-3}$ s$^{-1}$ to about $5 \times 10^{4}$ s$^{-1}$, or from about $5 \times 10^{4}$ s$^{-1}$ to about $10^{-5}$ s$^{-1}$.

In some embodiments, the $K_m$ of a subject modified Dicer polypeptide for a dsRNA substrate is lower than the $K_m$ of an unmodified Dicer polypeptide for the same dsRNA substrate, e.g., in some embodiments, the $K_m$ of a subject modified Dicer polypeptide for a dsRNA substrate is at least about 10% lower, at least about 15% lower, at least about 20% lower, at least about 25% lower, at least about 30% lower, at least about 35% lower, at least about 40% lower, at least about 45% lower, at least about 50% lower, at least about 60% lower, at least about 70% lower, at least about 80% lower, or at least about 90% lower, than the $K_m$ of an unmodified Dicer polypeptide. In some embodiments, the $K_m$ of a subject modified Dicer polypeptide for a dsRNA substrate is lower than the $K_m$ of a Dicer polypeptide having the amino acid sequence depicted in FIG. 7 and set forth in SEQ ID NO:1, for the same dsRNA substrate, e.g., the $K_m$ of a subject modified Dicer polypeptide for a dsRNA substrate is at least about 10% lower, at least about 15% lower, at least about 20% lower, at least about 25% lower, at least about 30% lower, at least about 35% lower, at least about 40% lower, at least about 45% lower, at least about 50% lower, at least about 60% lower, at least about 70% lower, at least about 80% lower, or at least about 90% lower, than the $K_m$ of a Dicer polypeptide having the amino acid sequence depicted in FIG. 7 and set forth in SEQ ID NO:1, for the same dsRNA substrate.

In some embodiments, the enzyme efficiency (the ratio of $k_{cat}$ to $K_m$) of a subject modified Dicer polypeptide for processing a dsRNA substrate is greater than the efficiency of an unmodified Dicer polypeptide, e.g., the efficiency of a subject modified Dicer polypeptide is at least about 5-fold, at least about 7-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 100-fold, at least about 110-fold, at least about 120-fold, at least about 130-fold, at least about 140-fold, at least about 150-fold, at least about 160-fold, at least about 170-fold, at least about 180-fold, at least about 190-fold, at least about 200-fold, or more than 200-fold, greater than the efficiency of an unmodified Dicer polypeptide in processing the same substrate.

In some embodiments, the enzyme efficiency of a subject modified Dicer polypeptide for processing a dsRNA substrate is greater than the efficiency of a Dicer polypeptide having the amino acid sequence depicted in FIG. 7 and set forth in SEQ ID NO:1, e.g., the enzyme efficiency of a subject modified Dicer polypeptide for processing a dsRNA substrate is at least about 5-fold, at least about 7-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 100-fold, at least about 110-fold, at least about 120-fold, at least about 130-fold, at least about 140-fold, at least about 150-fold, at least about 160-fold, at least about 170-fold, at least about 180-fold, at least about 190-fold, at least about 200-fold, or more than 200-fold, greater than the efficiency of a Dicer polypeptide having the amino acid sequence depicted in FIG. 7 and set forth in SEQ ID NO:1 for processing the same dsRNA substrate.

In some embodiments, the enzyme efficiency of a subject modified Dicer polypeptide for processing the 37ab dsRNA substrate shown above is greater than the efficiency of a Dicer polypeptide having the amino acid sequence depicted in FIG. 7 and set forth in SEQ ID NO:1, e.g., the enzyme efficiency of a subject modified Dicer polypeptide for processing a dsRNA substrate is at least about 5-fold, at least about 7-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 100-fold, at least about 110-fold, at least about 120-fold, at least about 130-fold, at least about 140-fold, at least about 150-fold, at least about 160-fold, at least about 170-fold, at least about 180-fold, at least about 190-fold, at least about 200-fold, or more than 200-fold, greater than the efficiency of a Dicer polypeptide having the amino acid sequence depicted in FIG. 7 and set forth in SEQ ID NO:1 for processing the 37ab dsRNA substrate.

In some embodiments, a subject modified Dicer polypeptide lacks all or a portion of a DExD/H-box helicase domain The DExD/H-box helicase domain is an N-terminal domain found in many Dicer proteins, and is typically about 600 amino acids in length. In some embodiments, a subject modified Dicer polypeptide lacks from about 200 amino acids to about 250 amino acids, from about 250 amino acids to about 300 amino acids, from about 300 amino acids to about 350 amino acids, from about 350 amino acids to about 400 amino acids, from about 400 amino acids to about 450 amino acids, from about 450 amino acids to about 500 amino acids, from about 500 amino acids to about 550 amino acids, or from about 550 amino acids to about 600 amino acids of a DExD/H-box helicase domain. An exemplary DExD/H-box amino acid sequence is depicted in FIG. 8 (SEQ ID NO:2).

In some embodiments, a subject modified Dicer polypeptide lacks all or a portion of a DExD/H-box helicase domain, and comprises, in addition to two ribonuclease domains, a double-stranded RNA binding domain (dsRBD), a domain of unknown function ("DUF283") domain, and a PAZ domain.

In some embodiments, a subject modified Dicer polypeptide has a length of from about 1100 amino acids to about 1150 amino acids, from about 1150 amino acids to about 1200 amino acids, from about 1200 amino acids to about 1250 amino acids, from about 1250 amino acids to about 1300 amino acids, from about 1300 amino acids to about 1325 amino acids, from about 1325 amino acids to about 1350 amino acids, from about 1350 amino acids to about 1375 amino acids, from about 1375 amino acids to about 1400 amino acids, from about 1400 amino acids to about 1425 amino acids, from about 1425 amino acids to about 1450 amino acids, from about 1450 amino acids to about 1475 amino acids, from about 1475 amino acids to about 1500 amino acids, from about 1500 amino acids to about 1525 amino acids, from about 1525 amino acids to about 1550 amino acids, from about 1550 amino acids to about 1575 amino acids, from about 1575 amino acids to about 1600 amino acids, from about 1600 amino acids to about 1625 amino acids, from about 1625 amino acids to about 1650 amino acids, from about 1650 amino acids to about 1675 amino acids, or from about 1675 amino acids to about 1700 amino acids.

The amino acid sequence of an exemplary modified Dicer polypeptide is depicted in FIG. 9. In some embodiments, a subject modified Dicer polypeptide: 1) lacks all or a portion of a DExD/H-box helicase domain; 2) has a length of from about 1100 amino acids to about 1150 amino acids, from about 1150 amino acids to about 1200 amino acids, from about 1200 amino acids to about 1250 amino acids, from about 1250 amino acids to about 1300 amino acids, from about 1300 amino acids to about 1320 amino acids; and 3) comprises an amino acid sequence having at least about 75%, at least about at least about 80%, at least about 85%, at least about 90%, at least about 95%, at least about 98%, or at least about 99%, amino acid sequence identity to a contiguous stretch of from about 1100 amino acids to about 1150 amino acids, from about 1150 amino acids to about 1200 amino acids, from about 1200 amino acids to about 1250 amino acids, from about 1250 amino acids to about 1300 amino acids, or from about 1300 amino acids to 1318 amino acids, of the amino acid sequence depicted in FIG. 9 (SEQ ID NO:3).

In some embodiments, a subject modified Dicer polypeptide comprises one or more amino acid substitutions, insertions, or deletions in the DExD/H-box domain (e.g., within amino acids 1 to about 604 of the amino acid sequence depicted in FIG. 7, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$). In some embodiments, a subject modified Dicer polypeptide comprises one or more amino acid substitutions, insertions, or deletions in the DExD/H-box domain (e.g., within amino acids 63 to 71 of the amino acid sequence depicted in FIG. 7, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$). In some embodiments, a subject modified Dicer polypeptide comprises one or more amino acid substitutions, insertions, or deletions in the DExD/H-box domain (e.g., within amino acids 175 to 178 of the amino acid sequence depicted in FIG. 7, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$).

In some embodiments, a subject modified Dicer polypeptide comprises one or more amino acid substitutions in the DExD/H-box domain (e.g., within amino acids 1 to about 604 of the amino acid sequence depicted in FIG. 7, and as set forth in SEQ ID NO:1, where the one or more amino acid substitutions results in enhanced enzymatic activity (e.g., one or more of increased $k_{cat}$, decreased $K_m$, and increased $k_{cat} \times K_m^{-1}$).

As one non-limiting example, in some embodiments, a subject modified Dicer polypeptide comprises a K70A substitution in the DExD/H-box domain (e.g., within amino acids 1 to about 604 of the amino acid sequence depicted in FIG. 7, and as set forth in SEQ ID NO:1), or a K70A substitution at a corresponding amino acid position, compared to a Dicer polypeptide from a species other than human. For example, in some embodiments, a subject modified Dicer polypeptide: a) comprises a K70A substitution in the DExD/H-box domain, as shown in FIG. 10; b) shares at least about 75%, at least about 80%, at least about 85%, at least about 90%, at least about 95%, at least about 98%, or 100%, amino acid sequence identity over a contiguous stretch of from about 1600 amino acids to about 1700 amino acids, from about 1700 amino acids to about 1800 amino acids, or from about 1800 amino acids to about 1921 amino acids, of the amino acid sequence depicted in FIG. 10 and set forth in SEQ ID NO:4; and c) enhanced enzymatic activity (e.g., one or more of increased $k_{cat}$, decreased $K_m$, and increased $k_{cat} \times K_m^{-1}$) compared to a Dicer polypeptide comprising the amino acid sequence depicted in FIG. 7 and set forth in SEQ ID NO:1.

In some embodiments, a subject modified Dicer polypeptide comprises a K70A substitution in the DExD/H-box domain (e.g., within amino acids 1 to 604 of the amino acid sequence depicted in FIG. 7, and as set forth in SEQ ID NO:1), and shares at least about 75%, at least about 80%, at least about 85%, at least about 90%, at least about 95%, at least about 98%, or 100%, amino acid sequence identity over a contiguous stretch of at least about 1100 amino acids, at least about 1200 amino acids, or at least about 1300 amino acids, of amino acids 605-1922 of the amino acid sequence depicted in FIG. 7 and set forth in SEQ ID NO:1.

As another example, a subject modified Dicer polypeptide comprises one or more amino acid substitutions, insertions, or deletions in the DExD/H-box domain (e.g., within amino acids 63 to 71 of the amino acid sequence depicted in FIG. 7, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$). For example, in some embodiments, a subject modified Dicer polypeptide comprises one or more amino acid substitutions in the amino acid sequence CLNTGSGKT (SEQ ID NO:8) of the amino acid sequence depicted in FIG. 7, or a corresponding amino acid sequence of a Dicer polypeptide other than a human Dicer polypeptide. As shown in the amino acid sequence alignment presented in FIGS. 11A-I, the amino acid sequence CLNTGSGKT (SEQ ID NO:8) is conserved among Dicer polypeptides from various mammalian species.

For example, in some embodiments, a subject modified Dicer polypeptide comprises one or more non-conservative amino acid substitutions in the amino acid sequence CLNTGSGKT (SEQ ID NO:8) of the amino acid sequence depicted in FIG. 7, or a corresponding amino acid sequence of a Dicer polypeptide other than a human Dicer polypeptide. Exemplary, non-limiting examples of amino acid substitutions include, e.g., CLNDGSGKT (SEQ ID NO:9); CLNTPSGKT (SEQ ID NO:10); CLSTGSGKT (SEQ ID NO:11); and the like. For example, in some embodiments, a subject modified Dicer polypeptide: a) comprises a non-conservative amino acid substitution in the amino acid sequence CLNTGSGKT (SEQ ID NO:8; e.g., amino acids 63-71 of the amino acid sequence depicted in FIG. 7, or a corresponding amino acid sequence from a Dicer polypeptide other than a human Dicer polypeptide; b) shares at least about 75%, at least about 80%, at least about 85%, at least about 90%, at least about 95%, at least about 98%, or 100%, amino acid sequence identity over a contiguous stretch of from about 1600 amino acids to about 1700 amino acids, from about 1700 amino acids to about 1800 amino acids, or from about 1800 amino acids to about 1921 amino acids, of the amino acid sequence depicted in FIG. 7 and set forth in SEQ ID NO:1; and c) enhanced enzymatic activity (e.g., increased $k_{cat}$ and/or increased $k_{cat} \times K_m^{-1}$) compared to a Dicer polypeptide comprising the amino acid sequence depicted in FIG. 7 and set forth in SEQ ID NO:1.

As another example, a subject modified Dicer polypeptide comprises one or more amino acid substitutions, insertions, or deletions in the DExD/H-box domain (e.g., within amino acids 175-178 of the amino acid sequence depicted in FIG. 7, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$). For example, in some embodiments, a subject modified Dicer polypeptide comprises one or more amino acid substitutions in the amino acid sequence DECH (SEQ ID NO:25) of the amino acid sequence depicted in FIG. 7, or a corresponding amino acid sequence of a Dicer polypeptide other than a human Dicer polypeptide. As shown in the amino acid sequence alignment presented in FIGS. 11A-I, the amino acid sequence DECH (SEQ ID NO:25) is conserved among Dicer polypeptides from various mammalian species.

For example, in some embodiments, a subject modified Dicer polypeptide comprises one or more non-conservative amino acid substitutions in the amino acid sequence DECH (SEQ ID NO:25) of the amino acid sequence depicted in FIG. 7, or a corresponding amino acid sequence of a Dicer polypeptide other than a human Dicer polypeptide. For example, in some embodiments, a subject modified Dicer polypeptide: a) comprises a non-conservative amino acid substitution in the amino acid sequence DECH (SEQ ID NO:25; e.g., amino acids 175-178 of the amino acid sequence depicted in FIG. 7, or a corresponding amino acid sequence from a Dicer polypeptide other than a human Dicer polypeptide; b) shares at least about 75%, at least about 80%, at least about 85%, at least about 90%, at least about 95%, at least about 98%, or 100%, amino acid sequence identity over a contiguous stretch of from about 1600 amino acids to about 1700 amino acids, from about 1700 amino acids to about 1800 amino acids, or from about 1800 amino acids to about 1921 amino acids, of the amino acid sequence depicted in FIG. 7 and set forth in SEQ ID NO:1; and c) enhanced enzymatic activity (e.g., increased $k_{cat}$ and/or increased $k_{cat} \times K_m^{-1}$) compared to a Dicer polypeptide comprising the amino acid sequence depicted in FIG. 7 and set forth in SEQ ID NO:1.

In some embodiments, a modified Dicer polypeptide is a chimeric modified Dicer polypeptide, e.g., the modified Dicer polypeptide comprises a heterologous polypeptide. A heterologous polypeptide can be present at the carboxyl terminus, at the amino terminus, or at an internal site within the modified Dicer polypeptide. Suitable heterologous polypeptides include, e.g., epitope tags, including, but not limited to, hemagglutinin, FLAG, and the like; proteins that provide for a detectable signal, including, but not limited to, fluorescent proteins, enzymes (e.g., β-galactosidase, alkaline phosphatase, luciferase, horse radish peroxidase, etc.), and the like; polypeptides that facilitate purification or isolation of the fusion protein, e.g., metal ion binding polypeptides such as 6His tags, glutathione-S-transferase; etc.

For example, in some embodiments, a subject chimeric modified Dicer polypeptide: 1) lacks all or a portion of a DExD/H-box helicase domain; 2) comprises an amino acid sequence having at least about 75%, at least about at least about 80%, at least about 85%, at least about 90%, at least about 95%, at least about 98%, or at least about 99%, amino acid sequence identity to a contiguous stretch of from about 1100 amino acids to about 1150 amino acids, from about 1150 amino acids to about 1200 amino acids, from about 1200 amino acids to about 1250 amino acids, from about 1250 amino acids to about 1300 amino acids, or from about 1300 amino acids to about 1318 amino acids, of the amino acid sequence depicted in FIG. 9; and 3) comprises a heterologous, non-Dicer, polypeptide fused in-frame to the modified Dicer.

Compositions

The present invention provides a composition comprising a subject modified Dicer polypeptide.

A subject composition can comprise, in addition to the modified Dicer polypeptide, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

In some embodiments, a modified Dicer polypeptide present in a subject composition is pure, e.g., at least about 75%, at least about 80%, at least about 85%, at least about 90%, at least about 95%, at least about 98%, at least about 99%, or more than 99% pure, where "% purity" means that the modified Dicer polypeptide is the recited percent free from other proteins (e.g., proteins other than a subject modified Dicer polypeptide), other macromolecules, or contaminants that may be present during the production of the modified Dicer polypeptide.

Nucleic Acids

The present invention provides a nucleic acid comprising a nucleotide sequence encoding a subject modified Dicer polypeptide. A subject nucleic acid is useful for producing a subject modified Dicer polypeptide. A subject nucleic acid is recombinant. The present invention further provides a composition comprising a subject nucleic acid.

In some embodiments, a subject nucleic acid is an expression construct, e.g., an expression vector comprising a nucleotide sequence encoding a subject modified Dicer polypeptide, where the expression construct provides for production of the encoded modified Dicer polypeptide in an appropriate host cell. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli* and yeast).

Suitable vectors for the production of a subject modified Dicer polypeptide in a prokaryotic cell include plasmids of the types: pBR322-derived plasmids, pEMBL-derived plasmids, pEX-derived plasmids, pBTac-derived plasmids and pUC-derived plasmids for expression in prokaryotic cells, such as *Escherichia coli*. The following vectors are provided by way of example, for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia). However, any other plasmid or other vector may be used so long as it is compatible with the host cell.

A number of vectors exist for the expression of recombinant proteins in yeast. For instance, YEP24, YIPS, YEP51, YEP52, pYES2, and YRP17 are cloning and expression vehicles useful in the introduction of genetic constructs into *Saccharomyces cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 on, and in *S. cerevisiae* due to the replication determinant of the yeast 2 micron plasmid. In addition, drug resistance markers such as ampicillin can be used. In an illustrative embodiment, a subject modified Dicer polypeptide is produced recombinantly utilizing an expression vector generated by sub-cloning a nucleotide sequence encoding a subject modified Dicer polypeptide.

In some embodiments, the expression construct comprises a mammalian expression vector. Suitable mammalian expression vectors include those that contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17.

A subject modified Dicer polypeptide can be produced using an expression vector containing a nucleic acid encoding a Dicer polypeptide, operably linked to at least one transcriptional regulatory sequence. Operably linked is intended to mean that the nucleotide sequence is linked to a regulatory sequence in a manner that allows expression of the nucleotide sequence. Regulatory sequences are art-recognized and are selected to direct expression of the encoded modified Dicer protein. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding Dicer polypeptides to recombinantly produce Dicer. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAG or TRC system, T7 promoter whose expression is directed by T7 RNA polymerase, the major operator and promoter regions of phage X, polyhedron promoter, the control regions for fd coat protein, the promoter for 3-phosphoglycerate kinase or other glycolytic enzymes, the promoters of acid phosphatase, e.g., PhoS, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol., 1991: 173(1): 86-93; Alpuche-Aranda et al., PNAS, 1992; 89(21): 10079-83), a nirB promoter (Harborne et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) Infect. Immun. 70:1087-1096); an rpsM promoter (see, e.g., Valdivia and Falkow (1996). Mol. Microbiol. 22:367); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); an SP6 promoter (see, e.g., Melton et al. (1984) Nucl. Acids Res. 12:7035-7056); and the like.

Non-limiting examples of suitable eukaryotic promoters include CMV immediate early, HSV thymidine kinase, early and late SV40, LTRs from retrovirus, and mouse metallothionein-I. Suitable promoters for expression in yeast include, but are not limited to, CYC1, HIS3, GAL1, GAL10, ADH1, PGK, PHO5, GAPDH, ADC1, TRP1, URA3, LEU2, ENO, and TP1; and, e.g., AOX1 (e.g., for use in Pichia).

In some embodiments, the promoter is an inducible promoter. Suitable inducible promoters include, but are not limited to, the pL of bacteriophage Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) J. Bacteriol. 177:4121-4130); a xylose-inducible promoter, e.g., Pxyl (see, e.g., Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) FEMS Microbiol Lett. 177(2):327-34); and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

Compositions

The present invention provides a composition comprising a subject nucleic acid. A subject composition can comprise, in addition to a subject nucleic acid, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; glycerol; and the like.

Genetically Modified Host Cells

The present invention provides genetically modified host cells comprising a subject nucleic acid. Suitable host cells include, e.g., prokaryotic host cells (e.g., prokaryotic cells in vitro); and eukaryotic cells that are cultured as single-celled entities in vitro. Eukaryotic host cells include, e.g., insect cells; primary mammalian cells; immortalized mammalian cell lines; and the like. The present invention further provides composition comprising a subject genetically modified host cell.

Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. In some embodiments, the host cell is *Escherichia coli*.

Suitable eukaryotic host cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable methods of genetic modification of a host cell include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. To generate a subject genetically modified host cell, a subject nucleic acid is introduced stably or transiently into a host cell, using established techniques, including, but not limited to, electroporation, lithium acetate transformation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

Compositions

The present invention provides a composition comprising a subject genetically modified host cell. A subject composition comprises a subject genetically modified host cell, and will in some embodiments comprise one or more further components, which components are selected based in part on the intended use of the genetically modified host cell, storage considerations, etc. Suitable components include, but are not limited to, salts; buffers; stabilizers; protease-inhibiting agents; nuclease-inhibiting agents; cell membrane- and/or cell wall-preserving compounds, e.g., glycerol, dimethylsulfoxide, etc.; nutritional media appropriate to the cell; and the like. In some embodiments, the cells are lyophilized

Production of a Subject Modified Dicer Polypeptide

A host cell is genetically modified with a subject nucleic acid, such that a subject modified Dicer polypeptide is produced in the genetically modified host cell, and the encoded modified Dicer polypeptide is produced by the cell. The genetically modified host cell is cultured in vitro under suitable conditions such that the modified Dicer polypeptide is produced. Where the nucleotide sequence encoding a subject modified Dicer polypeptide is operably linked to an inducible promoter, an inducer is added to the culture medium in which the genetically modified host cell is cultured.

The modified Dicer polypeptide can be recovered and isolated from the genetically modified host cell. In some embodiments, the modified Dicer polypeptide is purified, e.g., is at least about 80%, at least about 85%, at least about 90%, at least about 95%, at least about 98%, or at least about 99% pure. Any convenient protein purification procedures may be employed, where suitable protein purification methodologies are described in Guide to Protein Purification, (Deuthser ed.) (Academic Press, 1990). For example, a lysate may be prepared from a genetically modified host cell that expresses a subject modified Dicer polypeptide, and purified using any of a number of standard protein purification methods, e.g., high performance liquid chromatography, size exclusion chromatography, gel electrophoresis, affinity chromatography, and the like.

Utility

A subject modified Dicer polypeptide is useful for producing small regulatory RNAs, which in turn are useful in a number of applications, including basic research applications, drug screening/target validation, large scale functional library screening, and therapeutic applications. Thus, the present invention provides methods of producing a small regulatory RNA molecule from a substrate dsRNA molecule
Small regulatory RNA molecules that can be produced using a subject method include siRNA and miRNA.

Methods of Producing a Small Regulatory RNA Molecule

The present invention provides methods of producing small regulatory RNA from a substrate dsRNA molecule, the methods generally involving contacting the substrate dsRNA molecule with a subject modified Dicer polypeptide, where the modified Dicer polypeptide efficiently produces a small regulatory RNA using the substrate dsRNA molecule. The methods described below are directed to producing siRNA; however, a subject method can be adapted for producing miRNA.

In some embodiments, a subject method provides for production of a plurality of small regulatory RNA molecules, e.g., a plurality of siRNA molecules or a plurality of miRNA molecules. By "plurality" is meant at least 2, at least about 5, or at least about 10, where the number of distinct siRNA or miRNA molecules produced from a given substrate dsRNA molecule in the subject methods can depend on the length of the substrate dsRNA molecule, but may be as high as about 25 or higher, e.g., about 100, or about 400 or higher.

The siRNA or miRNA product molecules can range in length from about 10 nucleotides (nt) to about 25 nt, e.g., from about 10 nt to about 15 nt, from about 15 nt to about 20 nt, or from about 20 nt to about 25 nt. In some embodiments, a subject modified Dicer polypeptide produces siRNA product molecules having a length of from about 19 nt to about 24 nt, from about 20 nt to about 24 nt, from about 21 nt to about 24 nt, or from about 21 nt to about 23 nt. In some embodiments, a subject modified Dicer polypeptide produces siRNA product molecules, where at least about 75%, at least about 80%, at least about 85%, at least about 90%, at least about 95%, at least about 98%, or at least about 99%, of the siRNA molecules have a length of from 21 nt to 23 nt.

A subject modified Dicer polypeptide is contacted with a substrate dsRNA molecule. The length of the parent dsRNA molecule can vary, but generally the length is at least about 300 bp, at least about 500 bp, or at least about 1000 bp, where the length may be as long as about 2000 bp or longer, but often does not exceed about 8000 bp, e.g., about 6000 bp.

The dsRNA substrate can comprise two hybridized strands of polymerized ribonucleotide. The dsRNA substrate can include modifications to either the phosphate-sugar backbone or the nucleoside. For example, the phosphodiester linkages of natural RNA may be modified to include at least one of a nitrogen or a sulfur heteroatom. Modifications in RNA structure may be tailored to allow specific genetic inhibition while avoiding an adverse response in the cell harboring the RNA. Likewise, bases may be modified to block the activity of adenosine deaminase. The dsRNA substrate may be produced enzymatically or by partial/total organic synthesis, any modified ribonucleotide can be introduced by in vitro enzymatic or organic synthesis.

The dsRNA substrate is formed by a single self-complementary RNA strand or by two complementary RNA strands. dsRNA substrates comprising a nucleotide sequence identical to a portion of a target gene may be employed. RNA sequences with insertions, deletions, and single point mutations relative to the target sequence are also of interest. Thus, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BEST-FIT software program using default parameters (e.g., University of Wisconsin Genetic Computing Group). In some embodiments, there is at least about 80%, at least about 85%, at least about 90%, at least about 95%, at least about 98%, at least about 99%, or 100%, sequence identity between the siRNA or miRNA and the portion of a target gene may be of interest. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 50° C. or 70° C. hybridization for 12-16 hours; followed by washing; or conditions that are at least as stringent as these representative conditions). The length of the identical nucleotide sequences may be, for example, at least about 25, about 50, about 100, about 200, about 300 or about 400 bases or longer. In certain embodiments, the dsRNA substrate is from about 400 to about 800 bases in length. In certain embodiments 100% sequence identity between the RNA and the target gene is not required to practice inhibition applications of the invention. Thus the invention has the advantage of being able to tolerate sequence variations that might be expected due to genetic mutation, strain polymorphism, or evolutionary divergence.

The dsRNA substrate can be synthesized either in vivo or in vitro. Furthermore, the dsRNA substrate can be synthesized in vitro in a living cell, or in a cell-free in vitro system. Endogenous polymerase of the cell can mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the dsRNA strand (or strands). In some embodiments, the RNA strands of the dsRNA substrate are polyadenylated. In other embodiments, the RNA strands of the dsRNA substrate are not polyadenylated. In some embodiments, the RNA strands of the dsRNA substrate are capable of being translated into a polypeptide by a cell's translational apparatus or in a cell-free in vitro translation system. In some embodiments, the RNA strands of the dsRNA substrate are not capable of being translated into a polypeptide by a cell's translational apparatus or in a cell-free in vitro translation system.

The dsRNA substrate can be chemically or enzymatically synthesized by manual or automated reactions. The dsRNA substrate can be synthesized by a cellular RNA polymerase or a bacteriophage RNA polymerase (e.g., T3, T7, or SP6), e.g., using an expression construct encoding the dsRNA as template. The use and production of expression constructs are known in the art (see WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA can be purified prior to introduction into the cell. For example, RNA can be purified from a mixture by extraction with a solvent or resin, precipitation, electrophoresis, chromatography or a combination thereof. Alternatively, the dsRNA construct may be used with no or a minimum of purification to avoid losses due to sample processing. The dsRNA construct may be dried for storage or dissolved in an aqueous solution. The solution may contain buffers or salts to promote annealing, and/or stabilization of the duplex strands.

In some embodiments, at least about 60%, at least about 75%, at least about 80%, at least about 85%, at least about 90%, at least about 95%, at least about 98%, or at least about 99%, of the substrate dsRNA is cleaved to produce an miRNA or siRNA product.

In the reaction composition (e.g., the composition comprising a subject modified Dicer polypeptide and a dsRNA substrate), the amount of Dicer present in the composition can vary, and can be in a range of from about 20 ng/μl to about 160 ng/μl, e.g., from about 20 ng/μl to about 40 ng/μl, from about 40 ng/μl to about 60 ng/μl, from about 60 ng/μl to about 80 ng/μl, from about 80 ng/μl to about 100 ng/μl, from about 100 ng/μl to about 120 ng/μl, from about 120 ng/μl to about 140 ng/μl, or from about 140 ng/μl to about 160 ng/μl.

In some embodiments, the reaction composition (e.g., the composition comprising a subject modified Dicer polypeptide and a dsRNA substrate) is an aqueous composition, where the composition may include one or more additional components, e.g., buffers; salts such as NaCl, $MgCl_2$, and the like; EDTA; DTT; ATP; and the like.

As discussed above, a subject method comprises contacting a subject modified Dicer polypeptide with a substrate dsRNA in a reaction composition that is then maintained under conditions sufficient to produce the desired siRNA or miRNA product. In some embodiments, a subject method is a cell-free in vitro method, by which is meant that the method occurs in a cell free environment, e.g., not inside of a cell or in the presence of cells. As such, in some embodiments, a subject method involves producing a product composition comprising an siRNA product or a miRNA product, where the product composition is produced by contacting a substrate dsRNA and a subject modified Dicer polypeptide, as described above, where the product composition is produced in a cell-free in vitro reaction, i.e., in vitro and outside of a cell.

In some embodiments, a subject modified Dicer polypeptide and a substrate dsRNA are contacted in reaction composition that includes a sufficient amount of $Mg^{2+}$ to ensure adequate Dicer activity, where the amount of $Mg^{2+}$ can range from about 0.5 mM to about 1.0 mM, or from about 2.5 mM to about 5.0 mM. In some embodiments, the reaction composition is free of ATP, and in other embodiments, 1 mM ATP is used in the reaction composition.

The reaction mixture is typically maintained under incubation conditions sufficient to produce the desired small regulatory RNA product. The reaction mixture is typically maintained at a temperature that ranges from about 30° C. to about 37° C., e.g., from about 35° C. to about 37° C. The reaction is carried out for a period of time ranging from about 15 minutes to about 24 hours, e.g., from about 15 minutes to about 30 minutes, from about 30 minutes to about 60 minutes, from about 1 hour to about 2 hours, from about 2 hours to about 4 hours, from about 4 hours to about 8 hours, from about 8 hours to about 12 hours, from about 12 hours to about 16 hours, or from about 16 hours to about 24 hours.

The small regulatory RNA product, e.g., the siRNA product or the miRNA produce, produced by a subject method may be used as is or further processed prior to use, e.g., separated from other components of the reaction mixture, e.g., the modified Dicer protein, any remaining dsRNA substrate, salts, buffers, etc. Any convenient separation protocol may be employed, including gel purification, chromatographic separation based on molecular weight or affinity resins, and classical precipitation, and the like.

Research Applications

A small regulatory RNA can be used for modifying biological functions in a cell (e.g., a cell growing as a single-cell suspension in vitro; a cell in a multicellular organism; etc.), such as for example, RNA interference, gene knockdown or knockout, generating expression mutants, modulating cell growth, differentiation, signaling or a combination thereof. Thus, in some embodiments, a subject method involves: a) producing an siRNA using a subject method (i.e., using a subject modified Dicer polypeptide); and b) introducing the siRNA so produced into a cell (e.g., into a cell in vitro; or into a non-human cell in a multi-cellular organism in vivo).

One representative utility is a method of identifying gene function in an organism, e.g., higher eukaryotes comprising the use of the product siRNA to inhibit the activity of a target gene of previously unknown function. Instead of the time consuming and laborious isolation of mutants by traditional genetic screening, functional genomics using the subject product siRNA determines the function of uncharacterized genes by employing the siRNA to reduce the amount and/or alter the timing of target gene activity. The product siRNA can be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for mammalian genomes, can be coupled with use of the product siRNA to determine gene function in a cell or in a whole organism. The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

A simple representative assay involves inhibition of gene expression according to the partial sequence available from an expressed sequence tag (EST). Functional alterations in growth, development, metabolism, disease resistance, or other biological processes would be indicative of the normal role of the EST's gene product.

The ease with which the product siRNA construct can be introduced into an intact cell/organism containing the target gene allows the siRNA products to be used in high throughput screening (HTS). For example, individual clones from the library can be replicated and then isolated in separate reactions, but preferably the library is maintained in individual reaction vessels (e.g., a 96-well microtiter plate) to minimize the number of steps required to practice the invention and to allow automation of the process. Solutions containing the product siRNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity.

The siRNA can be fed directly to, injected into, the cell/organism containing the target gene. The siRNA may be directly introduced into the cell (i.e., intracellularly); or introduced extracellularly into a cavity, interstitial space, into the circulation of an organism, introduced orally, or may be introduced by bathing an organism in a solution containing the siRNA. Methods for oral introduction include direct mixing of RNA with food of the organism. Physical methods of introducing nucleic, acids include injection directly into the cell or extracellular injection into the organism of an RNA solution. The siRNA may be introduced in an amount that allows delivery of at least one copy per cell. Higher doses (e.g., at least 5, 10, 100, 500 or 1000 copies per cell) of siRNA material may yield more effective inhibition; lower doses may also be useful for specific applications Inhibition is sequence-specific in that nucleotide sequences corresponding to the duplex region of the RNA are targeted for genetic inhibition.

The function of the target gene can be assayed from the effects it has on the cell/organism when gene activity is inhibited. This screening could be amenable to small subjects that can be processed in large number, for example, tissue culture cells derived from invertebrates or vertebrates (e.g., mammals, such as murines, non-human primates, and humans).

If a characteristic of an organism is determined to be genetically linked to a polymorphism through RFLP or QTL analysis, the present invention can be used to gain insight regarding whether that genetic polymorphism might be directly responsible for the characteristic. For example, a fragment defining the genetic polymorphism or sequences in the vicinity of such a genetic polymorphism can be amplified to produce a dsRNA from which siRNA is prepared according to the subject methods, which siRNA can be introduced to the organism or cell, and whether an alteration in the characteristic is correlated with inhibition can be determined.

The present invention is useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of siRNA at specific times of development and locations in the organism without introducing permanent mutations into the target genome.

In situations where alternative splicing produces a family of transcripts that are distinguished by usage of characteristic exons, an siRNA can target inhibition through the appropriate exons to specifically inhibit or to distinguish among the functions of family members.

Therapeutic Applications

An siRNA produced using a subject method also finds use in a variety of therapeutic applications in which it is desired to selectively modulate one or more target genes in a host, e.g., a whole animal, or a portion thereof, e.g., a tissue, an organ, etc, as well as in cells present such an animal, tissue, or organ. In such methods, an effective amount of an siRNA is administered to the host or target portion thereof. By "effective amount" is meant a dosage sufficient to selectively modulate expression of the target gene(s), as desired. As indicated above, in many embodiments of this type of application, methods are employed to reduce/inhibit expression of one or more target genes in the host or portion thereof in order to achieve a desired therapeutic outcome.

In some embodiments, a subject method comprises: preparing an siRNA according to a subject method (i.e., using a subject modified Dicer polypeptide); and administering an effective amount of the siRNA to an individual in need thereof.

Depending on the nature of the condition being treated, the target gene may be a gene derived from the cell, an endogenous gene, a pathologically mutated gene, e.g. a cancer-causing gene, one or more genes whose expression causes or is related to heart disease, lung disease, Alzheimer's disease, Parkinson's disease, diabetes, arthritis, etc.; a transgene, or a gene of a pathogen which is present in the cell after infection thereof, e.g., a viral (e.g., HIV-Human Immunodeficiency Virus; Hepatitis B virus; Hepatitis C virus; Herpes-simplex virus-1 and -2; Varicella Zoster (Chicken pox and Shingles); Rhinovirus (common cold and flu); any other viral form); or bacterial pathogen. Depending on the particular target gene and the dose of siRNA delivered, the procedure may provide partial or complete loss of function for the target gene. Lower doses of injected material and longer times after administration of siRNA may result in inhibition in a smaller fraction of cells.

An siRNA produced using a subject method finds use in the treatment of a variety of conditions in which the modulation of target gene expression in a mammalian host is desired. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable using an siRNA. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, and non-human primates such as chimpanzees and monkeys). In some embodiments, the hosts will be humans.

The present invention is not limited to modulation of expression of any specific type of target gene or nucleotide sequence. Representative classes of target genes of interest include but are not limited to: developmental genes (e.g., adhesion molecules, cyclin kinase inhibitors, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, EBRB2, ETSI, ETS1, ETV6, FOR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor genes (e.g., APC, BRCA 1, BRCA2, MADH4, MCC, NF 1, NF2, RB 1, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, Upases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases); chemokines (e.g. CXCR4, CCR5); the RNA component of telomerase; vascular endothelial growth factor (VEGF); VEGF receptor; tumor necrosis factors nuclear factor kappa B; transcription factors; cell adhesion molecules; Insulin-like growth factor; transforming growth factor beta family members; cell surface receptors; RNA binding proteins (e.g. small nucleolar RNAs, RNA transport factors); translation factors; telomerase reverse transcriptase); etc.

The siRNA can be introduced into the target cell(s) using any convenient protocol, where the protocol will vary depending on whether the target cells are in vitro or in vivo.

Where the target cells are in vivo, the siRNA can be administered to the host comprising the cells using any convenient protocol, where the protocol employed is typically a nucleic acid administration protocol, where a number of different such protocols are known in the art. The following discussion provides a review of representative nucleic acid administration protocols that may be employed. The nucleic acids may be introduced into tissues or host cells by any number of routes, including microinjection, or fusion of vesicles. Jet injection may also be used for intra-muscular administration, as described by Furth et al. (1992), *Anal Biochem* 205:365-368. The nucleic acids may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

For example, the d-siRNA agent can be fed directly to, injected into, the host organism containing the target gene. The agent may be directly introduced into the cell (i.e., intracellularly); or introduced extracellularly into a cavity, interstitial space, into the circulation of an organism, introduced orally, etc. Methods for oral introduction include direct mixing of RNA with food of the organism. Physical methods of introducing nucleic acids include injection directly into the cell or extracellular injection into the organism of an RNA solution.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. Pat. Nos. 5,985,847 and 5,922,687 (the disclosures of which are herein incorporated by reference); Acsadi et al., New Biol. (1991) 3:71-81; Hickman et al., Hum. Gen. Ther. (1994) 5:1477-1483; and Wolff et al., Science (1990) 247: 1465-1468; etc.

An siRNA (also referred to as an "agent" or an "active agent") can be administered to the host using any convenient means capable of resulting in the desired modulation of target gene expression. Thus, the agent can be incorporated into a variety of formulations for therapeutic administration. More particularly, the agents can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

Suitable delivery reagents for administration of an siRNA include the Mints Transit TKO lipophilic reagent; lipofectin; lipofectamine; cellfectin; polycations (e.g., polylysine); and liposomes.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more agents Similarly, unit dosage forms for injection or intravenous administration may comprise the agent(s) in a composition as a solution in sterile water, normal saline or another pharmaceutically acceptable carrier.

The term "unit dosage form," as used herein, refers to physically discrete units suitable as unitary dosages for human and non-human animal subjects, each unit containing a predetermined quantity of an active agent calculated in an amount sufficient to produce the desired effect in association with a pharmaceutically acceptable diluent, carrier or vehicle.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given active agent are readily determinable by those of skill in the art by a variety of means.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Generation and Characterization of a Modified Dicer

Materials and Methods
RNA Substrates

A 73 nucleotide (nt) human let-7 (hlet-7) hairpin RNA was transcribed by T7 RNA polymerase from a construct built in a hammerhead-hepatitis delta virus double ribozyme system. All of other RNA substrates used in this study were synthesized by IDT (Integrated DNA Technologies, Inc, Coralville, Iowa). All of the RNAs were purified by 16% urea-PAGE. For both filter binding and dicing assays, the purified RNA substrates were 5'-end $^{32}$P labeled with T4 polynucleotide kinase (New England Biolab, Inc. Beverly, Mass.). The RNA substrates used in this study are:

```
hlet-7,
                                            (SEQ ID NO: 7)
5'-UGAGGUAGUAGGUUGUAUAGUUUUAGGGUCACACCCACCACUGGGA GAUAACUAUACAAUCUACUGUCUUACC-3';
37a,
                                            (SEQ ID NO: 5)
5'-UGAGGUAGUAGGUUGUAUAGUUUGAAAGUUCACGAUU-3';
and 37b,
                                            (SEQ ID NO: 6)
5'-UCGUGAACUUUCAAACUAUACAACCUACUACCUCAUU-3'.
```

Generation of hDicer Proteins

To generate human Dicer (hDcr) recombinant proteins, a full length wild-type and ΔDEAD (deletion of DEAD domain) hDcr cDNAs (accession number NP_803187) was generated by PCR with primer sets of hDcr-F/hDcr-R and DEAD-F/hDcr-R, respectively (see below). The PCR products were cloned into pFastBac plasmid (Invitrogen) after Sfo I and Xho I digestions. All of other constructs to produce hDcr-derivative proteins were generated by PCR using QuickChange II XL Site-Directed Mutagenesis Kit (Stratagene) with primer set of DUF-F/DUF-R to delete DUF283, and with primer set of dsRBD-F/dsRBD-R to delete dsRBD domain (see the sequences below). For generation of double-deletion of DEAD and dsRBD domains, ΔDEAD hDcr cDNA was used as template in a PCR reaction with primer set of dsRBD-F/dsRBD-R. For generation of hWalker (a point-mutation in ATP-binding motif in DEAD domain), a PCR was performed with the primers of hW-F and hW-R in the presence of wild-type hDcr cDNA. The corresponding recombinant Bacmid DNAs were obtained by transforming pFastBac plasmids into competent DH10Bac *E. Coli* cells (Invitrogen) and these Bacmid DNAs were transfected into Sf9 cells with FuGene Transfection Reagent (Roche Applied Science) for generating baculovirus, which is used to produce of recombinant hDcr proteins in Sf9 cells. The hDcr proteins were purified through Ni$^{2+}$-affinity followed by gel filtration column of HiLoad 16/60 Superdex 200 (GE Healthcare).

The PCR oligos (primers) are shown below (restriction sites for Sfo I and Xho I are underlined):

```
hDcr-F:
                                           (SEQ ID NO: 12)
5'-GGGGGCGCCATGAAAAGCCCTGCTTTGCAACCCCTCAG

CATGGCAG-3';

hDcr-R:
                                           (SEQ ID NO: 13)
5'-CCCCTCGAGTCAGCTATTGGGAACCTGAGGTTGATTAGC-3';

DEAD-F:
                                           (SEQ ID NO: 14)
5'-GGGGGCGCCATGGATGATGATGACGTTTTCCCACCATA

TGTGTTG-3';

DUF-F:
                                           (SEQ ID NO: 15)
5'-CGAGTCACAATCAACACGGACCATTTGATGCCAGTTGG

GAAAGAG-3';

DUF-R:
                                           (SEQ ID NO: 16)
5'-CCCAACTGGCATCAAATGGTCCGTGTTGATTGTGACTC

GTGGACC-3';

dsRBD-F:
                                           (SEQ ID NO: 17)
5'-GAAAAGTTTTCTGCAAATAATCAACCTCAGGTTCCCAA

TAGCTG-3';

dsRBD-R:
                                           (SEQ ID NO: 18)
5'-GGGAACCTGAGGTTGATTATTTGCAGAAAACTTTTCTA

TTAGTGGC-3';

hW-F:
                                           (SEQ ID NO: 19)
5'-AACACTGGCTCAGGGGCGACATTTATTGCAGTAC-3';

hW-R:
                                           (SEQ ID NO: 20)
5'-GTACTGCAATAAATGTCGCCCCTGAGCCAGTGTT-3'.
```

Filter Binding Assay

A serial dilution of proteins were incubated in a buffer containing 20 mM Tris-Cl (pH 7.5), 25 mM NaCl, 5 mM EDTA, 1 mM dithiothreitol (DTT), 1% glycerol and ~0.5-1 nM (1500 c.p.m.) of $^{32}$P-labeled duplex RNA substrate (one strand was labeled) at room temperature for 60 min in a volume of After this incubation, 25 µl of each reaction were used for dot-blotting, which was conducted in a dot-blot apparatus equipped with 3 membranes of Tuffryn, Protran and Nytran (from top to bottom). After dried, the bound (on Protran) or free (on Nytran) RNAs were detected and quantified with Phosphoimager (GE Healthcare). Percentage of bound RNAs was calculated by 100 multiplied by the ratio of radioactivity (volumes) detected on the Protran membrane over the total input volumes (radioactivity). The bound RNAs (%) (Y-axle) were plotted against protein concentrations (X-axle). $K_d$ was determined by global fitting to the equation of $k_{obsd} = (k_{max} \times [Dicer])(K_{1/2} + [Dicer])^{-1}$, here $k_{obsd}$ is the observed rate constant at a particular protein concentration, $k_{max}$ is the maximal rate constant with saturating protein, and $K_{1/2}$ (or $K_d$) is the protein concentration that provides half the maximal rate. Curve fitting was conducted with KleidaGraph (Synery Software).

In Vitro dsRNase Activity Assay

For a dsRNase assay (dicing assay), a high specific radioactivity dsRNA substrate was 5'-end labeled with (γ-$^{32}$P)ATP. The labeled RNA was either self-annealed (forming a hairpin RNA substrate) or annealed with its complementary oligo. An in vitro dsRNase assay was performed with certain amount of hDcr protein and certain amount of RNA substrate (indicated in figure legends) at 30° C. for certain period of time in a volume of 10 μl (unless otherwise indicated) of 20 mM Tris-Cl (pH 6.5), 1.5 mM MgCl$_2$, 25 mM NaCl, 1 mM DTT and 1% glycerol. Reactions were stopped by addition of 1.2 volume of loading buffer (95% formamide, 18 mM EDTA, 0.025% SDS, 0.1% xylene cyanol and 0.1% bromphenol blue). After heating at 75° C. for 10 min, the samples were analyzed by electrophoresis on a 15% polyacrylamide-7M urea gel run in TBE buffer. The gel was dried and the products were detected and quantified by Phosphoimager (GE Healthcare).

Kinetic Analysis of Human Dicer Proteins

A single-turnover experiment was performed in 90 μl reaction mixture containing 1-2 nM of label duplex RNA substrate and 60 nM of protein. 10 μl of reaction mixture were taken out and put into 12 μl of RNA loading buffer at the time points of 0, 0.5, 1, 2, 2.5, 5, 10, 20, 40, and 80 min, respectively. The RNAs in the aliquots were fractioned by 15% urea-polyacrylamide gel electrophoresis and images were quantified by Phosphorimager. Graphs were made by using KleidaGraph.

In order to obtain serial initial rates of human Dicer proteins, multiple-turnover experiments were performed in 90 μl reaction mixture containing 5 nM protein and duplex RNA at concentration of 25, 50, 75, 100, 150, 225, and 375 nM, respectively. Aliquots were taken at the time points of 0, 0.5, 1, 2, 2.5, 5, 10, 20, 40, and 80 min, respectively and analyzed by gel electrophoresis. After quantification, initial rates were determined by linear regression (from 0 to 10 min) using Excel. $K_m$ was determined by KleidaGraph global fitting to the equation of $V=(V_{max} \times (K_m+S))^{-1}$, where V is the velocity or initial rate, S is target RNA concentration.

Results

Dicer's DExD/H-Box Domain Inhibits Single-Turnover dsRNA Cleavage Rates

To investigate dsRNA recognition and cleavage by human Dicer, the wild-type (accession no. NP_803187) and five mutant forms of recombinant human Dicer (hDcr) protein were prepared (FIG. 1A). Specifically, a point mutation of lysine to alanine at position 70 (K70A) in the ATP-binding motif (hWalker) and a deletion of amino acids 1-604 spanning the entire DExD/H-box domain (ΔDEAD) were created to analyze the functional contributions of the DExD/H-box domain To explore the role of the C-terminal double-stranded RNA binding domain (dsRBD) and the domain of unknown function (DUF283) domains, hDcr variants lacking these domains were prepared (ΔdsRBD$_{1844-1922}$ and ΔDUF$_{630-709}$, respectively). A more substantially truncated form of hDcr (2DD) was prepared lacking both the DExD/H-box and the dsRBD domains. Each Dicer variant was produced using a baculovirus expression system and purified by Ni$^{2+}$-affinity chromatography followed by gel filtration chromatography after site-specific protease cleavage to remove the N-terminal His$_6$ affinity tag. In each case, 0.5-1.0 mg of purified recombinant protein was obtained routinely from one liter of cell culture (FIG. 1B). Activity assays showed that all five hDcr variants were able to cleave double-stranded RNA substrates (FIG. 1C).

FIGS. 1A-C. Domain structures and expression of human Dicers (hDcrs). A, Schematic illustration of the domain structure of different hDcrs; B, Polyhistidine-tagged recombinant proteins, expressed in a baculovirus expression system and purified by gel filtration after N$^{2+}$-affinity chromatography and analyzed by 10% SDS-PAGE; C, A dsRNase activity assay (with 60 nM protein and 2-4 nM $^{32}$P-labeled duplex RNA 37ab), showing all of recombinant proteins are active.

Figure 2B:
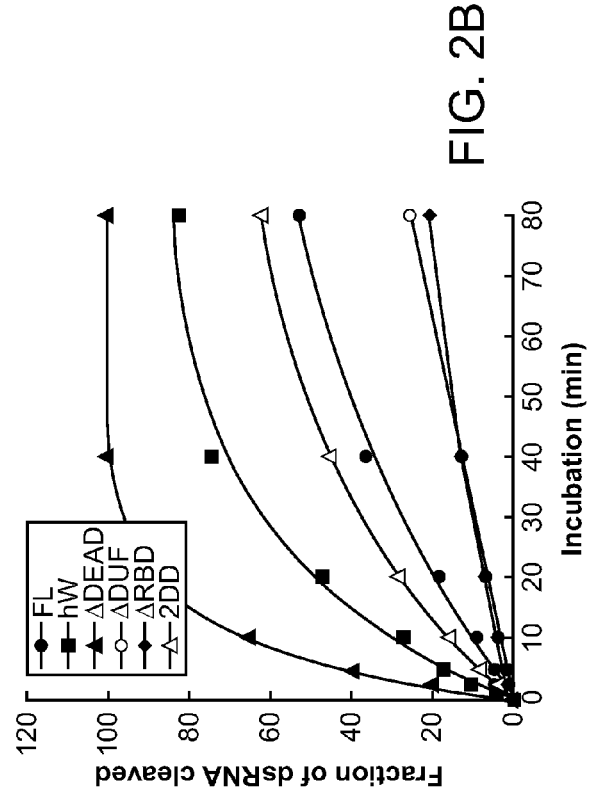

To assess the contributions of various hDcr domains to dicing activity, we first tested the catalytic activity of each hDcr variant under single-turnover conditions using two different substrates. One substrate was a double-stranded RNA substrate containing 2-nucleotide 3' overhangs on either end (37ab), whereas the other was the human pre-let7 hairpin RNA (FIG. 2A). In the presence of excess protein, the wild-type hDcr enzyme catalyzed cleavage of the 37ab substrate to yield 22-nt. products at an initial rate of 0.18 fmol min$^{-1}$ (FIG. 2B, D). Deletion of either the dsRBD or the DUF domain significantly reduced the observed cleavage rate under these single-turnover conditions. These results are consistent with previous data showing that deletion of the dsRBD resulted in decreases of 1.9- and 2.5-fold cleavage rate for dsRNA and hairpin RNA, respectively (Zhang et al, 2004). Surprisingly, however, deletion or mutation of the DExD/H-box domain significantly enhanced the cleavage rate relative to that observed for the wild-type enzyme (FIG. 2B, D). Deletion of the DExD/H-box domain had the most pronounced effect, with an ~8-fold faster rate of dicing as measured for the 37ab dsRNA substrate.

Figures 2C, 2D:
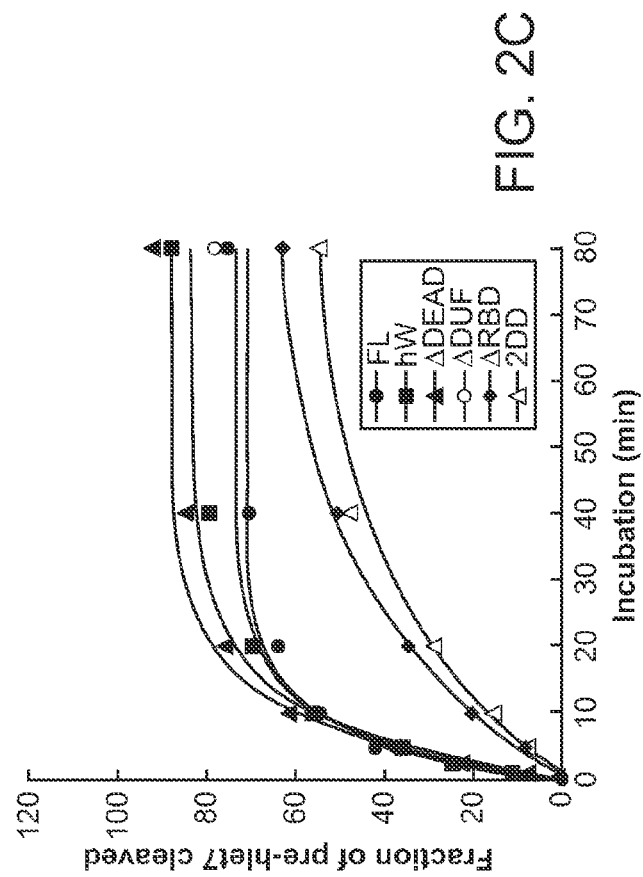

More modest differences were observed for the pre-let7 substrate, although in general this RNA was cleaved 6-18 fold more rapidly than 37ab (FIG. 2C, D). Different cleavage efficiencies by hDcr on pre-miRNAs and generic dsRNA substrates were observed previously (Provost et al, 2002), implying that miRNAs and siRNAs are recognized or processed differently in vivo. The lack of pronounced stimulation of pre-let7 cleavage by the hDcr lacking DExD/H-box domain is consistent with the finding that deletion of the DExD/H-box domain of Drosophila Dicer1 (Dcr1) does not significantly affect pre-miRNA processing activity (Lee et al, 2006; Ye et al, 2007). Taken together, our data show that the activity of hDcr is substrate-dependent, and its DExD/H-box domain inhibits cleavage, particularly for a prefect-duplex dsRNA substrate.

FIGS. 2A-D. Single-turnover activity of hDcr proteins. A, Schematic illustration of a perfectly-matched dsRNA (37ab, right top panel) and a miniature pre-miRNA (pre-hlet-7, right bottom). The asterisks (*) in the substrates indicate that the substrate or strand was 5'-end labeled with $^{32}$P. Left panel is an example showing a time-course dicing assay of flhDcr (120 nM) with 2 nM 5'-end labeled 37ab dsRNA after 80 min incubation at 37° C. B and C, Graphs showing single-turnover dicing assays of hDcr proteins (60 nM) with 2-4 nM (3000 c.p.m.) duplex RNA substrate 37ab (2B) or pre-hlet-7 (2C). Value at each time point was averaged from 2 independent experiments. Fraction of duplex RNAs cleaved (%) (Y-axle) were plotted against incubation time (min) (X-axle), and cleavage fraction curves were obtained by global fitting with Kleidagraph (Synery Software) to the equation of S=(a−b) exp(−k$_{obsd}$t)+b, here S is the fraction of dsRNA cleaved at each time point, a is the fraction of dsRNA at the beginning of the reaction, b is the fraction of dsRNA at the reaction plateau (t-->∞), and k$_{obsd}$ is the observed rate constant of the reaction; D, A summary of initial rates of hDcr proteins with RNA substrates 37ab and pre-hlet-7, calculated from first 10 min data.

Dicer's DExD/H-Box Domain Does Not Significantly Alter Substrate Binding Affinity The substrate-dependent differences in dicing activity observed for the different human Dicer variants might reflect differences in substrate recognition. To test this possibility, we measured the binding affinity of the hDcr recombinant proteins to either the perfect duplex (37ab) or pre-hlet-7

RNA. Under conditions in which free magnesium ions are chelated and hence dicing is inhibited, the affinities of four of the mutant hDcr enzymes for either substrate were within three-fold of those measured for the full-length enzyme (75 nM and 30 nM, respectively) (FIG. 3) Similar $K_d$s were obtained using a 64 nt duplex RNA. These values are similar to those measured previously (Provost et al, 2002; Vermeulen et al, 2005). A catalytically inactive hDcr protein showed similar binding affinities for each RNA in the presence of 10 mM $Mg^{2+}$, confirming that there are no measurable effects of magnesium on RNA binding (Provost et al, 2002; Zhang et al, 2002). Notably, deletion of the dsRBD did not significantly affect RNA binding affinity, in contrast to a previous report showing that a segment of the dsRBD alone binds to dsRNA (Zhang et al, 2004) (FIG. 3A, B). Furthermore, our results do not support the prediction that the DUF283 domain is a dsRNA-binding domain as suggested previously (Dlakic, 2006). The protein lacking both the DExD/H-box domain and the dsRBD (2DD) bound ~3-4 fold more weakly to either substrate relative to full-length Dicer (FIG. 3A-C). It is possible that this severely truncated protein is generally destabilized, or that the DExD/H-box domain plays a small but measurable role in substrate binding.

FIGS. 3A-C. Binding affinity of hDcr proteins to duplex RNAs. A and B, KaleidaGraph global fitting results from filter binding assays of hDcr proteins to duplex RNAs of 37ab (3A) or pre-hlet-7 (3B). Value at each protein concentration was averaged from 2 independent filter binding assays. C, A summary of dissociation constants ($K_d$, nM) resulted from A.

DEAD-Box Domain Deletion Enhances the Catalytic Rate Constant for Dicer

Figures 4A, 4B, 4C:
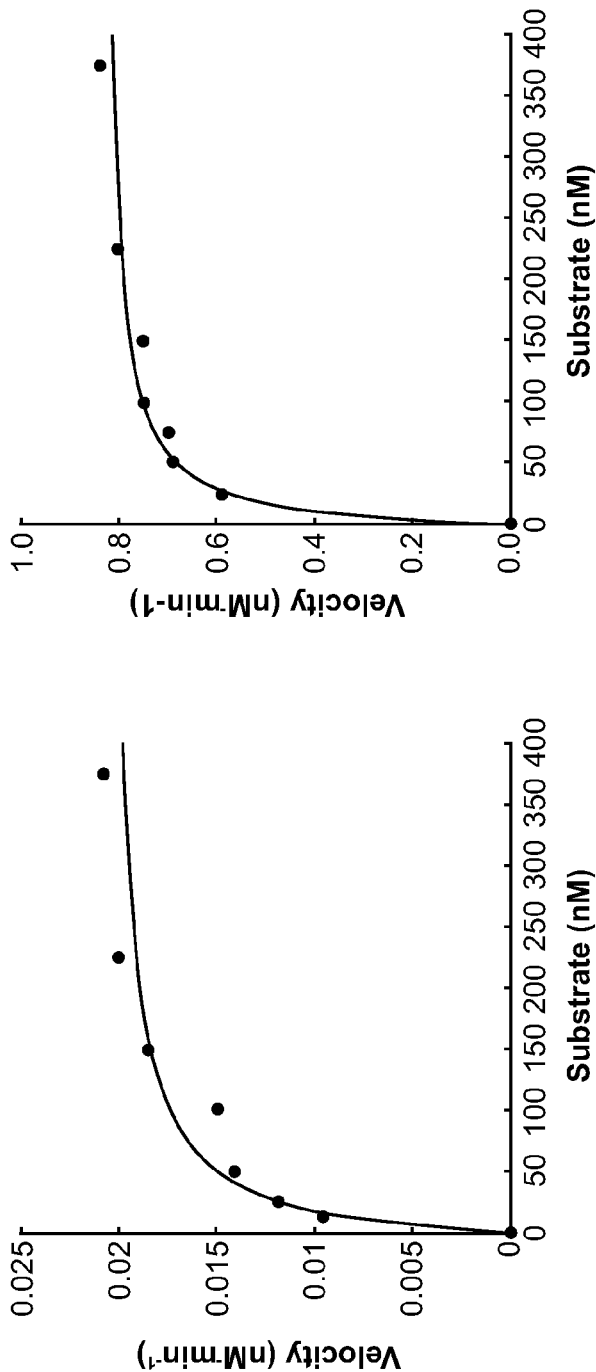
FIGS. 4A-C depict kinetic analysis of wild-type and ΔDEAD hDcr proteins.

The lack of substantial differences in hDcr substrate binding affinities, particularly for the DExD/H-box deletion protein, led us to wonder whether the enhanced rate of single-turnover catalysis by this enzyme resulted from a direct effect on the catalytic rate constant. To test this, we measured the rate of 37ab substrate cleavage using a sub-saturating amount of enzyme and various substrate concentrations. Plots of initial reaction rate ($v_o$) versus substrate concentration showed that both full-length Dicer and the DExD/H-box deletion enzyme demonstrate classical Michaelis-Menten kinetics (FIG. 4A, B). This analysis enabled determination of apparent $K_m$, $V_{max}$ and $k_{cat}$ values, as well as comparison of enzyme efficiency as revealed by $k_{cat}/K_m$ (FIG. 4C).

Figure 5:
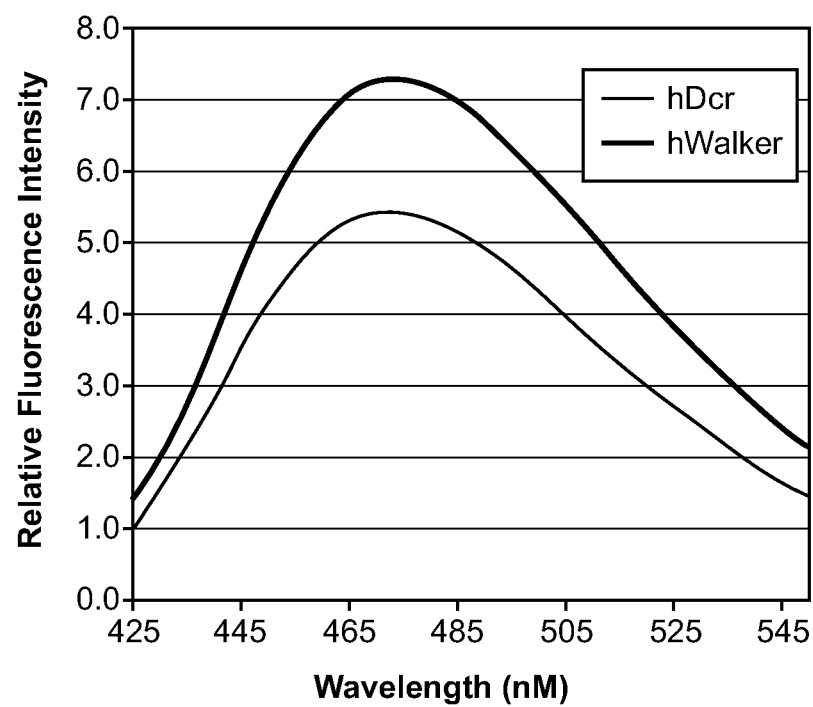
FIG. 5 depicts the results of a 1-anilino-naphthalene-8-sulfonate (ANS) binding assay.

$K_m$ and $k_{cat}$, determined from nonlinear least squares fits of $v_o$ versus substrate concentration, showed that $K_m$ values for full-length hDcr and ΔDEAD were 18.8 and 11.6 nM, respectively (FIG. 4C). In contrast, the turnover number, $k_{cat}$, increased ~40-fold as a result of DExD/H-box deletion (FIG. 4C). Thus, the ratio of $k_{cat}$ to $K_m$ ($k_{cat} K_m^{-1}$) of the ΔDEAD protein is 65-fold greater than that of full-length hDcr protein (FIG. 4C). Since this ratio is a classical measure of enzyme efficiency and corresponds to the second-order rate constant for the reaction when the concentration of substrate is much less than $K_m$ (Haley & Zamore, 2004), the DExD/H-box domain apparently plays a role in the rate of conformational changes required for formation of the enzyme-substrate complex. In support of this idea, the Walker-motif point mutant Dicer (hWalker) showed significantly increased binding to the hydrophobic interaction reagent 1-anilino-naphthalene-8-sulfonate (ANS) (FIG. 5). Because ANS binds more strongly to partially unfolded or "molten-globule" proteins (Semisotnov et al, 1991), this finding supports the conclusion that structural destabilization or rearrangement of the DExD/H-box domain triggers catalytic activation of human Dicer.

FIGS. 4A-C. Kinetic analysis of wild-type and ΔDEAD hDcr proteins. A (flhDcr) and B (ΔDEAD), plots of initial velocity versus substrate concentration. DEAD domain inhibits multiple-turnover of hDicer cleavage of the RNA target (compare A to B). C, A summary of kinetics of flhDcr and ΔDEAD. Deletion of DEAD domain made the protein about 65 folds more efficient ($k_{cat} K_m^{-1}$ of ΔDEAD over that of flhDcr).

FIG. 5. ANS binding assay. Folding status of a protein can be monitored by its binding ability to a fluorescent hydrophobic probe, ANS (1-anilino-naphthalene-8-sulfonate) since ANS has much stronger affinity to the "molten" globule intermediate state of a protein. In a 70 μl binding reaction, 5 μM of ANS and 1 μM protein were used. After 30 min incubation at room temperature, fluorescence intensity was scanned from 425 to 545 nM in the machine of FluoroMax-3 (Jobin Yvon Inc) after excited at 460 nM.

TRBP Binding Stimulates Substrate Cleavage by Full-Length Dicer

Figure 6A:
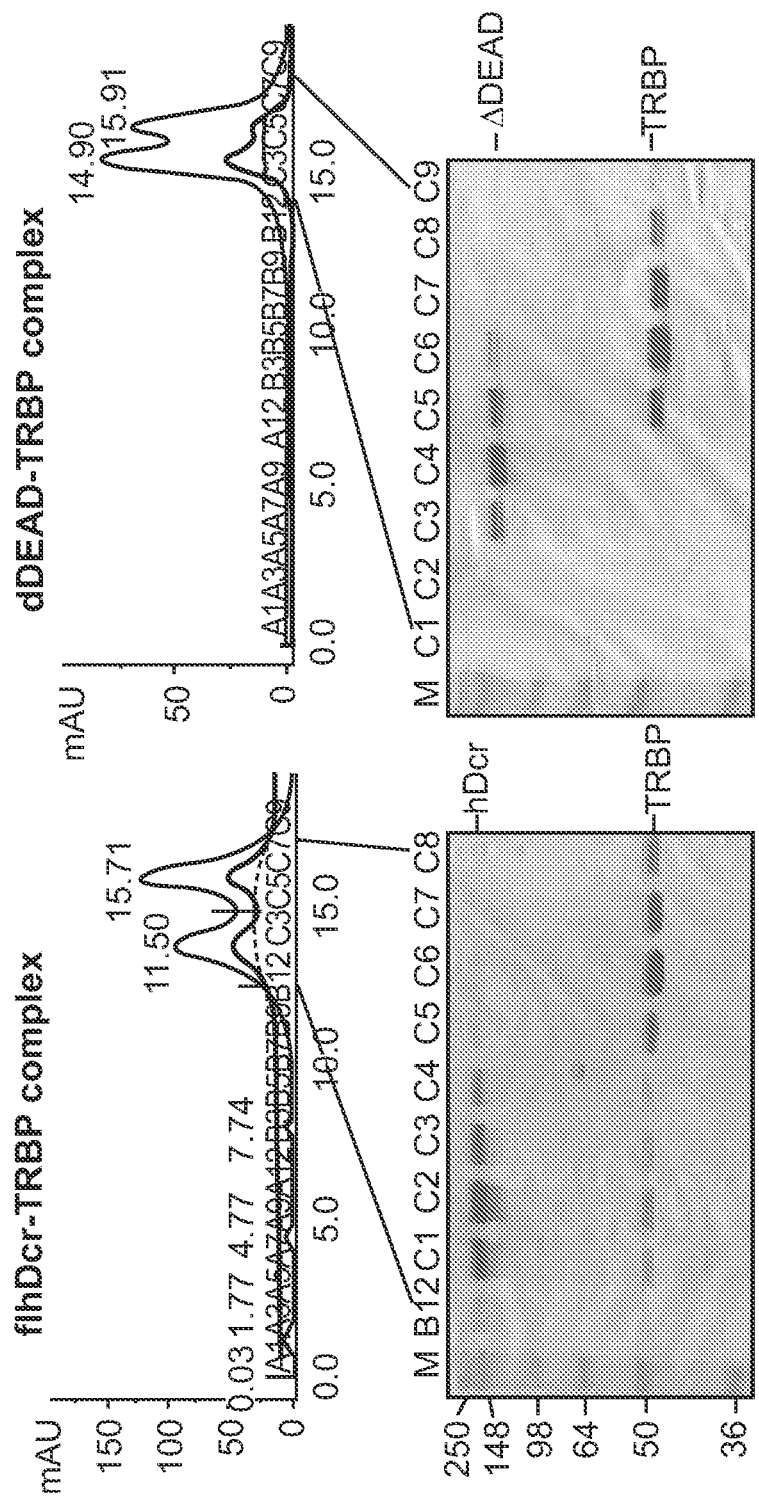
FIGS. 6A and 6B depict interaction of human Dicer with TRBP mediated by DEAD domain.

Previous experiments using immunoprecipitation showed that the DExD/H-box domain of Dicer is critical for interaction with human partner proteins TRBP and PACT (Lee et al, 2006) and the fly protein Loquacious (Logs) (Ye et al, 2007). In each case these partner proteins share homology with known RNA binding motifs and have been thought to enhance the affinity and/or specificity of Dicer for its substrates. To test whether a direct physical interaction can be observed between purified hDcr and TRBP, we used size exclusion chromatography to examine the ability of these proteins to form a stable complex. Consistent with prior immunoprecipitation data, full-length human Dicer spontaneously formed a complex with TRBP, while Dicer lacking the DExD/H-box domain (ΔDEAD) did not (FIG. 6A). Thus, the helicase motif of human Dicer is sufficient and necessary for TRBP binding to Dicer without requiring other factors.

Figure 6B:
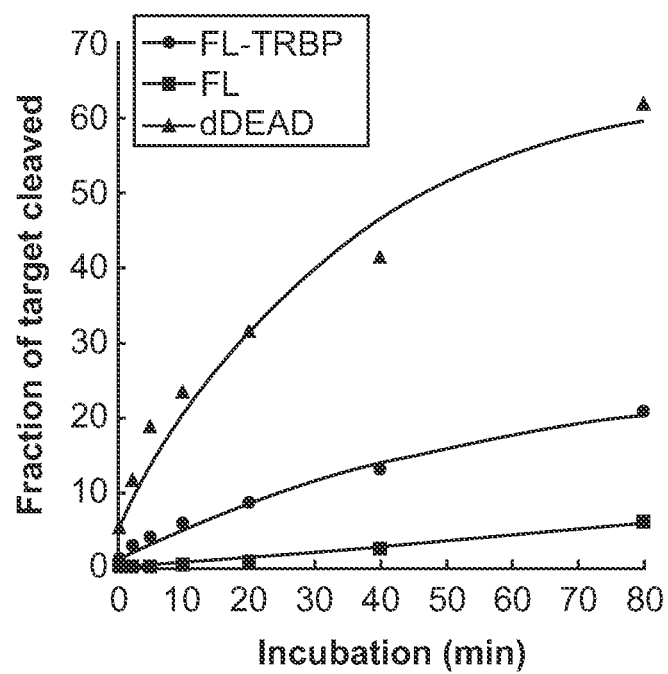

We wondered whether TRBP binding to the DExD/H-box domain might stimulate hDcr activity and thus serve as a trigger to activate dicing by the complex. To test this possibility, the dicing activity of the hDcr-TRBP complex purified by size-exclusion chromatography was compared to that of full-length hDcr or the DExD/H-box deletion protein in a multiple-turnover assay (FIG. 6B). Interestingly, we find that although not as dramatic as DExD/H-box deletion, binding of TRBP to full-length hDcr increased the cleavage rate of the resulting protein complex (FIG. 6B). It is possible that this change results from conformational changes induced in hDcr itself upon TRBP binding. This result supports our model that the presence of DExD/H-box domain makes the processing center of human Dicer less efficient/accessible, and that removal or conformational rearrangement alleviates this effect.

FIGS. 6A and 6B. Interaction of human Dicer with TRBP mediated by DEAD domain A, TRBP interacts with hDcr through DEAD domain. Prior to size exclusion chromatography, 2.5 nmol of each human Dicer protein and 9.0 nmol of TRBP were pre-incubated on ice for 60 minutes. Left panel, a chromatogram (top) of wild-type human Dicer (flhDcr) with TRBP and SDS-PAGE gel analysis of fractions (bottom); Right panel, a chromatogram (top) of ΔDEAD human Dicer (ΔDEAD) with TRBP and SDS-PAGE gel analysis of fractions (bottom). B, Binding of TRBP to hDcr increased its dicing activity. A multiple-turnover assay for 37ab cleavage using 100 nM dsRNA and 5 nM hDcr or hDcr-TRBP.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A modified Dicer polypeptide, wherein said modified Dicer polypeptide lacks at least about 200 amino acids of the DExD/H-box domain set fourth in SEQ ID NO:2, generates miRNA or siRNA from a double-stranded RNA substrate, and exhibits a $k_{cat}$ that is at least 5-fold higher than the $k_{cat}$ of a Dicer polypeptide having the amino acid sequence set fourth in SEQ ID NO:1.

2. The modified Dicer polypeptide of claim 1, wherein the modified Dicer polypeptide lacks the DExD/H-box domain.

3. The modified Dicer polypeptide of claim 2, wherein the modified Dicer polypeptide lacks an amino acid sequence having at least about 75% amino acid sequence identity with a stretch of at least 100 contiguous amino acids of amino acids 1-604 of the amino acid sequence set fourth in SEQ ID NO:2.

4. The modified Dicer polypeptide of claim 1, wherein the modified Dicer polypeptide comprises an amino acid sequence having at least about 75% amino acid sequence identity to the amino acid sequence set fourth in SEQ ID NO:3.

5. The modified Dicer polypeptide of claim 1, wherein said modified Dicer polypeptide has a $k_{cat}$ of from about $0.5 \times 10^{-1}$ $s^{-1}$ to about $1.0 \times 10^{-5}$ $s^{-1}$.

6. A composition comprising: a) the modified Dicer polypeptide of claim 1; and b) a buffer.

7. A nucleic acid comprising a nucleotide sequence encoding a subject modified Dicer polypeptide of claim 1.

8. The nucleic acid of claim 7, wherein said nucleic acid is a recombinant expression construct.

9. A genetically modified host cell comprising the nucleic acid of claim 7.

10. The genetically modified host cell of claim 9, wherein said host cell is a prokaryotic host cell.

11. The genetically modified host cell of claim 9, wherein said host cell is a eukaryotic host cell.

12. A method of producing the modified Dicer polypeptide of claim 1, the method comprising:
a) culturing the genetically modified host cell of claim 9 in culture medium in vitro under conditions such that the cell produces the modified Dicer polypeptide; and
b) recovering the modified Dicer polypeptide produced by the cell.

13. A method of producing an siRNA, the method comprising contacting the modified Dicer polypeptide of claim 1 with a double-stranded RNA (dsRNA) substrate, wherein the modified Dicer polypeptide cleaves the dsRNA substrate, thereby producing an siRNA.

14. The method of claim 13, wherein the siRNA has a length of from about 21 to about 23 nucleotides.

15. The modified Dicer polypeptide of claim 1, wherein the modified Dicer polypeptide comprises an amino acid sequence having at least about 95% amino acid sequence identity to the amino acid sequence set forth in SEQ ID NO:3.

16. The modified Dicer polypeptide of claim 15, wherein the modified Dicer polypeptide has a length of from about 1100 amino acids to about 1320 amino acids.

17. The modified Dicer polypeptide of claim 15, wherein the modified Dicer polypeptide exhibits a $k_{cat}$ that is at least 10-fold higher than the $k_{cat}$ of a Dicer polypeptide having the amino acid sequence set forth in SEQ ID NO:1.

18. The modified Dicer polypeptide of claim 15, wherein the modified Dicer polypeptide exhibits a $k_{cat}$ that is at least 40-fold higher than the $k_{cat}$ of a Dicer polypeptide having the amino acid sequence set forth in SEQ ID NO:1.

* * * * *

SEQUENCE LISTING

<160> NUMBER OF SEQ ID NOS: 25

<210> SEQ ID NO 1
<211> LENGTH: 1922
<212> TYPE: PRT
<213> ORGANISM: Homo sapiens

<400> SEQUENCE: 1

```
Met Lys Ser Pro Ala Leu Gln Pro Leu Ser Met Ala Gly Leu Gln Leu
 1               5                  10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Val Leu Leu Thr Lys Glu
65                  70                  75                  80

Leu Ser Tyr Gln Ile Arg Gly Asp Phe Ser Arg Asn Gly Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asn Leu Glu
        115                 120                 125

Val Asn Ala Ser Trp Thr Lys Glu Arg Trp Asn Gln Glu Phe Thr Lys
    130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Glu Asn Cys Pro Ser Cys Pro Arg Ile Leu Gly Leu Thr Ala Ser
        195                 200                 205

Ile Leu Asn Gly Lys Cys Asp Pro Glu Glu Leu Glu Glu Lys Ile Gln
    210                 215                 220

Lys Leu Glu Lys Ile Leu Lys Ser Asn Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
            260                 265                 270

Glu Leu Glu Glu Ala Leu Asn Phe Ile Asn Asp Cys Asn Ile Ser Val
        275                 280                 285

His Ser Lys Glu Arg Asp Ser Thr Leu Ile Ser Lys Gln Ile Leu Ser
    290                 295                 300

Asp Cys Arg Ala Val Leu Val Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Phe Leu
            340                 345                 350

Arg Lys Ile His Ala Leu Cys Glu Glu His Phe Ser Pro Ala Ser Leu
        355                 360                 365
```

-continued

```
Asp Leu Lys Phe Val Thr Pro Lys Val Ile Lys Leu Glu Ile Leu
    370                 375                 380
Arg Lys Tyr Lys Pro Tyr Glu Arg Gln Gln Phe Glu Ser Val Glu Trp
385                 390                 395                 400
Tyr Asn Asn Arg Asn Gln Asp Asn Tyr Val Ser Trp Ser Asp Ser Glu
                405                 410                 415
Asp Asp Asp Glu Asp Glu Glu Ile Glu Glu Lys Glu Lys Pro Glu Thr
            420                 425                 430
Asn Phe Pro Ser Pro Phe Thr Asn Ile Leu Cys Gly Ile Ile Phe Val
        435                 440                 445
Glu Arg Arg Tyr Thr Ala Val Val Leu Asn Arg Leu Ile Lys Glu Ala
    450                 455                 460
Gly Lys Gln Asp Pro Glu Leu Ala Tyr Ile Ser Ser Asn Phe Ile Thr
465                 470                 475                 480
Gly His Gly Ile Gly Lys Asn Gln Pro Arg Asn Lys Gln Met Glu Ala
                485                 490                 495
Glu Phe Arg Lys Gln Glu Val Leu Arg Lys Phe Arg Ala His Glu
            500                 505                 510
Thr Asn Leu Leu Ile Ala Thr Ser Ile Val Glu Glu Gly Val Asp Ile
        515                 520                 525
Pro Lys Cys Asn Leu Val Val Arg Phe Asp Leu Pro Thr Glu Tyr Arg
    530                 535                 540
Ser Tyr Val Gln Ser Lys Gly Arg Ala Arg Ala Pro Ile Ser Asn Tyr
545                 550                 555                 560
Ile Met Leu Ala Asp Thr Asp Lys Ile Lys Ser Phe Glu Glu Asp Leu
                565                 570                 575
Lys Thr Tyr Lys Ala Ile Glu Lys Ile Leu Arg Asn Lys Cys Ser Lys
            580                 585                 590
Ser Val Asp Thr Gly Glu Thr Asp Ile Asp Pro Val Met Asp Asp Asp
        595                 600                 605
Asp Val Phe Pro Pro Tyr Val Leu Arg Pro Asp Asp Gly Gly Pro Arg
    610                 615                 620
Val Thr Ile Asn Thr Ala Ile Gly His Ile Asn Arg Tyr Cys Ala Arg
625                 630                 635                 640
Leu Pro Ser Asp Pro Phe Thr His Leu Ala Pro Lys Cys Arg Thr Arg
                645                 650                 655
Glu Leu Pro Asp Gly Thr Phe Tyr Ser Thr Leu Tyr Leu Pro Ile Asn
            660                 665                 670
Ser Pro Leu Arg Ala Ser Ile Val Gly Pro Pro Met Ser Cys Val Arg
        675                 680                 685
Leu Ala Glu Arg Val Val Ala Leu Ile Cys Cys Glu Lys Leu His Lys
    690                 695                 700
Ile Gly Glu Leu Asp Asp His Leu Met Pro Val Gly Lys Glu Thr Val
705                 710                 715                 720
Lys Tyr Glu Glu Glu Leu Asp Leu His Asp Glu Glu Thr Ser Val
                725                 730                 735
Pro Gly Arg Pro Gly Ser Thr Lys Arg Arg Gln Cys Tyr Pro Lys Ala
            740                 745                 750
Ile Pro Glu Cys Leu Arg Asp Ser Tyr Pro Arg Pro Asp Gln Pro Cys
        755                 760                 765
Tyr Leu Tyr Val Ile Gly Met Val Leu Thr Thr Pro Leu Pro Asp Glu
    770                 775                 780
Leu Asn Phe Arg Arg Arg Lys Leu Tyr Pro Pro Glu Asp Thr Thr Arg
```

-continued

```
           785                 790                 795                 800
    Cys Phe Gly Ile Leu Thr Ala Lys Pro Ile Pro Gln Ile Pro His Phe
                        805                 810                 815
    Pro Val Tyr Thr Arg Ser Gly Glu Val Thr Ile Ser Ile Glu Leu Lys
                        820                 825                 830
    Lys Ser Gly Phe Met Leu Ser Leu Gln Met Leu Glu Leu Ile Thr Arg
                        835                 840                 845
    Leu His Gln Tyr Ile Phe Ser His Ile Leu Arg Leu Glu Lys Pro Ala
            850                 855                 860
    Leu Glu Phe Lys Pro Thr Asp Ala Asp Ser Ala Tyr Cys Val Leu Pro
    865                 870                 875                 880
    Leu Asn Val Val Asn Asp Ser Ser Thr Leu Asp Ile Asp Phe Lys Phe
                        885                 890                 895
    Met Glu Asp Ile Glu Lys Ser Glu Ala Arg Ile Gly Ile Pro Ser Thr
                        900                 905                 910
    Lys Tyr Thr Lys Glu Thr Pro Phe Val Phe Lys Leu Gly Asp Tyr Gln
                        915                 920                 925
    Asp Ala Val Ile Ile Pro Arg Tyr Arg Asn Phe Asp Gln Pro His Arg
            930                 935                 940
    Phe Tyr Val Ala Asp Val Tyr Thr Asp Leu Thr Pro Leu Ser Lys Phe
    945                 950                 955                 960
    Pro Ser Pro Glu Tyr Glu Thr Phe Ala Glu Tyr Lys Thr Lys Tyr
                        965                 970                 975
    Asn Leu Asp Leu Thr Asn Leu Asn Gln Pro Leu Leu Ser Val Asp His
                        980                 985                 990
    Thr Ser Ser Arg Leu Asn Leu Leu Thr Pro Arg His Leu Asn Gln Lys
                        995                1000                1005
    Gly Lys Ala Leu Pro Leu Ser Ser Ala Glu Lys Arg Lys Ala Lys
           1010                1015                1020
    Trp Glu Ser Leu Gln Asn Lys Gln Ile Leu Val Pro Glu Leu Cys
           1025                1030                1035
    Ala Ile His Pro Ile Pro Ala Ser Leu Trp Arg Lys Ala Val Cys
           1040                1045                1050
    Leu Pro Ser Ile Leu Tyr Arg Leu His Cys Leu Leu Thr Ala Glu
           1055                1060                1065
    Glu Leu Arg Ala Gln Thr Ala Ser Asp Ala Gly Val Gly Val Arg
           1070                1075                1080
    Ser Leu Pro Ala Asp Phe Arg Tyr Pro Asn Leu Asp Phe Gly Trp
           1085                1090                1095
    Lys Lys Ser Ile Asp Ser Lys Ser Phe Ile Ser Ile Ser Asn Ser
           1100                1105                1110
    Ser Ser Ala Glu Asn Asp Asn Tyr Cys Lys His Ser Thr Ile Val
           1115                1120                1125
    Pro Glu Asn Ala Ala His Gln Gly Ala Asn Arg Thr Ser Ser Leu
           1130                1135                1140
    Glu Asn His Asp Gln Met Ser Val Asn Cys Arg Thr Leu Leu Ser
           1145                1150                1155
    Glu Ser Pro Gly Lys Leu His Val Glu Val Ser Ala Asp Leu Thr
           1160                1165                1170
    Ala Ile Asn Gly Leu Ser Tyr Asn Gln Asn Leu Ala Asn Gly Ser
           1175                1180                1185
    Tyr Asp Leu Ala Asn Arg Asp Phe Cys Gln Gly Asn Gln Leu Asn
           1190                1195                1200
```

-continued

```
Tyr Tyr Lys Gln Glu Ile Pro Val Gln Pro Thr Thr Ser Tyr Ser
1205                1210                1215

Ile Gln Asn Leu Tyr Ser Tyr Glu Asn Gln Pro Gln Pro Ser Asp
1220                1225                1230

Glu Cys Thr Leu Leu Ser Asn Lys Tyr Leu Asp Gly Asn Ala Asn
1235                1240                1245

Lys Ser Thr Ser Asp Gly Ser Pro Val Met Ala Val Met Pro Gly
1250                1255                1260

Thr Thr Asp Thr Ile Gln Val Leu Lys Gly Arg Met Asp Ser Glu
1265                1270                1275

Gln Ser Pro Ser Ile Gly Tyr Ser Ser Arg Thr Leu Gly Pro Asn
1280                1285                1290

Pro Gly Leu Ile Leu Gln Ala Leu Thr Leu Ser Asn Ala Ser Asp
1295                1300                1305

Gly Phe Asn Leu Glu Arg Leu Glu Met Leu Gly Asp Ser Phe Leu
1310                1315                1320

Lys His Ala Ile Thr Thr Tyr Leu Phe Cys Thr Tyr Pro Asp Ala
1325                1330                1335

His Glu Gly Arg Leu Ser Tyr Met Arg Ser Lys Lys Val Ser Asn
1340                1345                1350

Cys Asn Leu Tyr Arg Leu Gly Lys Lys Lys Gly Leu Pro Ser Arg
1355                1360                1365

Met Val Val Ser Ile Phe Asp Pro Pro Val Asn Trp Leu Pro Pro
1370                1375                1380

Gly Tyr Val Val Asn Gln Asp Lys Ser Asn Thr Asp Lys Trp Glu
1385                1390                1395

Lys Asp Glu Met Thr Lys Asp Cys Met Leu Ala Asn Gly Lys Leu
1400                1405                1410

Asp Glu Asp Tyr Glu Glu Glu Asp Glu Glu Glu Ser Leu Met
1415                1420                1425

Trp Arg Ala Pro Lys Glu Glu Ala Asp Tyr Glu Asp Asp Phe Leu
1430                1435                1440

Glu Tyr Asp Gln Glu His Ile Arg Phe Ile Asp Asn Met Leu Met
1445                1450                1455

Gly Ser Gly Ala Phe Val Lys Lys Ile Ser Leu Ser Pro Phe Ser
1460                1465                1470

Thr Thr Asp Ser Ala Tyr Glu Trp Lys Met Pro Lys Lys Ser Ser
1475                1480                1485

Leu Gly Ser Met Pro Phe Ser Ser Asp Phe Glu Asp Phe Asp Tyr
1490                1495                1500

Ser Ser Trp Asp Ala Met Cys Tyr Leu Asp Pro Ser Lys Ala Val
1505                1510                1515

Glu Glu Asp Asp Phe Val Val Gly Phe Trp Asn Pro Ser Glu Glu
1520                1525                1530

Asn Cys Gly Val Asp Thr Gly Lys Gln Ser Ile Ser Tyr Asp Leu
1535                1540                1545

His Thr Glu Gln Cys Ile Ala Asp Lys Ser Ile Ala Asp Cys Val
1550                1555                1560

Glu Ala Leu Leu Gly Cys Tyr Leu Thr Ser Cys Gly Glu Arg Ala
1565                1570                1575

Ala Gln Leu Phe Leu Cys Ser Leu Gly Leu Lys Val Leu Pro Val
1580                1585                1590

Ile Lys Arg Thr Asp Arg Glu Lys Ala Leu Cys Pro Thr Arg Glu
1595                1600                1605
```

| | | | | | | | | | | |
|---|---|---|---|---|---|---|---|---|---|---|
| Asn | Phe | Asn | Ser | Gln | Gln | Lys | Asn | Leu | Ser | Val | Ser | Cys | Ala | Ala |
| | 1610 | | | | 1615 | | | | 1620 | |

Asn Phe Asn Ser Gln Gln Lys Asn Leu Ser Val Ser Cys Ala Ala
    1610                1615                1620

Ala Ser Val Ala Ser Ser Arg Ser Ser Val Leu Lys Asp Ser Glu
1625                1630                1635

Tyr Gly Cys Leu Lys Ile Pro Pro Arg Cys Met Phe Asp His Pro
1640                1645                1650

Asp Ala Asp Lys Thr Leu Asn His Leu Ile Ser Gly Phe Glu Asn
    1655                1660                1665

Phe Glu Lys Lys Ile Asn Tyr Arg Phe Lys Asn Lys Ala Tyr Leu
    1670                1675                1680

Leu Gln Ala Phe Thr His Ala Ser Tyr His Tyr Asn Thr Ile Thr
    1685                1690                1695

Asp Cys Tyr Gln Arg Leu Glu Phe Leu Gly Asp Ala Ile Leu Asp
    1700                1705                1710

Tyr Leu Ile Thr Lys His Leu Tyr Glu Asp Pro Arg Gln His Ser
    1715                1720                1725

Pro Gly Val Leu Thr Asp Leu Arg Ser Ala Leu Val Asn Asn Thr
    1730                1735                1740

Ile Phe Ala Ser Leu Ala Val Lys Tyr Asp Tyr His Lys Tyr Phe
    1745                1750                1755

Lys Ala Val Ser Pro Glu Leu Phe His Val Ile Asp Asp Phe Val
    1760                1765                1770

Gln Phe Gln Leu Glu Lys Asn Glu Met Gln Gly Met Asp Ser Glu
    1775                1780                1785

Leu Arg Arg Ser Glu Glu Asp Glu Glu Lys Glu Glu Asp Ile Glu
    1790                1795                1800

Val Pro Lys Ala Met Gly Asp Ile Phe Glu Ser Leu Ala Gly Ala
    1805                1810                1815

Ile Tyr Met Asp Ser Gly Met Ser Leu Glu Thr Val Trp Gln Val
    1820                1825                1830

Tyr Tyr Pro Met Met Arg Pro Leu Ile Glu Lys Phe Ser Ala Asn
    1835                1840                1845

Val Pro Arg Ser Pro Val Arg Glu Leu Leu Glu Met Glu Pro Glu
    1850                1855                1860

Thr Ala Lys Phe Ser Pro Ala Glu Arg Thr Tyr Asp Gly Lys Val
    1865                1870                1875

Arg Val Thr Val Glu Val Val Gly Lys Gly Lys Phe Lys Gly Val
    1880                1885                1890

Gly Arg Ser Tyr Arg Ile Ala Lys Ser Ala Ala Ala Arg Arg Ala
    1895                1900                1905

Leu Arg Ser Leu Lys Ala Asn Gln Pro Gln Val Pro Asn Ser
    1910                1915                1920

<210> SEQ ID NO 2
<211> LENGTH: 604
<212> TYPE: PRT
<213> ORGANISM: Artificial Sequence
<220> FEATURE:
<223> OTHER INFORMATION: Synthetic polypeptide

<400> SEQUENCE: 2

Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

-continued

```
Gln Gln Glu Ala Ile His Asp Asn Ile Tyr Thr Pro Arg Lys Tyr Gln
        35                  40                  45
Val Glu Leu Leu Glu Ala Ala Leu Asp His Asn Thr Ile Val Cys Leu
 50                  55                  60
Asn Thr Gly Ser Gly Lys Thr Phe Ile Ala Val Leu Leu Thr Lys Glu
 65                  70                  75                  80
Leu Ser Tyr Gln Ile Arg Gly Asp Phe Ser Arg Asn Gly Lys Arg Thr
                 85                  90                  95
Val Phe Leu Val Asn Ser Ala Asn Gln Val Ala Gln Gln Val Ser Ala
                100                 105                 110
Val Arg Thr His Ser Asp Leu Lys Val Gly Glu Tyr Ser Asn Leu Glu
            115                 120                 125
Val Asn Ala Ser Trp Thr Lys Glu Arg Trp Asn Gln Glu Phe Thr Lys
130                 135                 140
His Gln Val Leu Ile Met Thr Cys Tyr Val Ala Leu Asn Val Leu Lys
145                 150                 155                 160
Asn Gly Tyr Leu Ser Leu Ser Asp Ile Asn Leu Leu Val Phe Asp Glu
                165                 170                 175
Cys His Leu Ala Ile Leu Asp His Pro Tyr Arg Glu Ile Met Lys Leu
            180                 185                 190
Cys Glu Asn Cys Pro Ser Cys Pro Arg Ile Leu Gly Leu Thr Ala Ser
            195                 200                 205
Ile Leu Asn Gly Lys Cys Asp Pro Glu Glu Leu Glu Glu Lys Ile Gln
210                 215                 220
Lys Leu Glu Lys Ile Leu Lys Ser Asn Ala Glu Thr Ala Thr Asp Leu
225                 230                 235                 240
Val Val Leu Asp Arg Tyr Thr Ser Gln Pro Cys Glu Ile Val Val Asp
                245                 250                 255
Cys Gly Pro Phe Thr Asp Arg Ser Gly Leu Tyr Glu Arg Leu Leu Met
            260                 265                 270
Glu Leu Glu Glu Ala Leu Asn Phe Ile Asn Asp Cys Asn Ile Ser Val
            275                 280                 285
His Ser Lys Glu Arg Asp Ser Thr Leu Ile Ser Lys Gln Ile Leu Ser
290                 295                 300
Asp Cys Arg Ala Val Leu Val Val Leu Gly Pro Trp Cys Ala Asp Lys
305                 310                 315                 320
Val Ala Gly Met Met Val Arg Glu Leu Gln Lys Tyr Ile Lys His Glu
                325                 330                 335
Gln Glu Glu Leu His Arg Lys Phe Leu Leu Phe Thr Asp Thr Phe Leu
            340                 345                 350
Arg Lys Ile His Ala Leu Cys Glu Glu His Phe Ser Pro Ala Ser Leu
            355                 360                 365
Asp Leu Lys Phe Val Thr Pro Lys Val Ile Lys Leu Leu Glu Ile Leu
370                 375                 380
Arg Lys Tyr Lys Pro Tyr Glu Arg Gln Gln Phe Glu Ser Val Glu Trp
385                 390                 395                 400
Tyr Asn Asn Arg Asn Gln Asp Asn Tyr Val Ser Trp Ser Asp Ser Glu
                405                 410                 415
Asp Asp Asp Glu Asp Glu Glu Ile Glu Glu Lys Glu Lys Pro Glu Thr
            420                 425                 430
Asn Phe Pro Ser Pro Phe Thr Asn Ile Leu Cys Gly Ile Ile Phe Val
            435                 440                 445
Glu Arg Arg Tyr Thr Ala Val Val Leu Asn Arg Leu Ile Lys Glu Ala
450                 455                 460
```

```
Gly Lys Gln Asp Pro Glu Leu Ala Tyr Ile Ser Ser Asn Phe Ile Thr
465                 470                 475                 480

Gly His Gly Ile Gly Lys Asn Gln Pro Arg Asn Lys Gln Met Glu Ala
            485                 490                 495

Glu Phe Arg Lys Gln Glu Val Leu Arg Lys Phe Arg Ala His Glu
        500                 505                 510

Thr Asn Leu Leu Ile Ala Thr Ser Ile Val Glu Glu Gly Val Asp Ile
            515                 520                 525

Pro Lys Cys Asn Leu Val Val Arg Phe Asp Leu Pro Thr Glu Tyr Arg
530                 535                 540

Ser Tyr Val Gln Ser Lys Gly Arg Ala Arg Ala Pro Ile Ser Asn Tyr
545                 550                 555                 560

Ile Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
            580                 585                 590

Ser Val Asp Thr Gly Glu Thr Asp Ile Asp Pro Val
            595                 600

<210> SEQ ID NO 3
<211> LENGTH: 1318
<212> TYPE: PRT
<213> ORGANISM: Artificial Sequence
<220> FEATURE:
<223> OTHER INFORMATION: Synthetic polypeptide

<400> SEQUENCE: 3

Met Asp Asp Asp Val Phe Pro Tyr Val Leu Arg Pro Asp Asp
1               5                   10                  15

Gly Gly Pro Arg Val Thr Ile Asn Thr Ala Ile Gly His Ile Asn Arg
                20                  25                  30

Tyr Cys Ala Arg Leu Pro Ser Asp Pro Phe Thr His Leu Ala Pro Lys
            35                  40                  45

Cys Arg Thr Arg Glu Leu Pro Asp Gly Thr Phe Tyr Ser Thr Leu Tyr
        50                  55                  60

Leu Pro Ile Asn Ser Pro Leu Arg Ala Ser Ile Val Gly Pro Pro Met
65                  70                  75                  80

Ser Cys Val Arg Leu Ala Glu Arg Val Val Ala Leu Ile Cys Cys Glu
                85                  90                  95

Lys Leu His Lys Ile Gly Glu Leu Asp Asp His Leu Met Pro Val Gly
            100                 105                 110

Lys Glu Thr Val Lys Tyr Glu Glu Leu Asp Leu His Asp Glu Glu
        115                 120                 125

Glu Thr Ser Val Pro Gly Arg Pro Gly Ser Thr Lys Arg Arg Gln Cys
        130                 135                 140

Tyr Pro Lys Ala Ile Pro Glu Cys Leu Arg Asp Ser Tyr Pro Arg Pro
145                 150                 155                 160

Asp Gln Pro Cys Tyr Leu Tyr Val Ile Gly Met Val Leu Thr Thr Pro
                165                 170                 175

Leu Pro Asp Glu Leu Asn Phe Arg Arg Arg Lys Leu Tyr Pro Pro Glu
            180                 185                 190

Asp Thr Thr Arg Cys Phe Gly Ile Leu Thr Ala Lys Pro Ile Pro Gln
        195                 200                 205

Ile Pro His Phe Pro Val Tyr Thr Arg Ser Gly Glu Val Thr Ile Ser
        210                 215                 220
```

```
Ile Glu Leu Lys Lys Ser Gly Phe Met Leu Ser Leu Gln Met Leu Glu
225                 230                 235                 240

Leu Ile Thr Arg Leu His Gln Tyr Ile Phe Ser His Ile Leu Arg Leu
            245                 250                 255

Glu Lys Pro Ala Leu Glu Phe Lys Pro Thr Asp Ala Asp Ser Ala Tyr
        260                 265                 270

Cys Val Leu Pro Leu Asn Val Val Asn Asp Ser Ser Thr Leu Asp Ile
    275                 280                 285

Asp Phe Lys Phe Met Glu Asp Ile Glu Lys Ser Glu Ala Arg Ile Gly
290                 295                 300

Ile Pro Ser Thr Lys Tyr Thr Lys Glu Thr Pro Phe Val Phe Lys Leu
305                 310                 315                 320

Glu Asp Tyr Gln Asp Ala Val Ile Ile Pro Arg Tyr Arg Asn Phe Asp
                325                 330                 335

Gln Pro His Arg Phe Tyr Val Ala Asp Val Tyr Thr Asp Leu Thr Pro
            340                 345                 350

Leu Ser Lys Phe Pro Ser Pro Glu Tyr Glu Thr Phe Ala Glu Tyr Tyr
        355                 360                 365

Lys Thr Lys Tyr Asn Leu Asp Leu Thr Asn Leu Asn Gln Pro Leu Leu
370                 375                 380

Asp Val Asp His Thr Ser Ser Arg Leu Asn Leu Leu Thr Pro Arg His
385                 390                 395                 400

Leu Asn Gln Lys Gly Lys Ala Leu Pro Leu Ser Ser Ala Glu Lys Arg
                405                 410                 415

Lys Ala Lys Trp Glu Ser Leu Gln Asn Lys Gln Ile Leu Val Pro Glu
            420                 425                 430

Leu Cys Ala Ile His Pro Ile Pro Ala Ser Leu Trp Arg Lys Ala Val
        435                 440                 445

Cys Leu Pro Ser Ile Leu Tyr Arg Leu His Cys Leu Leu Thr Ala Glu
    450                 455                 460

Glu Leu Arg Ala Gln Thr Ala Ser Asp Ala Gly Val Gly Val Arg Ser
465                 470                 475                 480

Leu Pro Ala Asp Phe Arg Tyr Pro Asn Leu Asp Phe Gly Trp Lys Lys
                485                 490                 495

Ser Ile Asp Ser Lys Ser Phe Ile Ser Ile Ser Asn Ser Ser Ser Ala
            500                 505                 510

Glu Asn Asp Asn Tyr Cys Lys His Ser Thr Ile Val Pro Glu Asn Ala
        515                 520                 525

Ala His Gln Gly Ala Asn Arg Thr Ser Ser Leu Glu Asn His Asp Gln
    530                 535                 540

Met Ser Val Asn Cys Arg Thr Leu Leu Ser Glu Ser Pro Gly Lys Leu
545                 550                 555                 560

His Val Glu Val Ser Ala Asp Leu Thr Ala Ile Asn Gly Leu Ser Tyr
                565                 570                 575

Asn Gln Asn Leu Ala Asn Gly Ser Tyr Asp Leu Ala Asn Arg Asp Phe
            580                 585                 590

Cys Gln Gly Asn Gln Leu Asn Tyr Tyr Lys Gln Glu Ile Pro Val Gln
        595                 600                 605

Pro Thr Thr Ser Tyr Ser Ile Gln Asn Leu Tyr Ser Tyr Glu Asn Gln
    610                 615                 620

Pro Gln Pro Ser Asp Glu Cys Thr Leu Leu Ser Asn Lys Tyr Leu Asp
625                 630                 635                 640

Gly Asn Ala Asn Lys Ser Thr Ser Asp Gly Ser Pro Val Met Ala Val
                645                 650                 655
```

```
Met Pro Gly Thr Thr Asp Thr Ile Gln Val Leu Lys Gly Arg Met Asp
            660                 665                 670
Ser Glu Gln Ser Pro Ser Ile Gly Tyr Ser Ser Arg Thr Leu Gly Pro
        675                 680                 685
Asn Pro Gly Leu Ile Leu Gln Ala Leu Thr Leu Ser Asn Ala Ser Asp
690                 695                 700
Gly Phe Asn Leu Glu Arg Leu Glu Met Leu Gly Asp Ser Phe Leu Lys
705                 710                 715                 720
His Ala Ile Thr Thr Tyr Leu Phe Cys Thr Tyr Pro Asp Ala His Glu
                725                 730                 735
Gly Arg Leu Ser Tyr Met Arg Ser Lys Lys Val Ser Asn Cys Asn Leu
            740                 745                 750
Tyr Arg Leu Gly Lys Lys Lys Gly Leu Pro Ser Arg Met Val Val Ser
        755                 760                 765
Ile Phe Asp Pro Pro Val Asn Trp Leu Pro Pro Gly Tyr Val Val Asn
770                 775                 780
Gln Asp Lys Ser Asn Thr Asp Lys Trp Glu Lys Asp Glu Met Thr Lys
785                 790                 795                 800
Asp Cys Met Leu Ala Asn Gly Lys Leu Asp Glu Asp Tyr Glu Glu Glu
                805                 810                 815
Asp Glu Glu Glu Ser Leu Met Trp Arg Ala Pro Lys Glu Glu Ala
            820                 825                 830
Asp Tyr Glu Asp Asp Phe Leu Glu Tyr Asp Gln Glu His Ile Arg Phe
        835                 840                 845
Ile Asp Asn Met Leu Met Gly Ser Gly Ala Phe Val Lys Lys Ile Ser
850                 855                 860
Leu Ser Pro Phe Ser Thr Thr Asp Ser Ala Tyr Glu Trp Lys Met Pro
865                 870                 875                 880
Lys Lys Ser Ser Leu Gly Ser Met Pro Phe Ser Ser Asp Phe Glu Asp
                885                 890                 895
Phe Asp Tyr Ser Ser Trp Asp Ala Met Cys Tyr Leu Asp Pro Ser Lys
            900                 905                 910
Ala Val Glu Glu Asp Asp Phe Val Val Gly Phe Trp Asn Pro Ser Glu
        915                 920                 925
Glu Asn Cys Gly Val Asp Thr Gly Lys Gln Ser Ile Ser Tyr Asp Leu
930                 935                 940
His Thr Glu Gln Cys Ile Ala Asp Lys Ser Ile Ala Asp Cys Val Glu
945                 950                 955                 960
Ala Leu Leu Gly Cys Tyr Leu Thr Ser Cys Gly Glu Arg Ala Ala Gln
                965                 970                 975
Leu Phe Leu Cys Ser Leu Gly Leu Lys Val Leu Pro Val Ile Lys Arg
            980                 985                 990
Thr Asp Arg Glu Lys Ala Leu Cys  Pro Thr Arg Glu Asn  Phe Asn Ser
        995                 1000                1005
Gln Gln  Lys Asn Leu Ser Val  Ser Cys Ala Ala Ala  Ser Val Ala
   1010                 1015                1020
Ser Ser  Arg Ser Ser Val Leu  Lys Asp Ser Glu Tyr  Gly Cys Leu
   1025                 1030                1035
Lys Ile  Pro Pro Arg Cys Met  Phe Asp His Pro Asp  Ala Asp Lys
   1040                 1045                1050
Thr Leu  Asn His Leu Ile Ser  Gly Phe Glu Asn Phe  Glu Lys Lys
   1055                 1060                1065
Ile Asn  Tyr Arg Phe Lys Asn  Lys Ala Tyr Leu Leu  Gln Ala Phe
```

```
                    1070              1075              1080

Thr His  Ala Ser Tyr His  Tyr Asn Thr Ile  Thr Asp Cys Tyr Gln
        1085             1090             1095

Arg Leu  Glu Phe Leu Gly  Asp Ala Ile Leu  Asp Tyr Leu Ile Thr
    1100             1105             1110

Lys His  Leu Tyr Glu Asp  Pro Arg Gln His  Ser Pro Gly Val Leu
    1115             1120             1125

Thr Asp  Leu Arg Ser Ala  Leu Val Asn Asn  Thr Ile Phe Ala Ser
    1130             1135             1140

Leu Ala  Val Lys Tyr Asp  Tyr His Lys Tyr  Phe Lys Ala Val Ser
    1145             1150             1155

Pro Glu  Leu Phe His Val  Ile Asp Asp Phe  Val Gln Phe Gln Leu
    1160             1165             1170

Glu Lys  Asn Glu Met Gln  Gly Met Asp Ser  Glu Leu Arg Arg Ser
    1175             1180             1185

Glu Glu  Asp Glu Glu Lys  Glu Glu Asp Ile  Glu Val Pro Lys Ala
    1190             1195             1200

Met Gly  Asp Ile Phe Glu  Ser Leu Ala Gly  Ala Ile Tyr Met Asp
    1205             1210             1215

Ser Gly  Met Ser Leu Glu  Thr Val Trp Gln  Val Tyr Tyr Pro Met
    1220             1225             1230

Met Arg  Pro Leu Ile Glu  Lys Phe Ser Ala  Asn Val Pro Arg Ser
    1235             1240             1245

Pro Val  Arg Glu Leu Leu  Glu Met Glu Pro  Glu Thr Ala Lys Phe
    1250             1255             1260

Ser Pro  Ala Glu Arg Thr  Tyr Asp Gly Lys  Val Arg Val Thr Val
    1265             1270             1275

Glu Val  Val Gly Lys Gly  Lys Phe Lys Gly  Val Gly Arg Ser Tyr
    1280             1285             1290

Arg Ile  Ala Lys Ser Ala  Ala Arg Arg Ala  Leu Arg Ser Leu
    1295             1300             1305

Lys Ala  Asn Gln Pro Gln  Val Pro Asn Ser
    1310             1315

<210> SEQ ID NO 4
<211> LENGTH: 1922
<212> TYPE: PRT
<213> ORGANISM: Artificial Sequence
<220> FEATURE:
<223> OTHER INFORMATION: Synthetic polypeptide

<400> SEQUENCE: 4

Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Ala Thr Phe Ile Ala Val Leu Leu Thr Lys Glu
65                  70                  75                  80

Leu Ser Tyr Gln Ile Arg Gly Asp Phe Ser Arg Asn Gly Lys Arg Thr
                85                  90                  95

Val Phe Leu Val Asn Ser Ala Asn Gln Val Ala Gln Gln Val Ser Ala
            100                 105                 110
```

-continued

Val Arg Thr His Ser Asp Leu Lys Val Gly Glu Tyr Ser Asn Leu Glu
            115                 120                 125

Val Asn Ala Ser Trp Thr Lys Glu Arg Trp Asn Gln Glu Phe Thr Lys
130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Glu Asn Cys Pro Ser Cys Pro Arg Ile Leu Gly Leu Thr Ala Ser
            195                 200                 205

Ile Leu Asn Gly Lys Cys Asp Pro Glu Glu Leu Glu Glu Lys Ile Gln
210                 215                 220

Lys Leu Glu Lys Ile Leu Lys Ser Asn Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
            260                 265                 270

Glu Leu Glu Glu Ala Leu Asn Phe Ile Asn Asp Cys Asn Ile Ser Val
            275                 280                 285

His Ser Lys Glu Arg Asp Ser Thr Leu Ile Ser Lys Gln Ile Leu Ser
            290                 295                 300

Asp Cys Arg Ala Val Leu Val Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Phe Leu
            340                 345                 350

Arg Lys Ile His Ala Leu Cys Glu Glu His Phe Ser Pro Ala Ser Leu
            355                 360                 365

Asp Leu Lys Phe Val Thr Pro Lys Val Ile Lys Leu Leu Glu Ile Leu
            370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415

Asp Asp Asp Glu Asp Glu Glu Ile Glu Glu Lys Glu Lys Pro Glu Thr
            420                 425                 430

Asn Phe Pro Ser Pro Phe Thr Asn Ile Leu Cys Gly Ile Ile Phe Val
            435                 440                 445

Glu Arg Arg Tyr Thr Ala Val Val Leu Asn Arg Leu Ile Lys Glu Ala
450                 455                 460

Gly Lys Gln Asp Pro Glu Leu Ala Tyr Ile Ser Ser Asn Phe Ile Thr
465                 470                 475                 480

Gly His Gly Ile Gly Lys Asn Gln Pro Arg Asn Lys Gln Met Glu Ala
                485                 490                 495

Glu Phe Arg Lys Gln Glu Glu Val Leu Arg Lys Phe Arg Ala His Glu
            500                 505                 510

Thr Asn Leu Leu Ile Ala Thr Ser Ile Val Glu Glu Gly Val Asp Ile
            515                 520                 525

Pro Lys Cys Asn Leu Val Val Arg Phe Asp Leu Pro Thr Glu Tyr Arg

```
                530               535               540
Ser Tyr Val Gln Ser Lys Gly Arg Ala Arg Ala Pro Ile Ser Asn Tyr
545               550               555               560

Ile Met Leu Ala Asp Thr Asp Lys Ile Lys Ser Phe Glu Glu Asp Leu
                565               570               575

Lys Thr Tyr Lys Ala Ile Glu Lys Ile Leu Arg Asn Lys Cys Ser Lys
                580               585               590

Ser Val Asp Thr Gly Glu Thr Asp Ile Asp Pro Val Met Asp Asp Asp
                595               600               605

Asp Val Phe Pro Pro Tyr Val Leu Arg Pro Asp Gly Gly Pro Arg
                610               615               620

Val Thr Ile Asn Thr Ala Ile Gly His Ile Asn Arg Tyr Cys Ala Arg
625               630               635               640

Leu Pro Ser Asp Pro Phe Thr His Leu Ala Pro Lys Cys Arg Thr Arg
                645               650               655

Glu Leu Pro Asp Gly Thr Phe Tyr Ser Thr Leu Tyr Leu Pro Ile Asn
                660               665               670

Ser Pro Leu Arg Ala Ser Ile Val Gly Pro Pro Met Ser Cys Val Arg
                675               680               685

Leu Ala Glu Arg Val Val Ala Leu Ile Cys Cys Glu Lys Leu His Lys
690               695               700

Ile Gly Glu Leu Asp Asp His Leu Met Pro Val Gly Lys Glu Thr Val
705               710               715               720

Lys Tyr Glu Glu Glu Leu Asp Leu His Asp Glu Glu Thr Ser Val
                725               730               735

Pro Gly Arg Pro Gly Ser Thr Lys Arg Arg Gln Cys Tyr Pro Lys Ala
                740               745               750

Ile Pro Glu Cys Leu Arg Asp Ser Tyr Pro Arg Pro Asp Gln Pro Cys
                755               760               765

Tyr Leu Tyr Val Ile Gly Met Val Leu Thr Thr Pro Leu Pro Asp Glu
                770               775               780

Leu Asn Phe Arg Arg Arg Lys Leu Tyr Pro Pro Glu Asp Thr Thr Arg
785               790               795               800

Cys Phe Gly Ile Leu Thr Ala Lys Pro Ile Pro Gln Ile Pro His Phe
                805               810               815

Pro Val Tyr Thr Arg Ser Gly Glu Val Thr Ile Ser Ile Glu Leu Lys
                820               825               830

Lys Ser Gly Phe Met Leu Ser Leu Gln Met Leu Glu Leu Ile Thr Arg
                835               840               845

Leu His Gln Tyr Ile Phe Ser His Ile Leu Arg Leu Glu Lys Pro Ala
850               855               860

Leu Glu Phe Lys Pro Thr Asp Ala Asp Ser Ala Tyr Cys Val Leu Pro
865               870               875               880

Leu Asn Val Val Asn Asp Ser Ser Thr Leu Asp Ile Asp Phe Lys Phe
                885               890               895

Met Glu Asp Ile Glu Lys Ser Glu Ala Arg Ile Gly Ile Pro Ser Thr
                900               905               910

Lys Tyr Thr Lys Glu Thr Pro Phe Val Phe Lys Leu Glu Asp Tyr Gln
                915               920               925

Asp Ala Val Ile Ile Pro Arg Tyr Arg Asn Phe Asp Gln Pro His Arg
                930               935               940

Phe Tyr Val Ala Asp Val Tyr Thr Asp Leu Thr Pro Leu Ser Lys Phe
945               950               955               960
```

-continued

```
Pro Ser Pro Glu Tyr Glu Thr Phe Ala Glu Tyr Tyr Lys Thr Lys Tyr
            965                 970                 975
Asn Leu Asp Leu Thr Asn Leu Asn Gln Pro Leu Leu Asp Val Asp His
            980                 985                 990
Thr Ser Ser Arg Leu Asn Leu Leu Thr Pro Arg His Leu Asn Gln Lys
            995                1000                1005
Gly Lys Ala Leu Pro Leu Ser Ser Ala Glu Lys Arg Lys Ala Lys
        1010                1015            1020
Trp Glu Ser Leu Gln Asn Lys Gln Ile Leu Val Pro Glu Leu Cys
        1025                1030            1035
Ala Ile His Pro Ile Pro Ala Ser Leu Trp Arg Lys Ala Val Cys
        1040                1045            1050
Leu Pro Ser Ile Leu Tyr Arg Leu His Cys Leu Leu Thr Ala Glu
        1055                1060            1065
Glu Leu Arg Ala Gln Thr Ala Ser Asp Ala Gly Val Gly Val Arg
        1070                1075            1080
Ser Leu Pro Ala Asp Phe Arg Tyr Pro Asn Leu Asp Phe Gly Trp
        1085                1090            1095
Lys Lys Ser Ile Asp Ser Lys Ser Phe Ile Ser Ile Ser Asn Ser
        1100                1105            1110
Ser Ser Ala Glu Asn Asp Asn Tyr Cys Lys His Ser Thr Ile Val
        1115                1120            1125
Pro Glu Asn Ala Ala His Gln Gly Ala Asn Arg Thr Ser Ser Leu
        1130                1135            1140
Glu Asn His Asp Gln Met Ser Val Asn Cys Arg Thr Leu Leu Ser
        1145                1150            1155
Glu Ser Pro Gly Lys Leu His Val Glu Val Ser Ala Asp Leu Thr
        1160                1165            1170
Ala Ile Asn Gly Leu Ser Tyr Asn Gln Asn Leu Ala Asn Gly Ser
        1175                1180            1185
Tyr Asp Leu Ala Asn Arg Asp Phe Cys Gln Gly Asn Gln Leu Asn
        1190                1195            1200
Tyr Tyr Lys Gln Glu Ile Pro Val Gln Pro Thr Thr Ser Tyr Ser
        1205                1210            1215
Ile Gln Asn Leu Tyr Ser Tyr Glu Asn Gln Pro Gln Pro Ser Asp
        1220                1225            1230
Glu Cys Thr Leu Leu Ser Asn Lys Tyr Leu Asp Gly Asn Ala Asn
        1235                1240            1245
Lys Ser Thr Ser Asp Gly Ser Pro Val Met Ala Val Met Pro Gly
        1250                1255            1260
Thr Thr Asp Thr Ile Gln Val Leu Lys Gly Arg Met Asp Ser Glu
        1265                1270            1275
Gln Ser Pro Ser Ile Gly Tyr Ser Ser Arg Thr Leu Gly Pro Asn
        1280                1285            1290
Pro Gly Leu Ile Leu Gln Ala Leu Thr Leu Ser Asn Ala Ser Asp
        1295                1300            1305
Gly Phe Asn Leu Glu Arg Leu Glu Met Leu Gly Asp Ser Phe Leu
        1310                1315            1320
Lys His Ala Ile Thr Thr Tyr Leu Phe Cys Thr Tyr Pro Asp Ala
        1325                1330            1335
His Glu Gly Arg Leu Ser Tyr Met Arg Ser Lys Lys Val Ser Asn
        1340                1345            1350
Cys Asn Leu Tyr Arg Leu Gly Lys Lys Lys Gly Leu Pro Ser Arg
        1355                1360            1365
```

```
Met Val Val Ser Ile Phe Asp Pro Pro Val Asn Trp Leu Pro Pro
    1370            1375            1380

Gly Tyr Val Val Asn Gln Asp Lys Ser Asn Thr Asp Lys Trp Glu
    1385            1390            1395

Lys Asp Glu Met Thr Lys Asp Cys Met Leu Ala Asn Gly Lys Leu
    1400            1405            1410

Asp Glu Asp Tyr Glu Glu Asp Glu Glu Glu Ser Leu Met
    1415            1420            1425

Trp Arg Ala Pro Lys Glu Glu Ala Asp Tyr Glu Asp Asp Phe Leu
    1430            1435            1440

Glu Tyr Asp Gln Glu His Ile Arg Phe Ile Asp Asn Met Leu Met
    1445            1450            1455

Gly Ser Gly Ala Phe Val Lys Lys Ile Ser Leu Ser Pro Phe Ser
    1460            1465            1470

Thr Thr Asp Ser Ala Tyr Glu Trp Lys Met Pro Lys Lys Ser Ser
    1475            1480            1485

Leu Gly Ser Met Pro Phe Ser Ser Asp Phe Glu Asp Phe Asp Tyr
    1490            1495            1500

Ser Ser Trp Asp Ala Met Cys Tyr Leu Asp Pro Ser Lys Ala Val
    1505            1510            1515

Glu Glu Asp Asp Phe Val Val Gly Phe Trp Asn Pro Ser Glu Glu
    1520            1525            1530

Asn Cys Gly Val Asp Thr Gly Lys Gln Ser Ile Ser Tyr Asp Leu
    1535            1540            1545

His Thr Glu Gln Cys Ile Ala Asp Lys Ser Ile Ala Asp Cys Val
    1550            1555            1560

Glu Ala Leu Leu Gly Cys Tyr Leu Thr Ser Cys Gly Glu Arg Ala
    1565            1570            1575

Ala Gln Leu Phe Leu Cys Ser Leu Gly Leu Lys Val Leu Pro Val
    1580            1585            1590

Ile Lys Arg Thr Asp Arg Glu Lys Ala Leu Cys Pro Thr Arg Glu
    1595            1600            1605

Asn Phe Asn Ser Gln Gln Lys Asn Leu Ser Val Ser Cys Ala Ala
    1610            1615            1620

Ala Ser Val Ala Ser Ser Arg Ser Ser Val Leu Lys Asp Ser Glu
    1625            1630            1635

Tyr Gly Cys Leu Lys Ile Pro Pro Arg Cys Met Phe Asp His Pro
    1640            1645            1650

Asp Ala Asp Lys Thr Leu Asn His Leu Ile Ser Gly Phe Glu Asn
    1655            1660            1665

Phe Glu Lys Lys Ile Asn Tyr Arg Phe Lys Asn Lys Ala Tyr Leu
    1670            1675            1680

Leu Gln Ala Phe Thr His Ala Ser Tyr His Tyr Asn Thr Ile Thr
    1685            1690            1695

Asp Cys Tyr Gln Arg Leu Glu Phe Leu Gly Asp Ala Ile Leu Asp
    1700            1705            1710

Tyr Leu Ile Thr Lys His Leu Tyr Glu Asp Pro Arg Gln His Ser
    1715            1720            1725

Pro Gly Val Leu Thr Asp Leu Arg Ser Ala Leu Val Asn Asn Thr
    1730            1735            1740

Ile Phe Ala Ser Leu Ala Val Lys Tyr Asp Tyr His Lys Tyr Phe
    1745            1750            1755

Lys Ala Val Ser Pro Glu Leu Phe His Val Ile Asp Asp Phe Val
```

-continued

|     |     |     |     | 1760 |     |     |     |     | 1765 |     |     |     |     | 1770 |

Gln Phe Gln Leu Glu Lys Asn Glu Met Gln Gly Met Asp Ser Glu
    1775                1780                1785

Leu Arg Arg Ser Glu Glu Asp Glu Glu Lys Glu Asp Ile Glu
    1790                1795                1800

Val Pro Lys Ala Met Gly Asp Ile Phe Glu Ser Leu Ala Gly Ala
    1805                1810                1815

Ile Tyr Met Asp Ser Gly Met Ser Leu Glu Thr Val Trp Gln Val
    1820                1825                1830

Tyr Tyr Pro Met Met Arg Pro Leu Ile Glu Lys Phe Ser Ala Asn
    1835                1840                1845

Val Pro Arg Ser Pro Val Arg Glu Leu Leu Glu Met Glu Pro Glu
    1850                1855                1860

Thr Ala Lys Phe Ser Pro Ala Glu Arg Thr Tyr Asp Gly Lys Val
    1865                1870                1875

Arg Val Thr Val Glu Val Val Gly Lys Gly Lys Phe Lys Gly Val
    1880                1885                1890

Gly Arg Ser Tyr Arg Ile Ala Lys Ser Ala Ala Ala Arg Arg Ala
    1895                1900                1905

Leu Arg Ser Leu Lys Ala Asn Gln Pro Gln Val Pro Asn Ser
    1910                1915                1920

<210> SEQ ID NO 5
<211> LENGTH: 37
<212> TYPE: RNA
<213> ORGANISM: Artificial Sequence
<220> FEATURE:
<223> OTHER INFORMATION: Synthetic polynucleotide

<400> SEQUENCE: 5
ugagguagua gguuguauag uuugaaaguu cacgauu                                37

<210> SEQ ID NO 6
<211> LENGTH: 37
<212> TYPE: RNA
<213> ORGANISM: Artificial Sequence
<220> FEATURE:
<223> OTHER INFORMATION: Synthetic polynucleotide

<400> SEQUENCE: 6
ucgugaacuu ucaaacuaua caaccuacua ccucauu                                37

<210> SEQ ID NO 7
<211> LENGTH: 73
<212> TYPE: RNA
<213> ORGANISM: Artificial Sequence
<220> FEATURE:
<223> OTHER INFORMATION: Synthetic polynucleotide

<400> SEQUENCE: 7
ugagguagua gguuguauag uuuuaggguc acacccacca cugggagaua acuauacaau      60
cuacugucuu acc                                                          73

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 8

Cys Leu Asn Thr Gly Ser Gly Lys Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Cys Leu Asn Asp Gly Ser Gly Lys Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 10

Cys Leu Asn Thr Pro Ser Gly Lys Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

Cys Leu Ser Thr Gly Ser Gly Lys Thr
1               5

<210> SEQ ID NO 12
<211> LENGTH: 46
<212> TYPE: DNA
<213> ORGANISM: Artificial Sequence
<220> FEATURE:
<223> OTHER INFORMATION: Synthetic primer

<400> SEQUENCE: 12
gggggcgcca tgaaaagccc tgctttgcaa ccccctcagca tggcag         46

<210> SEQ ID NO 13
<211> LENGTH: 39
<212> TYPE: DNA
<213> ORGANISM: Artificial Sequence
<220> FEATURE:
<223> OTHER INFORMATION: Synthetic primer

<400> SEQUENCE: 13 ccccctcgagt cagctattgg gaacctgagg ttgattagc          39

<210> SEQ ID NO 14
<211> LENGTH: 45
<212> TYPE: DNA
<213> ORGANISM: Artificial Sequence
<220> FEATURE:
<223> OTHER INFORMATION: Synthetic primer

<400> SEQUENCE: 14
gggggcgcca tggatgatga tgacgttttc ccaccatatg tgttg           45

<210> SEQ ID NO 15

-continued

<210> SEQ ID NO 15
<211> LENGTH: 45
<212> TYPE: DNA
<213> ORGANISM: Artificial Sequence
<220> FEATURE:
<223> OTHER INFORMATION: Synthetic primer

<400> SEQUENCE: 15
cgagtcacaa tcaacacgga ccatttgatg ccagttggga aagag    45

<210> SEQ ID NO 16
<211> LENGTH: 45
<212> TYPE: DNA
<213> ORGANISM: Artificial Sequence
<220> FEATURE:
<223> OTHER INFORMATION: Synthetic primer

<400> SEQUENCE: 16
cccaactggc atcaaatggt ccgtgttgat tgtgactcgt ggacc    45

<210> SEQ ID NO 17
<211> LENGTH: 44
<212> TYPE: DNA
<213> ORGANISM: Artificial Sequence
<220> FEATURE:
<223> OTHER INFORMATION: Synthetic primer

<400> SEQUENCE: 17
gaaaagtttt ctgcaaataa tcaacctcag gttcccaata gctg    44

<210> SEQ ID NO 18
<211> LENGTH: 46
<212> TYPE: DNA
<213> ORGANISM: Artificial Sequence
<220> FEATURE:
<223> OTHER INFORMATION: Synthetic primer

<400> SEQUENCE: 18
gggaacctga ggttgattat ttgcagaaaa cttttctatt agtggc    46

<210> SEQ ID NO 19
<211> LENGTH: 34
<212> TYPE: DNA
<213> ORGANISM: Artificial Sequence
<220> FEATURE:
<223> OTHER INFORMATION: Synthetic primer

<400> SEQUENCE: 19
aacactggct cagggcgac atttattgca gtac    34

<210> SEQ ID NO 20
<211> LENGTH: 34
<212> TYPE: DNA
<213> ORGANISM: Artificial Sequence
<220> FEATURE:
<223> OTHER INFORMATION: Synthetic primer

<400> SEQUENCE: 20
gtactgcaat aaatgtcgcc cctgagccag tgtt    34

<210> SEQ ID NO 21
<211> LENGTH: 1930
<212> TYPE: PRT
<213> ORGANISM: Pan troglodytes

<400> SEQUENCE: 21

Met Lys Asn Pro Ala Leu Gln Pro Leu Ser Met Ala Gly Leu Gln Leu
1               5                   10                  15

```
Met Thr Pro Ala Ser Ser Pro Met Gly Pro Phe Phe Gly Leu Pro Trp
                20                  25                  30
Gln Gln Glu Ala Ile His Asp Asn Ile Tyr Thr Pro Arg Lys Tyr Gln
                35                  40                  45
Val Glu Leu Leu Glu Ala Ala Leu Asp His Asn Thr Ile Val Cys Leu
50                  55                  60
Asn Thr Gly Ser Gly Lys Thr Phe Ile Ala Val Leu Leu Thr Lys Glu
65                  70                  75                  80
Leu Ser Tyr Gln Ile Arg Gly Asp Phe Ser Arg Asn Gly Lys Arg Thr
                85                  90                  95
Val Phe Leu Val Asn Ser Ala Asn Gln Val Ala Gln Gln Val Ser Ala
                100                 105                 110
Val Arg Thr His Ser Asp Leu Lys Val Gly Glu Tyr Ser Asn Leu Glu
                115                 120                 125
Val Asn Ala Ser Trp Thr Lys Glu Arg Trp Asn Gln Glu Phe Thr Lys
                130                 135                 140
His Gln Val Leu Ile Met Thr Cys Tyr Val Ala Leu Asn Val Leu Lys
145                 150                 155                 160
Asn Gly Tyr Leu Ser Leu Ser Asp Ile Asn Leu Leu Val Phe Asp Glu
                165                 170                 175
Cys His Leu Ala Ile Leu Asp His Pro Tyr Arg Glu Ile Met Lys Leu
                180                 185                 190
Cys Glu Asn Cys Pro Ser Cys Pro Arg Ile Leu Gly Leu Thr Ala Ser
                195                 200                 205
Ile Leu Asn Gly Lys Cys Asp Pro Glu Glu Leu Glu Glu Lys Ile Gln
                210                 215                 220
Lys Leu Glu Lys Ile Leu Lys Ser Asn Ala Glu Thr Ala Thr Asp Leu
225                 230                 235                 240
Val Val Leu Asp Arg Tyr Thr Ser Gln Pro Cys Glu Ile Val Val Asp
                245                 250                 255
Cys Gly Pro Phe Thr Asp Arg Ser Gly Leu Tyr Glu Arg Leu Leu Met
                260                 265                 270
Glu Leu Glu Glu Ala Leu Asn Phe Ile Asn Asp Cys Asn Ile Ser Val
                275                 280                 285
His Ser Lys Glu Arg Asp Ser Thr Leu Ile Ser Lys Gln Ile Leu Ser
290                 295                 300
Asp Cys Arg Ala Val Leu Val Val Leu Gly Pro Trp Cys Ala Asp Lys
305                 310                 315                 320
Val Ala Gly Met Met Val Arg Glu Leu Gln Lys Tyr Ile Lys His Glu
                325                 330                 335
Gln Glu Glu Leu His Arg Lys Phe Leu Leu Phe Thr Asp Thr Phe Leu
                340                 345                 350
Arg Lys Ile His Ala Leu Cys Glu Glu His Phe Ser Pro Ala Ser Leu
                355                 360                 365
Asp Leu Lys Phe Val Thr Pro Lys Val Ile Lys Leu Leu Glu Ile Leu
                370                 375                 380
Arg Lys Tyr Lys Pro Tyr Glu Arg Gln Gln Phe Glu Ser Val Glu Trp
385                 390                 395                 400
Tyr Asn Asn Arg Asn Gln Asp Asn Tyr Val Ser Trp Ser Asp Ser Glu
                405                 410                 415
Asp Asp Asp Glu Asp Glu Glu Ile Glu Glu Lys Glu Lys Pro Glu Thr
                420                 425                 430
Asn Phe Pro Ser Pro Phe Thr Asn Ile Leu Cys Gly Ile Ile Phe Val
```

```
                435                 440                 445
Glu Arg Arg Tyr Thr Ala Val Val Leu Asn Arg Leu Ile Lys Glu Ala
450                 455                 460
Gly Lys Gln Asp Pro Glu Leu Ala Tyr Ile Ser Ser Asn Phe Ile Thr
465                 470                 475                 480
Gly His Gly Ile Gly Lys Asn Gln Pro Arg Asn Lys Gln Met Glu Ala
                485                 490                 495
Glu Phe Arg Lys Gln Glu Glu Val Leu Arg Lys Phe Arg Ala His Glu
                500                 505                 510
Thr Asn Leu Leu Ile Ala Thr Ser Ile Val Glu Glu Gly Val Asp Ile
            515                 520                 525
Pro Lys Cys Asn Leu Val Val Arg Phe Asp Leu Pro Thr Glu Tyr Arg
530                 535                 540
Ser Tyr Val Gln Ser Lys Gly Arg Ala Arg Ala Pro Ile Ser Asn Tyr
545                 550                 555                 560
Ile Met Leu Ala Asp Thr Asp Lys Ile Lys Ser Phe Glu Glu Asp Leu
                565                 570                 575
Lys Thr Tyr Lys Ala Ile Glu Lys Ile Leu Arg Asn Lys Cys Ser Lys
            580                 585                 590
Ser Val Asp Thr Gly Glu Ile Asp Ile Asp Pro Val Met Asp Asp Asp
        595                 600                 605
Asp Val Phe Pro Pro Tyr Val Leu Arg Pro Asp Gly Gly Pro Arg
        610                 615                 620
Val Thr Ile Asn Thr Ala Ile Gly His Ile Asn Arg Tyr Cys Ala Arg
625                 630                 635                 640
Leu Pro Ser Asp Pro Phe Thr His Leu Ala Pro Lys Cys Arg Thr Arg
                645                 650                 655
Glu Leu Pro Asp Gly Thr Phe Tyr Ser Thr Leu Tyr Leu Pro Ile Asn
                660                 665                 670
Ser Pro Leu Arg Ala Ser Ile Val Gly Pro Pro Met Ser Cys Val Arg
            675                 680                 685
Leu Ala Glu Arg Val Val Ala Leu Ile Cys Cys Glu Lys Leu His Lys
        690                 695                 700
Ile Gly Glu Leu Asp Asp His Leu Met Pro Val Gly Lys Glu Thr Val
705                 710                 715                 720
Lys Tyr Glu Glu Glu Leu Asp Leu His Asp Glu Glu Thr Ser Val
                725                 730                 735
Pro Gly Arg Pro Gly Ser Thr Lys Arg Arg Gln Cys Tyr Pro Lys Ala
            740                 745                 750
Ile Pro Glu Cys Leu Arg Asp Ser Tyr Pro Arg Pro Asp Gln Pro Cys
        755                 760                 765
Tyr Leu Tyr Val Ile Gly Met Val Leu Thr Thr Pro Leu Pro Asp Glu
        770                 775                 780
Leu Asn Phe Arg Arg Arg Lys Leu Tyr Pro Pro Glu Asp Thr Thr Arg
785                 790                 795                 800
Cys Phe Gly Ile Leu Thr Ala Lys Pro Ile Pro Gln Ile Pro His Phe
                805                 810                 815
Pro Val Tyr Thr Arg Ser Gly Glu Val Thr Ile Ser Ile Glu Leu Lys
            820                 825                 830
Lys Ser Gly Phe Met Leu Ser Leu Gln Met Leu Glu Leu Ile Thr Arg
        835                 840                 845
Leu His Gln Tyr Ile Phe Ser His Ile Leu Arg Leu Glu Lys Pro Ala
    850                 855                 860
```

-continued

Leu Glu Phe Lys Pro Thr Asp Ala Asp Ser Ala Tyr Cys Val Leu Pro
865                 870                 875                 880

Leu Asn Val Val Asn Asp Ser Thr Leu Asp Ile Asp Phe Lys Phe
            885                 890                 895

Met Glu Asp Ile Glu Lys Ser Glu Ala Arg Ile Gly Ile Pro Ser Thr
                900                 905                 910

Lys Tyr Thr Lys Glu Thr Pro Phe Val Phe Lys Leu Glu Asp Tyr Gln
            915                 920                 925

Asp Ala Val Ile Ile Pro Arg Tyr Arg Asn Phe Asp Gln Pro His Arg
930                 935                 940

Phe Tyr Val Ala Asp Val Tyr Thr Asp Leu Thr Pro Leu Ser Lys Phe
945                 950                 955                 960

Pro Ser Pro Glu Tyr Glu Thr Phe Ala Glu Tyr Tyr Lys Thr Lys Tyr
            965                 970                 975

Asn Leu Asp Leu Thr Asn Leu Asn Gln Pro Leu Leu Asp Val Asp His
                980                 985                 990

Thr Ser Ser Arg Leu Asn Leu Leu Thr Pro Arg His Leu Asn Gln Lys
            995                 1000                1005

Gly Lys Ala Leu Pro Leu Ser Ser Ala Glu Lys Arg Lys Ala Lys
    1010                1015                1020

Trp Glu Ser Leu Gln Asn Lys Gln Ile Leu Val Pro Glu Leu Cys
    1025                1030                1035

Ala Ile His Pro Ile Pro Ala Ser Leu Trp Arg Lys Ala Val Cys
    1040                1045                1050

Leu Pro Ser Ile Leu Tyr Arg Leu His Cys Leu Leu Thr Ala Glu
    1055                1060                1065

Glu Leu Arg Ala Gln Thr Ala Ser Asp Ala Gly Val Gly Val Arg
    1070                1075                1080

Ser Leu Pro Ala Asp Phe Arg Tyr Pro Asn Leu Asp Phe Gly Trp
    1085                1090                1095

Lys Lys Ser Ile Asp Ser Lys Ser Phe Ile Ser Ile Ser Asn Ser
    1100                1105                1110

Ser Ser Ala Glu Asn Asp Asn Tyr Cys Lys His Ser Thr Ile Val
    1115                1120                1125

Pro Glu Asn Ala Ala His Gln Gly Ala Asn Arg Thr Ser Ser Leu
    1130                1135                1140

Glu Asn His Asp Gln Met Ser Val Asn Cys Arg Thr Leu Leu Ser
    1145                1150                1155

Glu Ser Pro Gly Lys Leu His Val Glu Val Ser Ala Asp Leu Thr
    1160                1165                1170

Ala Ile Asn Gly Leu Ser Tyr Asn Gln Asn Leu Ala Asn Gly Ser
    1175                1180                1185

Tyr Asp Leu Ala Asn Arg Asp Phe Cys Gln Gly Asn Gln Leu Asn
    1190                1195                1200

Tyr Tyr Lys Gln Glu Ile Pro Val Gln Pro Thr Thr Ser Tyr Ser
    1205                1210                1215

Ile Gln Asn Leu Tyr Ser Tyr Glu Asn Gln Pro Gln Pro Ser Asp
    1220                1225                1230

Glu Cys Thr Leu Leu Ser Asn Lys Tyr Leu Asp Gly Asn Ala Asn
    1235                1240                1245

Lys Ser Thr Ser Asp Gly Ser Pro Val Met Ala Val Met Pro Gly
    1250                1255                1260

Thr Thr Asp Thr Ile Gln Val Leu Lys Gly Arg Met Asp Ser Glu
    1265                1270                1275

```
Gln Ser Pro Ser Ile Gly Tyr Ser Ser Arg Thr Leu Gly Pro Asn
    1280            1285                1290

Pro Gly Leu Ile Leu Gln Ala Leu Thr Leu Ser Asn Ala Ser Asp
    1295            1300                1305

Gly Phe Asn Leu Glu Arg Leu Glu Met Leu Gly Asp Ser Phe Leu
    1310            1315                1320

Lys His Ala Ile Thr Thr Tyr Leu Phe Cys Thr Tyr Pro Asp Ala
    1325            1330                1335

His Glu Gly Arg Leu Ser Tyr Met Arg Ser Lys Lys Val Ser Asn
    1340            1345                1350

Cys Asn Leu Tyr Arg Leu Gly Lys Lys Gly Leu Pro Ser Arg
    1355            1360                1365

Met Val Val Ser Ile Phe Asp Pro Pro Val Asn Trp Leu Pro Pro
    1370            1375                1380

Gly Tyr Val Val Asn Gln Asp Lys Ser Asn Thr Asp Lys Trp Glu
    1385            1390                1395

Lys Asp Glu Met Thr Lys Asp Cys Met Leu Ala Asn Gly Lys Leu
    1400            1405                1410

Asp Glu Asp Tyr Glu Glu Glu Asp Glu Glu Glu Ser Leu Met
    1415            1420                1425

Trp Arg Ala Pro Lys Glu Glu Ala Asp Tyr Glu Asp Asp Phe Leu
    1430            1435                1440

Glu Tyr Asp Gln Glu His Ile Arg Phe Ile Asp Asn Met Leu Met
    1445            1450                1455

Gly Ser Gly Ala Phe Val Lys Lys Ile Ser Leu Ser Pro Phe Ser
    1460            1465                1470

Thr Thr Asp Ser Ala Tyr Glu Trp Lys Met Pro Lys Lys Ser Ser
    1475            1480                1485

Leu Gly Ser Met Pro Phe Ser Ser Asp Phe Glu Asp Phe Asp Tyr
    1490            1495                1500

Ser Ser Trp Asp Ala Met Cys Tyr Leu Asp Pro Ser Lys Ala Val
    1505            1510                1515

Glu Glu Asp Asp Phe Val Val Gly Phe Trp Asn Pro Ser Glu Glu
    1520            1525                1530

Asn Cys Gly Val Asp Thr Gly Lys Gln Ser Ile Ser Tyr Asp Leu
    1535            1540                1545

His Thr Glu Gln Cys Ile Ala Asp Lys Ser Ile Ala Asp Cys Val
    1550            1555                1560

Glu Ala Leu Leu Gly Cys Tyr Leu Thr Ser Cys Gly Glu Arg Ala
    1565            1570                1575

Ala Gln Leu Phe Leu Cys Ser Leu Gly Leu Lys Val Leu Pro Val
    1580            1585                1590

Ile Lys Arg Thr Asp Arg Glu Lys Ala Leu Cys Pro Thr Arg Glu
    1595            1600                1605

Asn Phe Asn Ser Gln Gln Lys Asn Leu Ser Val Ser Cys Ala Ala
    1610            1615                1620

Ala Ser Val Ala Ser Ser Arg Ser Ser Val Leu Lys Asp Ser Glu
    1625            1630                1635

Tyr Gly Cys Leu Lys Ile Pro Pro Arg Cys Met Phe Asp His Pro
    1640            1645                1650

Asp Ala Asp Lys Thr Leu Asn His Leu Ile Ser Gly Phe Glu Asn
    1655            1660                1665

Phe Glu Lys Lys Ile Asn Tyr Arg Phe Lys Asn Lys Ala Tyr Leu
```

-continued

```
                         1670               1675               1680

Leu Gln Ala Phe Thr His Ala Ser Tyr His Tyr Asn Thr Ile Thr
                1685               1690               1695

Asp Cys Tyr Gln Arg Leu Glu Phe Leu Gly Asp Ala Ile Leu Asp
                1700               1705               1710

Tyr Leu Ile Thr Lys His Leu Tyr Glu Asp Pro Arg Gln His Ser
                1715               1720               1725

Pro Gly Val Leu Thr Asp Leu Arg Ser Ala Leu Val Asn Asn Thr
                1730               1735               1740

Ile Phe Ala Ser Leu Ala Val Lys Tyr Asp Tyr His Lys Tyr Phe
                1745               1750               1755

Lys Ala Val Ser Pro Glu Leu Phe His Val Ile Asp Asp Phe Val
                1760               1765               1770

Gln Phe Gln Leu Glu Lys Asn Glu Met Gln Gly Met Asp Ser Glu
                1775               1780               1785

Leu Arg Arg Ser Glu Glu Asp Glu Glu Lys Glu Glu Asp Ile Glu
                1790               1795               1800

Val Pro Lys Ala Met Gly Asp Ile Phe Glu Ser Leu Ala Gly Ala
                1805               1810               1815

Ile Tyr Met Asp Ser Gly Met Ser Leu Glu Thr Val Trp Gln Val
                1820               1825               1830

Tyr Tyr Pro Met Met Arg Pro Leu Ile Glu Lys Phe Ser Ala Asn
                1835               1840               1845

Val Pro Arg Ser Pro Val Arg Glu Leu Leu Glu Met Glu Pro Glu
                1850               1855               1860

Thr Ala Lys Phe Ser Pro Ala Glu Arg Thr Tyr Asp Gly Lys Val
                1865               1870               1875

Arg Val Thr Val Glu Val Val Gly Lys Gly Lys Phe Lys Gly Val
                1880               1885               1890

Gly Arg Ser Tyr Arg Ile Ala Lys Ser Ala Ala Arg Arg Ala
                1895               1900               1905

Leu Arg Ser Leu Lys Ala Asn Gln Pro Gln Leu Trp Val Ser Leu
                1910               1915               1920

Ala Leu Pro Ser Thr Tyr Gln
                1925               1930

<210> SEQ ID NO 22
<211> LENGTH: 1923
<212> TYPE: PRT
<213> ORGANISM: Canis familiaris

<400> SEQUENCE: 22

Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
                20                  25                  30

Gln Gln Glu Ala Ile His Asp Asn Ile Tyr Thr Pro Arg Lys Tyr Gln
            35                  40                  45

Val Glu Leu Leu Glu Ala Ala Leu Asp His Asn Thr Ile Val Cys Leu
        50                  55                  60

Asn Thr Gly Ser Gly Lys Thr Phe Ile Ala Val Leu Leu Thr Lys Glu
65                  70                  75                  80

Leu Ser Tyr Gln Ile Arg Gly Asp Phe Asn Arg Asn Gly Lys Arg Thr
                85                  90                  95

Val Phe Leu Val Asn Ser Ala Asn Gln Val Ala Gln Gln Val Ser Ala
```

```
                100             105             110
Val Arg Thr His Ser Asp Leu Lys Val Gly Glu Tyr Ser Asn Leu Glu
            115                 120                 125
Val Asn Ala Ser Trp Thr Lys Glu Lys Trp Asn Gln Glu Phe Thr Lys
            130                 135                 140
His Gln Val Leu Val Met Thr Cys Tyr Val Ala Leu Asn Val Leu Lys
145                 150                 155                 160
Asn Gly Tyr Leu Ser Leu Ser Asp Ile Asn Leu Leu Val Phe Asp Glu
                165                 170                 175
Cys His Leu Ala Ile Leu Asp His Pro Tyr Arg Glu Ile Met Lys Leu
                180                 185                 190
Cys Glu Asn Cys Pro Ser Cys Pro Arg Ile Leu Gly Leu Thr Ala Ser
                195                 200                 205
Ile Leu Asn Gly Lys Cys Asp Pro Glu Glu Leu Glu Glu Lys Ile Gln
            210                 215                 220
Lys Leu Glu Lys Ile Leu Lys Ser Asn Ala Glu Thr Ala Thr Asp Leu
225                 230                 235                 240
Val Val Leu Asp Arg Tyr Thr Ser Gln Pro Cys Glu Ile Val Val Asp
                245                 250                 255
Cys Gly Pro Phe Thr Asp Arg Ser Gly Leu Tyr Gly Arg Leu Leu Val
                260                 265                 270
Glu Leu Glu Glu Ala Leu Asn Phe Ile Asn Asp Cys Asn Ile Ser Val
            275                 280                 285
His Ser Lys Glu Arg Asp Ser Thr Leu Ile Ser Lys Gln Ile Leu Ser
            290                 295                 300
Asp Cys Arg Ala Val Leu Val Val Leu Gly Pro Trp Cys Ala Asp Lys
305                 310                 315                 320
Val Ala Gly Met Met Val Arg Glu Leu Gln Lys Tyr Ile Lys His Glu
                325                 330                 335
Gln Glu Glu Leu His Arg Lys Phe Leu Leu Phe Thr Asp Thr Phe Leu
                340                 345                 350
Arg Lys Ile His Ala Leu Cys Glu Glu His Phe Ser Pro Ala Ser Leu
            355                 360                 365
Asp Leu Lys Phe Val Thr Pro Lys Val Ile Lys Leu Leu Glu Ile Leu
            370                 375                 380
Arg Lys Tyr Lys Pro Tyr Glu Arg Gln Gln Phe Glu Ser Val Glu Trp
385                 390                 395                 400
Tyr Asn Asn Arg Asn Gln Asp Asn Tyr Val Ser Trp Ser Asp Ser Glu
                405                 410                 415
Asp Asp Asp Glu Asp Glu Glu Ile Glu Glu Lys Glu Lys Pro Glu Thr
                420                 425                 430
Asn Phe Pro Ser Pro Phe Thr Asn Ile Leu Cys Gly Ile Ile Phe Val
            435                 440                 445
Glu Arg Arg Tyr Thr Ala Val Val Leu Asn Arg Leu Ile Lys Glu Ala
            450                 455                 460
Gly Lys Gln Asp Pro Glu Leu Ala Tyr Ile Ser Ser Asn Phe Ile Thr
465                 470                 475                 480
Gly His Gly Ile Gly Lys Asn Gln Pro Arg Asn Lys Gln Met Glu Ala
                485                 490                 495
Glu Phe Arg Lys Gln Glu Val Leu Arg Lys Phe Arg Ala His Glu
                500                 505                 510
Thr Asn Leu Leu Ile Ala Thr Ser Ile Val Glu Glu Gly Val Asp Ile
            515                 520                 525
```

```
Pro Lys Cys Asn Leu Val Val Arg Phe Asp Leu Pro Thr Glu Tyr Arg
    530                 535                 540

Ser Tyr Val Gln Ser Lys Gly Arg Ala Arg Ala Pro Ile Ser Asn Tyr
545                 550                 555                 560

Ile Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
            580                 585                 590

Ser Val Asp Thr Gly Glu Thr Asp Ile Glu Pro Val Asp Asp Asp
        595                 600                 605

Asp Val Phe Pro Pro Tyr Val Leu Arg Pro Asp Gly Gly Pro Arg
    610                 615                 620

Val Thr Ile Asn Thr Ala Ile Gly His Ile Asn Arg Tyr Cys Ala Arg
625                 630                 635                 640

Leu Pro Ser Asp Pro Phe Thr His Leu Ala Pro Lys Cys Arg Thr Arg
                645                 650                 655

Glu Leu Pro Asp Gly Thr Phe Tyr Ser Thr Leu Tyr Leu Pro Ile Asn
            660                 665                 670

Ser Pro Leu Arg Ala Ser Ile Val Gly Pro Pro Met Ser Cys Val Arg
        675                 680                 685

Leu Ala Glu Arg Val Val Ala Leu Ile Cys Cys Glu Lys Leu His Lys
    690                 695                 700

Ile Gly Glu Leu Asp Asp His Leu Met Pro Val Gly Lys Glu Thr Val
705                 710                 715                 720

Lys Tyr Glu Glu Glu Leu Asp Leu His Asp Glu Glu Thr Ser Val
                725                 730                 735

Pro Gly Arg Pro Gly Ser Thr Lys Arg Arg Gln Cys Tyr Pro Lys Ala
            740                 745                 750

Ile Pro Glu Cys Leu Arg Asp Ser Tyr Pro Lys Pro Asp Gln Pro Cys
        755                 760                 765

Tyr Leu Tyr Val Ile Gly Met Val Leu Thr Thr Pro Leu Pro Asp Glu
    770                 775                 780

Leu Asn Phe Arg Arg Lys Leu Tyr Pro Pro Glu Asp Thr Thr Arg
785                 790                 795                 800

Cys Phe Gly Ile Leu Thr Ala Lys Pro Ile Pro Gln Ile Pro His Phe
                805                 810                 815

Pro Val Tyr Thr Arg Ser Gly Glu Val Thr Ile Ser Ile Glu Leu Lys
            820                 825                 830

Lys Ser Gly Phe Thr Leu Ser Leu Gln Met Leu Glu Leu Ile Thr Arg
        835                 840                 845

Leu His Gln Tyr Ile Phe Ser His Ile Leu Arg Leu Glu Lys Pro Ala
    850                 855                 860

Leu Glu Phe Lys Pro Thr Asp Ala Asp Ser Ala Tyr Cys Val Leu Pro
865                 870                 875                 880

Leu Asn Val Val Asn Asp Ser Ser Thr Leu Asp Ile Asp Phe Lys Phe
                885                 890                 895

Met Glu Asp Ile Glu Lys Ser Glu Ala Arg Ile Gly Ile Pro Ser Thr
            900                 905                 910

Lys Tyr Ser Lys Glu Thr Pro Phe Val Phe Lys Leu Glu Asp Tyr Gln
        915                 920                 925

Asp Ala Val Ile Ile Pro Arg Tyr Arg Asn Phe Asp Gln Pro His Arg
    930                 935                 940

Phe Tyr Val Ala Asp Val Tyr Thr Asp Leu Thr Pro Leu Ser Lys Phe
945                 950                 955                 960
```

-continued

```
Pro Ser Pro Glu Tyr Glu Thr Phe Ala Glu Tyr Tyr Lys Thr Lys Tyr
            965                 970                 975

Asn Leu Asp Leu Thr Asn Leu Asn Gln Pro Leu Leu Asp Val Asp His
            980                 985                 990

Thr Ser Ser Arg Leu Asn Leu Leu Thr Pro Arg His Leu Asn Gln Lys
            995                 1000                1005

Gly Lys Ala Leu Pro Leu Ser Ser Ala Glu Lys Arg Lys Ala Lys
    1010                1015                1020

Trp Glu Ser Leu Gln Asn Lys Gln Ile Leu Val Pro Glu Leu Cys
    1025                1030                1035

Ala Ile His Pro Ile Pro Ala Ser Leu Trp Arg Lys Ala Val Cys
    1040                1045                1050

Leu Pro Ser Ile Leu Tyr Arg Leu His Cys Leu Leu Thr Ala Glu
    1055                1060                1065

Glu Leu Arg Ala Gln Thr Ala Ser Asp Ala Gly Val Gly Val Arg
    1070                1075                1080

Ser Leu Pro Val Asp Phe Arg Tyr Pro Asn Leu Asp Phe Gly Trp
    1085                1090                1095

Lys Lys Ser Ile Asp Ser Lys Ser Phe Ile Ser Val Ala Asn Ser
    1100                1105                1110

Ser Ser Ala Glu Asn Glu Asn Tyr Cys Lys His Ser Thr Ile Val
    1115                1120                1125

Val Pro Glu Asn Ala Ala Arg Gln Gly Ala Asn Arg Thr Ser Ser
    1130                1135                1140

Leu Glu Asn His Asp Gln Met Ser Val Asn Cys Arg Thr Leu Phe
    1145                1150                1155

Ser Glu Ser Pro Gly Lys Leu Gln Ile Glu Val Val Thr Asp Leu
    1160                1165                1170

Thr Ala Ile Asn Gly Leu Ser Tyr Asn Lys Asn Leu Ala Asn Gly
    1175                1180                1185

Ser Tyr Asp Leu Ala Asn Arg Asp Phe Cys Gln Gly Asn Gln Leu
    1190                1195                1200

Asn Tyr Tyr Lys Gln Glu Ile Pro Val Gln Pro Thr Thr Ser Tyr
    1205                1210                1215

Pro Ile Gln Asn Leu Tyr Asn Tyr Glu Asn Gln Pro Lys Pro Ser
    1220                1225                1230

Asp Glu Cys Thr Leu Leu Ser Asn Lys Tyr Leu Asp Gly Asn Ala
    1235                1240                1245

Asn Lys Ser Thr Ser Asp Gly Ser Pro Thr Thr Ala Ala Met Pro
    1250                1255                1260

Gly Thr Thr Glu Ala Val Arg Ala Leu Lys Asp Lys Met Gly Ser
    1265                1270                1275

Glu Gln Ser Pro Cys Pro Gly Tyr Ser Ser Arg Thr Leu Gly Pro
    1280                1285                1290

Asn Pro Gly Leu Ile Leu Gln Ala Leu Thr Leu Ser Asn Ala Ser
    1295                1300                1305

Asp Gly Phe Asn Leu Glu Arg Leu Glu Met Leu Gly Asp Ser Phe
    1310                1315                1320

Leu Lys His Ala Ile Thr Thr Tyr Leu Phe Cys Thr Tyr Pro Asp
    1325                1330                1335

Ala His Glu Gly Arg Leu Ser Tyr Met Arg Ser Lys Lys Val Ser
    1340                1345                1350

Asn Cys Asn Leu Tyr Arg Leu Gly Lys Lys Lys Gly Leu Pro Ser
```

|  |  |  |  |  |  |  |  |  |  |
|---|---|---|---|---|---|---|---|---|---|
|  |  | 1355 |  |  | 1360 |  |  | 1365 |  |

Arg Met Val Val Ser Ile Phe Asp Pro Pro Val Asn Trp Leu Pro
1370                     1375                    1380

Pro Gly Tyr Val Val Asn Gln Asp Lys Ser Asn Ala Asp Lys Trp
1385                     1390                    1395

Glu Lys Asp Glu Met Thr Lys Asp Cys Met Leu Ala Asn Gly Lys
1400                     1405                    1410

Leu Asp Glu Asp Phe Glu Glu Asp Glu Glu Glu Glu Asp Leu
1415                     1420                    1425

Met Trp Arg Ala Pro Lys Glu Asp Ala Asp Tyr Glu Asp Asp Phe
1430                     1435                    1440

Leu Glu Tyr Asp Gln Glu His Ile Lys Phe Ile Asp Asn Met Leu
1445                     1450                    1455

Met Gly Ser Gly Ala Phe Val Lys Lys Ile Ser Leu Ser Pro Phe
1460                     1465                    1470

Ser Thr Thr Asp Ser Ala Tyr Glu Trp Lys Met Pro Lys Lys Ser
1475                     1480                    1485

Ser Leu Gly Ser Met Pro Phe Ser Ser Asp Phe Glu Asp Phe Asp
1490                     1495                    1500

Tyr Ser Ser Trp Asp Ala Met Cys Tyr Leu Asp Pro Ser Lys Ala
1505                     1510                    1515

Val Glu Glu Asp Asp Phe Val Val Gly Phe Trp Asn Pro Ser Glu
1520                     1525                    1530

Glu Asn Cys Gly Val Asp Thr Gly Lys Gln Ser Ile Ser Tyr Asp
1535                     1540                    1545

Leu His Thr Glu Gln Cys Ile Ala Asp Lys Ser Ile Ala Asp Cys
1550                     1555                    1560

Val Glu Ala Leu Leu Gly Cys Tyr Leu Thr Ser Cys Gly Glu Arg
1565                     1570                    1575

Ala Ala Gln Leu Phe Leu Cys Ser Leu Gly Leu Lys Val Leu Pro
1580                     1585                    1590

Val Met Lys Arg Thr Asp Arg Glu Lys Thr Met Cys Pro Pro Arg
1595                     1600                    1605

Glu Asn Phe Ser Ser Gln Gln Lys Asn Leu Ser Gly Gly Arg Ala
1610                     1615                    1620

Ala Ala Ser Val Ala Ser Leu Arg Pro Ser Val Leu Lys Asp Leu
1625                     1630                    1635

Glu Tyr Gly Cys Leu Lys Ile Pro Pro Arg Cys Met Phe Asp His
1640                     1645                    1650

Pro Asp Ala Asp Lys Thr Leu Asn His Leu Ile Ser Gly Phe Glu
1655                     1660                    1665

Asn Phe Glu Lys Lys Ile Asn Tyr Arg Phe Lys Asn Lys Ala Tyr
1670                     1675                    1680

Leu Leu Gln Ala Phe Thr His Ala Ser Tyr His Tyr Asn Thr Ile
1685                     1690                    1695

Thr Asp Cys Tyr Gln Arg Leu Glu Phe Leu Gly Asp Ala Ile Leu
1700                     1705                    1710

Asp Tyr Leu Ile Thr Lys His Leu Tyr Glu Asp Pro Arg Gln His
1715                     1720                    1725

Ser Pro Gly Val Leu Thr Asp Leu Arg Ser Ala Leu Val Asn Asn
1730                     1735                    1740

Thr Ile Phe Ala Ser Leu Ala Val Lys Tyr Asp Tyr His Lys Tyr
1745                     1750                    1755

```
Phe Lys Ala Val Ser Pro Glu Leu Phe His Val Ile Asp Asp Phe
    1760            1765            1770

Val Gln Phe Gln Leu Glu Lys Asn Glu Met Gln Gly Met Asp Ser
1775            1780            1785

Glu Leu Arg Arg Ser Glu Asp Glu Glu Lys Glu Glu Asp Ile
    1790            1795            1800

Glu Val Pro Lys Ala Met Gly Asp Ile Phe Glu Ser Leu Ala Gly
1805            1810            1815

Ala Ile Tyr Met Asp Ser Gly Met Ser Leu Glu Met Val Trp Gln
    1820            1825            1830

Val Tyr Tyr Pro Met Met Arg Pro Leu Ile Glu Lys Phe Ser Ala
1835            1840            1845

Asn Val Pro Arg Ser Pro Val Arg Glu Leu Leu Glu Met Glu Pro
    1850            1855            1860

Glu Thr Ala Lys Phe Ser Pro Ala Glu Arg Thr Tyr Asp Gly Lys
1865            1870            1875

Val Arg Val Thr Val Glu Val Val Gly Lys Gly Lys Phe Lys Gly
    1880            1885            1890

Val Gly Arg Ser Tyr Arg Ile Ala Lys Ser Ala Ala Ala Arg Arg
1895            1900            1905

Ala Leu Arg Ser Leu Lys Ala Asn Gln Pro Gln Val Pro Asn Ser
    1910            1915            1920

<210> SEQ ID NO 23
<211> LENGTH: 1918
<212> TYPE: PRT
<213> ORGANISM: Rattus norvegicus

<400> SEQUENCE: 23

Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Val Leu Leu Thr Lys Glu
65                  70                  75                  80

Leu Ala His Gln Ile Arg Gly Asp Leu Ser Pro His Ala Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asn Leu Glu
        115                 120                 125

Val Asn Ala Ser Trp Thr Lys Glu Arg Trp Ser Gln Glu Phe Thr Lys
    130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Asp Ser Cys Pro Ser Cys Pro Arg Ile Leu Gly Leu Thr Ala Ser
        195                 200                 205
```

```
Ile Leu Asn Gly Lys Cys Asp Pro Asp Glu Leu Glu Glu Lys Ile Gln
        210                 215                 220

Lys Leu Glu Lys Ile Leu Lys Ser Gly Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
                260                 265                 270

Glu Leu Glu Glu Ala Leu Asp Phe Ile Asn Asp Cys Asn Val Ser Val
            275                 280                 285

His Ser Lys Glu Arg Asp Ser Thr Leu Ile Ser Lys Gln Ile Leu Ser
        290                 295                 300

Asp Cys Arg Ala Val Leu Val Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Leu Leu
            340                 345                 350

Arg Lys Ile His Ala Leu Cys Glu Glu Tyr Phe Ser Pro Ala Ser Leu
        355                 360                 365

Asp Leu Lys Tyr Val Thr Pro Lys Val Met Lys Leu Leu Glu Ile Leu
370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415

Asp Asp Asp Asp Glu Glu Ile Glu Glu Lys Glu Lys Pro Glu Thr
            420                 425                 430

Asn Phe Pro Ser Pro Phe Thr Asn Ile Leu Cys Gly Ile Ile Phe Val
        435                 440                 445

Glu Arg Arg Tyr Thr Ala Val Val Leu Asn Arg Leu Ile Lys Glu Ala
        450                 455                 460

Gly Lys Gln Asp Pro Glu Leu Ala Tyr Ile Ser Ser Asn Phe Ile Thr
465                 470                 475                 480

Gly His Gly Ile Gly Lys Asn Gln Pro Arg Ser Lys Gln Met Glu Ala
                485                 490                 495

Glu Phe Arg Lys Gln Glu Val Leu Arg Lys Phe Arg Ala His Glu
            500                 505                 510

Thr Asn Leu Leu Ile Ala Thr Ser Val Val Glu Glu Gly Val Asp Ile
        515                 520                 525

Pro Lys Cys Asn Leu Val Val Arg Phe Asp Leu Pro Thr Glu Tyr Arg
530                 535                 540

Ser Tyr Val Gln Ser Lys Gly Arg Ala Arg Ala Pro Ile Ser Asn Tyr
545                 550                 555                 560

Val Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
            580                 585                 590

Ser Val Asp Gly Ala Glu Ala Asp Val His Ala Val Asp Asp Asp
        595                 600                 605

Asp Val Phe Pro Pro Tyr Val Leu Arg Pro Asp Gly Gly Pro Arg
610                 615                 620

Val Thr Ile Asn Thr Ala Ile Gly His Ile Asn Arg Tyr Cys Ala Arg
625                 630                 635                 640
```

```
Leu Pro Ser Asp Pro Phe Thr His Leu Ala Pro Lys Cys Arg Thr Arg
                645                 650                 655

Glu Leu Pro Asp Gly Thr Phe Tyr Ser Thr Leu Tyr Leu Pro Ile Asn
            660                 665                 670

Ser Pro Leu Arg Ala Ser Ile Val Gly Pro Met Gly Cys Val Arg
        675                 680                 685

Leu Ala Glu Arg Val Val Ala Leu Ile Cys Cys Glu Lys Leu His Lys
    690                 695                 700

Ile Gly Glu Leu Asp Glu His Leu Met Pro Val Gly Lys Glu Thr Val
705                 710                 715                 720

Lys Tyr Glu Glu Glu Leu Asp Leu His Asp Glu Glu Thr Ser Val
                725                 730                 735

Pro Gly Arg Pro Gly Ser Thr Lys Arg Arg Gln Cys Tyr Pro Lys Ala
            740                 745                 750

Ile Pro Glu Cys Leu Arg Glu Ser Tyr Pro Lys Pro Asp Gln Pro Cys
        755                 760                 765

Tyr Leu Tyr Val Ile Gly Met Val Leu Thr Thr Pro Leu Pro Asp Glu
    770                 775                 780

Leu Asn Phe Arg Arg Arg Lys Leu Tyr Pro Pro Glu Asp Thr Thr Arg
785                 790                 795                 800

Cys Phe Gly Ile Leu Thr Ala Lys Pro Ile Pro Gln Ile Pro His Phe
                805                 810                 815

Pro Val Tyr Thr Arg Ser Gly Glu Val Thr Ile Ser Ile Glu Leu Lys
            820                 825                 830

Lys Ser Gly Phe Thr Leu Ser Gln Gln Met Leu Glu Leu Val Thr Arg
        835                 840                 845

Leu His Gln Tyr Ile Phe Ser His Ile Leu Arg Leu Glu Lys Pro Ala
    850                 855                 860

Leu Glu Phe Gln Pro Ala Gly Ala Glu Ser Ala Tyr Cys Val Leu Pro
865                 870                 875                 880

Leu Asn Val Val Asn Asp Ser Ser Thr Leu Asp Ile Asp Phe Lys Phe
                885                 890                 895

Met Glu Asp Ile Glu Lys Ser Glu Ala Arg Ile Gly Ile Pro Ser Thr
            900                 905                 910

Lys Tyr Ser Lys Glu Thr Pro Phe Val Phe Lys Leu Glu Asp Tyr Gln
        915                 920                 925

Asp Ala Val Ile Ile Pro Arg Tyr Arg Asn Phe Asp Gln Pro His Arg
    930                 935                 940

Phe Tyr Val Ala Asp Val Tyr Thr Asp Leu Thr Pro Leu Ser Lys Phe
945                 950                 955                 960

Pro Ser Pro Glu Tyr Glu Thr Phe Ala Glu Tyr Tyr Lys Thr Lys Tyr
                965                 970                 975

Asn Leu Asp Leu Thr Asn Leu Asn Gln Pro Leu Leu Asp Val Asp His
            980                 985                 990

Thr Ser Ser Arg Leu Asn Leu Leu Thr Pro Arg His Leu Asn Gln Lys
        995                 1000                1005

Gly Lys Ala Leu Pro Leu Ser Ser Ala Glu Lys Arg Lys Ala Lys
    1010                1015                1020

Trp Glu Ser Leu Gln Asn Lys Gln Ile Leu Val Pro Glu Leu Cys
    1025                1030                1035

Ala Ile His Pro Ile Pro Ala Ser Leu Trp Arg Lys Ala Val Cys
    1040                1045                1050

Leu Pro Ser Ile Leu Tyr Arg Leu His Cys Leu Leu Thr Ala Glu
```

```
              1055                1060                1065

Glu  Leu  Arg  Ala  Gln  Thr  Ala  Ser  Asp  Ala  Gly  Val  Gly  Val  Arg
     1070                1075                1080

Ser  Leu  Pro  Ala  Asp  Phe  Arg  Tyr  Pro  Asn  Leu  Asp  Phe  Gly  Trp
     1085                1090                1095

Lys  Lys  Ser  Ile  Asp  Ser  Lys  Ser  Phe  Ile  Ser  Thr  Cys  Asn  Ser
     1100                1105                1110

Ser  Leu  Ala  Glu  Ser  Asp  Asn  Tyr  Cys  Lys  His  Ser  Thr  Thr  Val
     1115                1120                1125

Val  Pro  Glu  Asn  Ala  Ala  His  Gln  Gly  Ala  Thr  Arg  Pro  Ser  Leu
     1130                1135                1140

Glu  Asn  His  Asp  Gln  Met  Ser  Val  Asn  Cys  Lys  Arg  Leu  Pro  Ala
     1145                1150                1155

Glu  Ser  Pro  Ala  Lys  Leu  Gln  Ser  Glu  Val  Ser  Val  Asp  Leu  Thr
     1160                1165                1170

Ala  Ile  Asn  Gly  Leu  Ser  Tyr  Asn  Lys  Ser  Leu  Ala  Asn  Gly  Ser
     1175                1180                1185

Tyr  Asp  Leu  Val  Asn  Arg  Asp  Phe  Cys  Gln  Gly  Asn  Gln  Leu  Thr
     1190                1195                1200

Tyr  Phe  Lys  Gln  Glu  Ile  Pro  Val  Gln  Pro  Thr  Thr  Ser  Tyr  Pro
     1205                1210                1215

Ile  Gln  Asn  Leu  Tyr  Asn  Tyr  Glu  Asn  Gln  Pro  Thr  Pro  Ser  Asn
     1220                1225                1230

Glu  Cys  Pro  Leu  Leu  Ser  Asn  Lys  Tyr  Leu  Asp  Gly  Asn  Ala  Asn
     1235                1240                1245

Thr  Ser  Thr  Ser  Asp  Gly  Ser  Pro  Ala  Gly  Ser  Pro  Arg  Pro  Ala
     1250                1255                1260

Met  Met  Thr  Ala  Val  Glu  Ala  Leu  Glu  Gly  Arg  Thr  Asp  Ser  Glu
     1265                1270                1275

Gln  Ser  Pro  Ser  Val  Gly  His  Ser  Ser  Arg  Thr  Leu  Gly  Pro  Asn
     1280                1285                1290

Pro  Gly  Leu  Ile  Leu  Gln  Ala  Leu  Thr  Leu  Ser  Asn  Ala  Ser  Asp
     1295                1300                1305

Gly  Phe  Asn  Leu  Glu  Arg  Leu  Glu  Met  Leu  Gly  Asp  Ser  Phe  Leu
     1310                1315                1320

Lys  His  Ala  Ile  Thr  Thr  Tyr  Leu  Phe  Cys  Thr  Tyr  Pro  Asp  Ala
     1325                1330                1335

His  Glu  Gly  Arg  Leu  Ser  Tyr  Met  Arg  Ser  Lys  Lys  Val  Ser  Asn
     1340                1345                1350

Cys  Asn  Leu  Tyr  Arg  Leu  Gly  Lys  Lys  Gln  Gly  Leu  Pro  Ser  Arg
     1355                1360                1365

Met  Val  Val  Ser  Ile  Phe  Asp  Pro  Pro  Val  Asn  Trp  Leu  Pro  Pro
     1370                1375                1380

Gly  Tyr  Val  Val  Asn  Gln  Asp  Lys  Ser  Asn  Ser  Glu  Lys  Trp  Glu
     1385                1390                1395

Lys  Asp  Glu  Met  Thr  Lys  Asp  Cys  Leu  Leu  Ala  Asn  Gly  Lys  Leu
     1400                1405                1410

Gly  Glu  Asp  Cys  Glu  Glu  Glu  Glu  Glu  Glu  Leu  Ala  Trp  Arg
     1415                1420                1425

Ala  Pro  Lys  Glu  Glu  Ala  Glu  Tyr  Glu  Asp  Leu  Leu  Glu  Tyr
     1430                1435                1440

Asp  Gln  Glu  His  Ile  Gln  Phe  Ile  Asp  Ser  Met  Leu  Met  Gly  Ser
     1445                1450                1455
```

-continued

```
Gly Ala Phe Val Lys Lys Ile Pro Leu Ser Pro Phe Ser Thr Ser
1460             1465             1470

Asp Ser Ala Tyr Glu Trp Lys Met Pro Lys Lys Ala Ser Leu Gly
1475             1480             1485

Ser Val Pro Phe Ser Ser Asp Leu Glu Asp Phe Asp Tyr Ser Ser
1490             1495             1500

Trp Asp Ala Met Cys Tyr Leu Asp Pro Ser Lys Ala Val Glu Glu
1505             1510             1515

Asp Asp Phe Val Val Gly Phe Trp Asn Pro Ser Glu Glu Asn Cys
1520             1525             1530

Gly Val Asp Thr Gly Lys Gln Ser Ile Ser Tyr Asp Leu His Thr
1535             1540             1545

Glu Gln Cys Ile Ala Asp Lys Ser Ile Ala Asp Cys Val Glu Ala
1550             1555             1560

Leu Leu Gly Cys Tyr Leu Thr Ser Cys Gly Glu Arg Ala Ala Gln
1565             1570             1575

Leu Phe Leu Cys Ser Leu Gly Leu Lys Val Leu Pro Val Ile Lys
1580             1585             1590

Arg Thr Ser Arg Asp Lys Ala Ser Tyr Pro Ala Gln Glu Asn Ser
1595             1600             1605

Ser Ser Gln Gln Lys Ser Pro Ser Gly Ser Cys Ala Ala Ala Val
1610             1615             1620

Ser Pro Arg Ser Ser Ala Gly Lys Asp Leu Glu Tyr Gly Cys Leu
1625             1630             1635

Lys Ile Pro Pro Arg Cys Met Phe Asp His Pro Asp Ala Glu Lys
1640             1645             1650

Thr Leu Asn His Leu Ile Ser Gly Phe Glu Asn Phe Glu Lys Lys
1655             1660             1665

Ile Asn Tyr Ile Phe Lys Asn Lys Ala Tyr Leu Leu Gln Ala Phe
1670             1675             1680

Thr His Ala Ser Tyr His Tyr Asn Thr Ile Thr Asp Cys Tyr Gln
1685             1690             1695

Arg Leu Glu Phe Leu Gly Asp Ala Ile Leu Asp Tyr Leu Ile Thr
1700             1705             1710

Lys His Leu Tyr Glu Asp Pro Arg Gln His Ser Pro Gly Val Leu
1715             1720             1725

Thr Asp Leu Arg Ser Ala Leu Val Asn Asn Thr Ile Phe Ala Ser
1730             1735             1740

Leu Ala Val Lys Tyr Asp Tyr His Lys Tyr Phe Lys Ala Val Ser
1745             1750             1755

Pro Glu Leu Phe His Val Ile Asp Asp Phe Val Gln Phe Gln Leu
1760             1765             1770

Glu Lys Asn Glu Met Gln Gly Met Asp Ser Glu Leu Arg Arg Ser
1775             1780             1785

Glu Glu Asp Glu Glu Lys Glu Glu Asp Ile Glu Val Pro Lys Ala
1790             1795             1800

Met Gly Asp Ile Phe Glu Ser Leu Ala Gly Ala Ile Tyr Met Asp
1805             1810             1815

Ser Gly Met Ser Leu Glu Val Val Trp Gln Val Tyr Tyr Pro Met
1820             1825             1830

Met Arg Pro Leu Ile Glu Lys Phe Ser Ala Asn Val Pro Arg Ser
1835             1840             1845

Pro Val Arg Glu Leu Leu Glu Met Glu Pro Glu Thr Ala Lys Phe
1850             1855             1860
```

-continued

```
Ser Pro Ala Glu Arg Thr Tyr Asp Gly Lys Val Arg Val Thr Val
    1865                1870                1875

Glu Val Val Gly Lys Gly Lys Phe Lys Gly Val Gly Arg Ser Tyr
    1880                1885                1890

Arg Ile Ala Lys Ser Ala Ala Ala Arg Arg Ala Leu Arg Ser Leu
    1895                1900                1905

Lys Ala Asn Gln Pro Leu Val Pro Asn Ser
    1910                1915
```

<210> SEQ ID NO 24
<211> LENGTH: 1916
<212> TYPE: PRT
<213> ORGANISM: Mus musculus

<400> SEQUENCE: 24

```
Leu Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Val Leu Leu Thr Lys Glu
65                  70                  75                  80

Leu Ala His Gln Ile Arg Gly Asp Leu Asn Pro His Ala Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asp Leu Glu
        115                 120                 125

Val Asn Ala Ser Trp Thr Lys Glu Arg Trp Ser Gln Glu Phe Thr Lys
    130                 135                 140

His Gln Val Leu Ile Met Thr Cys Tyr Val Ala Leu Thr Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Glu Ser Cys Pro Ser Cys Pro Arg Ile Leu Gly Leu Thr Ala Ser
        195                 200                 205

Ile Leu Asn Gly Lys Cys Asp Pro Glu Glu Leu Glu Glu Lys Ile Gln
    210                 215                 220

Lys Leu Glu Arg Ile Leu Arg Ser Asp Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
            260                 265                 270

Glu Leu Glu Ala Ala Leu Asp Phe Ile Asn Asp Cys Asn Val Ala Val
        275                 280                 285

His Ser Lys Glu Arg Asp Ser Thr Leu Ile Ser Lys Gln Ile Leu Ser
    290                 295                 300

Asp Cys Arg Ala Val Leu Val Val Leu Gly Pro Trp Cys Ala Asp Lys
305                 310                 315                 320
```

-continued

```
Val Ala Gly Met Met Val Arg Glu Leu Gln Lys Tyr Ile Lys His Glu
            325                 330                 335
Gln Glu Glu Leu His Arg Lys Phe Leu Leu Phe Thr Asp Thr Leu Leu
            340                 345                 350
Arg Lys Ile His Ala Leu Cys Glu Tyr Phe Ser Pro Ala Ser Leu
        355                 360                 365
Asp Leu Lys Tyr Val Thr Pro Lys Val Met Lys Leu Leu Glu Ile Leu
        370                 375                 380
Arg Lys Tyr Lys Pro Tyr Glu Arg Gln Gln Phe Glu Ser Val Glu Trp
385                 390                 395                 400
Tyr Asn Asn Arg Asn Gln Asp Asn Tyr Val Ser Trp Ser Asp Ser Glu
                405                 410                 415
Asp Asp Asp Asp Glu Glu Ile Glu Glu Lys Glu Lys Pro Glu Thr
        420                 425                 430
Asn Phe Pro Ser Pro Phe Thr Asn Ile Leu Cys Gly Ile Ile Phe Val
        435                 440                 445
Glu Arg Arg Tyr Thr Ala Val Val Leu Asn Arg Leu Ile Lys Glu Ala
    450                 455                 460
Gly Lys Gln Asp Pro Glu Leu Ala Tyr Ile Ser Ser Asn Phe Ile Thr
465                 470                 475                 480
Gly His Gly Ile Gly Lys Asn Gln Pro Arg Ser Lys Gln Met Glu Ala
                485                 490                 495
Glu Phe Arg Lys Gln Glu Val Leu Arg Lys Phe Arg Ala His Glu
            500                 505                 510
Thr Asn Leu Leu Ile Ala Thr Ser Val Val Glu Glu Gly Val Asp Ile
        515                 520                 525
Pro Lys Cys Asn Leu Val Val Arg Phe Asp Leu Pro Thr Glu Tyr Arg
        530                 535                 540
Ser Tyr Val Gln Ser Lys Gly Arg Ala Arg Ala Pro Ile Ser Asn Tyr
545                 550                 555                 560
Val Met Leu Ala Asp Thr Asp Lys Ile Lys Ser Phe Glu Glu Asp Leu
                565                 570                 575
Lys Thr Tyr Lys Ala Ile Glu Lys Ile Leu Arg Asn Lys Cys Ser Lys
            580                 585                 590
Ser Ala Asp Gly Ala Glu Ala Asp Val His Ala Gly Val Asp Asp Glu
        595                 600                 605
Asp Ala Phe Pro Pro Tyr Val Leu Arg Pro Asp Asp Gly Gly Pro Arg
    610                 615                 620
Val Thr Ile Asn Thr Ala Ile Gly His Ile Asn Arg Tyr Cys Ala Arg
625                 630                 635                 640
Leu Pro Ser Asp Pro Phe Thr His Leu Ala Pro Lys Cys Arg Thr Arg
                645                 650                 655
Glu Leu Pro Asp Gly Thr Phe Tyr Ser Thr Leu Tyr Leu Pro Ile Asn
            660                 665                 670
Ser Pro Leu Arg Ala Ser Ile Val Gly Pro Pro Met Asp Ser Val Arg
        675                 680                 685
Leu Ala Glu Arg Val Val Ala Leu Ile Cys Cys Glu Lys Leu His Lys
    690                 695                 700
Ile Gly Glu Leu Asp Glu His Leu Met Pro Val Gly Lys Glu Thr Val
705                 710                 715                 720
Lys Tyr Glu Glu Glu Leu Asp Leu His Asp Glu Glu Thr Ser Val
                725                 730                 735
Pro Gly Arg Pro Gly Ser Thr Lys Arg Arg Gln Cys Tyr Pro Lys Ala
```

```
                   740                 745                 750
Ile Pro Glu Cys Leu Arg Glu Ser Tyr Pro Lys Pro Asp Gln Pro Cys
            755                 760                 765

Tyr Leu Tyr Val Ile Gly Met Val Leu Thr Thr Pro Leu Pro Asp Glu
    770                 775                 780

Leu Asn Phe Arg Arg Arg Lys Leu Tyr Pro Pro Glu Asp Thr Thr Arg
785                 790                 795                 800

Cys Phe Gly Ile Leu Thr Ala Lys Pro Ile Pro Gln Ile Pro His Phe
                805                 810                 815

Pro Val Tyr Thr Arg Ser Gly Glu Val Thr Ile Ser Ile Glu Leu Lys
        820                 825                 830

Lys Ser Gly Phe Thr Leu Ser Gln Gln Met Leu Glu Leu Ile Thr Arg
            835                 840                 845

Leu His Gln Tyr Ile Phe Ser His Ile Leu Arg Leu Glu Lys Pro Ala
    850                 855                 860

Leu Glu Phe Lys Pro Thr Gly Ala Glu Ser Ala Tyr Cys Val Leu Pro
865                 870                 875                 880

Leu Asn Val Val Asn Asp Ser Gly Thr Leu Asp Ile Asp Phe Lys Phe
                885                 890                 895

Met Glu Asp Ile Glu Lys Ser Glu Ala Arg Ile Gly Ile Pro Ser Thr
        900                 905                 910

Lys Tyr Ser Lys Glu Thr Pro Phe Val Phe Lys Leu Glu Asp Tyr Gln
        915                 920                 925

Asp Ala Val Ile Ile Pro Arg Tyr Arg Asn Phe Asp Gln Pro His Arg
    930                 935                 940

Phe Tyr Val Ala Asp Val Tyr Thr Asp Leu Thr Pro Leu Ser Lys Phe
945                 950                 955                 960

Pro Ser Pro Glu Tyr Glu Thr Phe Ala Glu Tyr Tyr Lys Thr Lys Tyr
                965                 970                 975

Asn Leu Asp Leu Thr Asn Leu Asn Gln Pro Leu Leu Asp Val Asp His
            980                 985                 990

Thr Ser Ser Arg Leu Asn Leu Leu Thr Pro Arg His Leu Asn Gln Lys
        995                 1000                1005

Gly Lys Ala Leu Pro Leu Ser Ser Ala Glu Lys Arg Lys Ala Lys
    1010                1015                1020

Trp Glu Ser Leu Gln Asn Lys Gln Ile Leu Val Pro Glu Leu Cys
    1025                1030                1035

Ala Ile His Pro Ile Pro Ala Ser Leu Trp Arg Lys Ala Val Cys
    1040                1045                1050

Leu Pro Ser Ile Leu Tyr Arg Leu His Cys Leu Leu Thr Ala Glu
    1055                1060                1065

Glu Leu Arg Ala Gln Thr Ala Ser Asp Ala Gly Val Gly Val Arg
    1070                1075                1080

Ser Leu Pro Val Asp Phe Arg Tyr Pro Asn Leu Asp Phe Gly Trp
    1085                1090                1095

Lys Lys Ser Ile Asp Ser Lys Ser Phe Ile Ser Ser Cys Asn Ser
    1100                1105                1110

Ser Leu Ala Glu Ser Asp Asn Tyr Cys Lys His Ser Thr Thr Val
    1115                1120                1125

Val Pro Glu His Ala Ala His Gln Gly Ala Thr Arg Pro Ser Leu
    1130                1135                1140

Glu Asn His Asp Gln Met Ser Val Asn Cys Lys Arg Leu Pro Ala
    1145                1150                1155
```

-continued

Glu Ser Pro Ala Lys Leu Gln Ser Glu Val Ser Thr Asp Leu Thr
1160              1165              1170

Ala Ile Asn Gly Leu Ser Tyr Asn Lys Asn Leu Ala Asn Gly Ser
1175              1180              1185

Tyr Asp Leu Val Asn Arg Asp Phe Cys Gln Gly Asn Gln Leu Asn
1190              1195              1200

Tyr Phe Lys Gln Glu Ile Pro Val Gln Pro Thr Thr Ser Tyr Pro
1205              1210              1215

Ile Gln Asn Leu Tyr Asn Tyr Glu Asn Gln Pro Lys Pro Ser Asn
1220              1225              1230

Glu Cys Pro Leu Leu Ser Asn Thr Tyr Leu Asp Gly Asn Ala Asn
1235              1240              1245

Thr Ser Thr Ser Asp Gly Ser Pro Ala Val Ser Thr Met Pro Ala
1250              1255              1260

Met Met Asn Ala Val Lys Ala Leu Lys Asp Arg Met Asp Ser Glu
1265              1270              1275

Gln Ser Pro Ser Val Gly Tyr Ser Ser Arg Thr Leu Gly Pro Asn
1280              1285              1290

Pro Gly Leu Ile Leu Gln Ala Leu Thr Leu Ser Asn Ala Ser Asp
1295              1300              1305

Gly Phe Asn Leu Glu Arg Leu Glu Met Leu Gly Asp Ser Phe Leu
1310              1315              1320

Lys His Ala Ile Thr Thr Tyr Leu Phe Cys Thr Tyr Pro Asp Ala
1325              1330              1335

His Glu Gly Arg Leu Ser Tyr Met Arg Ser Lys Lys Val Ser Asn
1340              1345              1350

Cys Asn Leu Tyr Arg Leu Gly Lys Lys Lys Gly Leu Pro Ser Arg
1355              1360              1365

Met Val Val Ser Ile Phe Asp Pro Pro Val Asn Trp Leu Pro Pro
1370              1375              1380

Gly Tyr Val Val Asn Gln Asp Lys Ser Asn Ser Glu Lys Trp Glu
1385              1390              1395

Lys Asp Glu Met Thr Lys Asp Cys Leu Leu Ala Asn Gly Lys Leu
1400              1405              1410

Gly Glu Ala Cys Glu Glu Glu Asp Leu Thr Trp Arg Ala Pro
1415              1420              1425

Lys Glu Glu Ala Glu Asp Glu Asp Asp Phe Leu Glu Tyr Asp Gln
1430              1435              1440

Glu His Ile Gln Phe Ile Asp Ser Met Leu Met Gly Ser Gly Ala
1445              1450              1455

Phe Val Arg Lys Ile Ser Leu Ser Pro Phe Ser Ala Ser Asp Ser
1460              1465              1470

Ala Tyr Glu Trp Lys Met Pro Lys Lys Ala Ser Leu Gly Ser Met
1475              1480              1485

Pro Phe Ala Ser Gly Leu Glu Asp Phe Asp Tyr Ser Ser Trp Asp
1490              1495              1500

Ala Met Cys Tyr Leu Asp Pro Ser Lys Ala Val Glu Glu Asp Asp
1505              1510              1515

Phe Val Val Gly Phe Trp Asn Pro Ser Glu Glu Asn Cys Gly Val
1520              1525              1530

Asp Thr Gly Lys Gln Ser Ile Ser Tyr Asp Leu His Thr Glu Gln
1535              1540              1545

Cys Ile Ala Asp Lys Ser Ile Ala Asp Cys Val Glu Ala Leu Leu
1550              1555              1560

Gly Cys Tyr Leu Thr Ser Cys Gly Glu Arg Ala Ala Gln Leu Phe
1565                1570                1575

Leu Cys Ser Leu Gly Leu Lys Val Leu Pro Val Ile Lys Arg Thr
1580                1585                1590

Ser Arg Glu Lys Ala Leu Asp Pro Ala Gln Glu Asn Gly Ser Ser
1595                1600                1605

Gln Gln Lys Ser Leu Ser Gly Ser Cys Ala Ser Pro Val Gly Pro
1610                1615                1620

Arg Ser Ser Ala Gly Lys Asp Leu Glu Tyr Gly Cys Leu Lys Ile
1625                1630                1635

Pro Pro Arg Cys Met Phe Asp His Pro Asp Ala Glu Lys Thr Leu
1640                1645                1650

Asn His Leu Ile Ser Gly Phe Glu Thr Phe Glu Lys Lys Ile Asn
1655                1660                1665

Tyr Arg Phe Lys Asn Lys Ala Tyr Leu Leu Gln Ala Phe Thr His
1670                1675                1680

Ala Ser Tyr His Tyr Asn Thr Ile Thr Asp Cys Tyr Gln Arg Leu
1685                1690                1695

Glu Phe Leu Gly Asp Ala Ile Leu Asp Tyr Leu Ile Thr Lys His
1700                1705                1710

Leu Tyr Glu Asp Pro Arg Gln His Ser Pro Gly Val Leu Thr Asp
1715                1720                1725

Leu Arg Ser Ala Leu Val Asn Asn Thr Ile Phe Ala Ser Leu Ala
1730                1735                1740

Val Lys Tyr Asp Tyr His Lys Tyr Phe Lys Ala Val Ser Pro Glu
1745                1750                1755

Leu Phe His Val Ile Asp Asp Phe Val Lys Phe Gln Leu Glu Lys
1760                1765                1770

Asn Glu Met Gln Gly Met Asp Ser Glu Leu Arg Arg Ser Glu Glu
1775                1780                1785

Asp Glu Glu Lys Glu Glu Asp Ile Glu Val Pro Lys Ala Met Gly
1790                1795                1800

Asp Ile Phe Glu Ser Leu Ala Gly Ala Ile Tyr Met Asp Ser Gly
1805                1810                1815

Met Ser Leu Glu Val Val Trp Gln Val Tyr Tyr Pro Met Met Gln
1820                1825                1830

Pro Leu Ile Glu Lys Phe Ser Ala Asn Val Pro Arg Ser Pro Val
1835                1840                1845

Arg Glu Leu Leu Glu Met Glu Pro Glu Thr Ala Lys Phe Ser Pro
1850                1855                1860

Ala Glu Arg Thr Tyr Asp Gly Lys Val Arg Val Thr Val Glu Val
1865                1870                1875

Val Gly Lys Gly Lys Phe Lys Gly Val Gly Arg Ser Tyr Arg Ile
1880                1885                1890

Ala Lys Ser Ala Ala Ala Arg Arg Ala Leu Arg Ser Leu Lys Ala
1895                1900                1905

Asn Gln Pro Gln Val Pro Asn Ser
1910                1915

<210> SEQ ID NO 25
<211> LENGTH: 4
<212> TYPE: PRT
<213> ORGANISM: Artificial Sequence

```
<220> FEATURE:
<223> OTHER INFORMATION: Synthetic polypeptide

<400> SEQUENCE: 25

Asp Glu Cys His
1
```